US007264951B1

(12) United States Patent  
Bringi et al.

(10) Patent No.: US 7,264,951 B1  
(45) Date of Patent: Sep. 4, 2007

(54) **ENHANCED PRODUCTION OF TAXOL AND TAXANES BY CELL CULTURES OF *TAXUS* SPECIES**

(75) Inventors: Venkataraman Bringi, Ithaca, NY (US); Prakash G. Kadkade, Marlboro, MA (US); Christopher L. Prince, Lansing, NY (US); Braden L. Roach, Interlaken, NY (US)

(73) Assignee: Phyton, Inc., Ithaca, NY (US)

( * ) Notice: Subject to any disclaimer, the term of this patent is extended or adjusted under 35 U.S.C. 154(b) by 236 days.

(21) Appl. No.: 09/083,198

(22) Filed: May 22, 1998

Related U.S. Application Data

(60) Continuation-in-part of application No. PCT/US97/08907, filed on May 27, 1997, which is a continuation of application No. 08/653,036, filed on May 24, 1996, now abandoned, which is a continuation-in-part of application No. 08/653,036, which is a continuation-in-part of application No. 08/370,494, filed on Jan. 9, 1995, now abandoned, which is a division of application No. 07/874,344, filed on Apr. 24, 1992, now Pat. No. 5,407,816, which is a continuation-in-part of application No. 07/839,144, filed on Feb. 20, 1992, now abandoned.

(51) Int. Cl.  
  *C12P 17/02* (2006.01)
(52) U.S. Cl. ............... 435/123; 435/244; 435/420; 435/431; 549/510; 549/511
(58) Field of Classification Search ............... 435/123, 435/244, 240.4, 420, 431; 549/510, 511  
See application file for complete search history.

(56) References Cited

U.S. PATENT DOCUMENTS

| 4,717,664 A | 1/1988 | Hara et al. |
| 5,015,744 A | 5/1991 | Holton ............... 549/510 |
| 5,019,504 A | 5/1991 | Christen et al. |
| 5,279,953 A | 1/1994 | Stahlhut |
| 5,310,672 A | 5/1994 | Wann et al. |
| 5,312,740 A | 5/1994 | Saito et al. |
| 5,322,779 A | 6/1994 | Strobel et al. |
| 5,334,529 A | 8/1994 | Adams et al. |
| 5,344,775 A | 9/1994 | Smith |
| 5,445,809 A | 8/1995 | Strobel et al. |
| 5,451,392 A | 9/1995 | Strobel et al. |
| 5,527,702 A | 6/1996 | Cino et al. |
| 5,547,866 A | 8/1996 | Durzan et al. |
| 5,620,875 A | 4/1997 | Hoffman et al. |
| 5,637,484 A | 6/1997 | Yukimune et al. ........ 435/123 |
| 5,665,576 A | 9/1997 | Cino et al. |
| 5,670,663 A | 9/1997 | Durzan et al. |
| 5,850,032 A | 12/1998 | Wann et al. |
| 5,861,302 A | 1/1999 | Stierle et al. |
| 5,871,979 A | 2/1999 | Choi et al. |
| 5,908,759 A | 6/1999 | Stierle et al. |
| 5,916,783 A | 6/1999 | Stierle et al. |
| 5,968,789 A | 10/1999 | Yukimune et al. |
| 6,013,493 A | 1/2000 | Stierle et al. |
| 6,030,818 A | 2/2000 | Page et al. |
| 6,069,009 A | 5/2000 | Pepin et al. |
| 6,248,572 B1 | 6/2001 | Choi et al. |
| 6,365,407 B1 | 4/2002 | Kulkarni et al. |
| 6,403,343 B2 | 6/2002 | Yukimune et al. |
| 6,428,989 B1 | 8/2002 | Yukimune et al. |
| 6,465,221 B1 | 10/2002 | Yukimune et al. |
| 2002/0012976 A1 | 1/2002 | Yukimune et al. |

FOREIGN PATENT DOCUMENTS

| CA | 1317247 | 4/1993 |
| CA | 2153986 | 5/1995 |
| DE | 122208 | 7/1992 |
| EP | 325933 | 8/1989 |
| EP | 378921 | 12/1989 |
| EP | 378921 A2 | 7/1990 |
| EP | 529083 | 3/1993 |
| EP | 555485 | 8/1993 |
| EP | 568821 A1 | 11/1993 |
| EP | 568821 B1 | 11/1993 |
| EP | 577274 | 1/1994 |
| EP | 672162 | 9/1995 |
| EP | 683232 | 11/1995 |
| EP | 727492 | 8/1996 |

(Continued)

OTHER PUBLICATIONS

Fuji, et al., "Novel Diterpenoids From Taxus Chinensis," *Journal of Natural Products*, vol. 56, No. 9, pp. 1520-1531 (Sep. 1993).

(Continued)

*Primary Examiner*—Irene Marx  
(74) *Attorney, Agent, or Firm*—Hunton & Williams LLP

(57) ABSTRACT

This invention provides methods whereby taxol, baccatin III, and other taxol-like compounds, or taxanes, can be produced in very high yield from all known *Taxus* species, e.g., *brevifolia, canadensis, cuspidata, baccata, globosa, floridana, wallichiana, media* and *chinensis*. Particular modifications of culture conditions (i.e., media composition and operating modes) have been discovered to enhance the yield of various taxanes from cell culture of all species of *Taxus*. Particularly preferred enhancement agents include silver ion or complex, jasmonic acid (especially the methyl ester), auxin-related growth regulators, and inhibitors of the phenylpropanoid pathway, such as 3,4-methylenedioxy-6-nitrocinnamic acid. These enhancement agents may be used alone or in combination with one another or other yield-enhancing conditions. While the yield of taxanes from plant cell culture of *T. chinensis* is particularly enhanced by use of one or more of these conditions, yield of taxanes for all *Taxus* species has been found to benefit from use of these conditions.

68 Claims, 11 Drawing Sheets

FOREIGN PATENT DOCUMENTS

| | | |
|---|---|---|
| EP | 769064 B1 | 4/1997 |
| EP | 774010 B1 | 5/1997 |
| EP | 830059 B1 | 3/1998 |
| EP | 882231 | 12/1998 |
| EP | 960944 A1 | 12/1999 |
| EP | 1054065 A1 | 11/2000 |
| EP | 10633000 A2 | 12/2000 |
| EP | 1164197 A1 | 12/2001 |
| JP | 5244971 A2 | 9/1993 |
| JP | 5336985 A2 | 12/1993 |
| JP | 6181785 A2 | 7/1994 |
| JP | 6292588 A2 | 10/1994 |
| JP | 6296493 A2 | 10/1994 |
| JP | 7135967 A2 | 5/1995 |
| JP | 7255495 A2 | 10/1995 |
| JP | 7308196 A2 | 11/1995 |
| JP | 7308197 A2 | 11/1995 |
| JP | 8009983 A2 | 1/1996 |
| JP | 8033490 A2 | 2/1996 |
| JP | 8056681 A2 | 3/1996 |
| JP | 8070880 A2 | 3/1996 |
| JP | 8116981 A2 | 5/1996 |
| JP | 8140690 A2 | 6/1996 |
| JP | 8149984 A2 | 6/1996 |
| JP | 8154691 A2 | 6/1996 |
| JP | 8154692 A2 | 6/1996 |
| JP | 8163991 A2 | 6/1996 |
| JP | 198863 | 8/1996 |
| JP | 8205881 A2 | 8/1996 |
| JP | 8205882 A2 | 8/1996 |
| JP | 8298993 A2 | 11/1996 |
| JP | 9028392 A2 | 2/1997 |
| JP | 9056387 A2 | 3/1997 |
| JP | 10042888 A2 | 2/1998 |
| JP | 10052294 A2 | 2/1998 |
| JP | 10052295 A2 | 2/1998 |
| JP | 10052296 A2 | 2/1998 |
| JP | 11046782 A2 | 2/1999 |
| JP | 11332590 A2 | 12/1999 |
| JP | 2000106893 A2 | 4/2000 |
| JP | 2000197497 A2 | 7/2000 |
| JP | 2000333691 A2 | 12/2000 |
| WO | 89/06687 | 7/1989 |
| WO | WO91/18512 | 12/1991 |
| WO | W 92/13961 | 8/1992 |
| WO | 92/18492 | 10/1992 |
| WO | W 93/10253 | 5/1993 |
| WO | 93/17121 | 9/1993 |
| WO | 93/19585 | 10/1993 |
| WO | WO93/21338 | 10/1993 |
| WO | 93/23555 | 11/1993 |
| WO | 95/02063 | 1/1995 |
| WO | 96/02656 A1 | 2/1996 |
| WO | 96/34110 | 10/1996 |
| WO | WO96/34522 | 11/1996 |
| WO | WO96/34973 | 11/1996 |
| WO | 97/30352 | 8/1997 |
| WO | 97/31100 | 8/1997 |
| WO | 97/44476 | 11/1997 |
| WO | 98/37176 | 8/1998 |
| WO | 99/00513 | 1/1999 |
| WO | 99/32651 | 7/1999 |
| WO | 01/73096 A1 | 10/2001 |

OTHER PUBLICATIONS

Guerite-Voegelein, et al., "Taxol and Derivatives: A Biogenetic Hypothesis," *Journal of Natural Products*, vol. 50, No. 1, pp. 9-18 (Jan.-Feb. 1987).

Gundlach, et al., "Jasmonic Acid is a Signal Transducer in Elicitor-Induced Plant Cell Cultures," *Proc. Natl. Acad. Sci. USA*, vol. 89, pp. 2389-2393 (Mar. 1992).

Mueller, et al., "Signaling in the Elicitation Process is Mediated through the Octadecanoid Pathway Leading to Jasmonic Acid," *Proc. Natl. Acad. Sci. USA*, vol. 90, pp. 7490-7494 (Aug. 1993).

Reid, "The Role of Ethylene", in Davies, ed., *Plant Hormones and Their Role in Plant Growth and Development*, Martinus Nijhoff Publishers, pp. 260-271.

Rokem, et al., "Secondary Metabolites From Plant Cell Suspension Cultures: Methods for Yield Improvement," *Advances in Biotechnological Processes*, vol. 4, pp. 241-274 (1985).

Rao, "Taxol and Related Taxanes. I Taxanes of *Taxus brevifolia* Bark," *Pharmaceutical Research*, vol. 10, No. 4, pp. 521-524 (1993).

Schumacher, et al., "Elicitation of Benzophenanthridine Alkaloid Synthesis in Eschscholtzia Cell Cultures," *Plant Cell Reports*, vol. 6, pp. 410-413 (1987).

Zamir, et al., "Biosynthetic Building Blocks of *Taxus canadensis* Taxanes," *Tetrahedron Letters*, vol. 33, No. 36, pp. 5235-5236 (1992).

Zhang, et al., "New Taxanes from Taxus chinensis," *Chemical Abstracts*, 113(23), Abstr. 208344z (Dec. 3, 1990).

Zhang, et al., "Taxanes from Taxus chinensis," *Chemical Abstracts*, 115, (Abstr. 131964h (Sep. 30, 1991).

Jia, et al., "Taxanes from Taxus chinensis," *Chemical Abstracts*, 116(7), Abstr. 55524t (Feb. 17, 1992).

Jia, et al., "Taxanes from Taxus chinensis III," *Chemical Abstracts*, 117(1), Abstr. 8234j (Jul. 6, 1992).

Edgington, "Taxol out of the woods," *Bio/Technology*, 9, pp. 933-936 (1991).

Crueger, et al., "Growth Kinetics of Microorganisms, "In *Biotechnology: A Textbook of Industrial Microbiology*, 2nd ed., T. Brock, ed. Sunderland, MA: Sinauer Associates, pp. 67-68, (1990).

Anderson, "Jasmonic Acid-Dependent Increases in the Level of Specific Polypeptides in Soybean Suspension Cultures and Seedlings." In *Plant Growth Regulation* 7(4). Springer-Verlag New York, pp. 203-212 (1988).

Christen, et al., "Cell Cultures as a Means to Produce Taxol" (Abstract), *Proceedings of the American Association for Cancer Research* 30, p. 566 (Mar. 1989).

Constabel, "Cell Culture in Phytochemistry," In *Cell Culture and Somatic Genetics of Plants*, vol. 4, Constabel et al. (eds.). Academic Press, New York, pp. 3-13 (1987).

Davies (ed.), Table of Contents of *Plant Hormones: Physiology, Biochemistry and Molecular Biology*, 2nd ed., Kluwer Academic Publishers, pp. V-VII (1995).

DiCosmo, "Eliciting Secondary Metabolism in Plant Cell Cultures," *Trends in Biotechnology*. 3, pp. 318-322 (1985).

Farmer, et al., "Octadecanoid Precursors of Jasmonic Acid Activate the Synthesis of Wound-Inducible Proteinase Inhibitors," *The Plant Cell* 4, pp. 129-134 (1992).

Farmer, et al., "Interplant Communication: Airborne Methyl Jasmonate Indicues Synthesis of Proteinase Inhibitors in Plant Leaves," *Proc. Natl. Acad. Sci. USA* 87, pp. 7713-7716 (1990).

Farmer, et al., "Regulation of Expression of Proteinase Inhibitor Genes by Methyl Jasmonate and Jasmonic Acid," *Plant Physiol*. 98, pp. 995-1002 (1992).

Franceschi, et al., "Induction of Soybean Vegetative Storage Proteins and Anthocyanins by Low-Level Atmospheric Methyl Jasmonate," In *Proc. Natl. Acad. Sci USA* 88, pp. 6745-6749, (1991).

George, "Plant Growth Regulators," In *Plant Propagation by Tissue Culture, Part 1*, 2nd ed. Exegetics Limited, pp. 420-425, 479 (1993).

George, "Problems in Initiating and Maintaining Cultures," In *Plant Propagation by Tissue Culture, Part 2*, 2nd ed.. Exegetics Limited, pp. 639-651 (1993/1996).

Godfrey et al., "Phospholipid and Arachidonic Acid Metabolism in Zymosan-Stimulated Human Monocytes: Modulation by cAMP," *Journal of Cellular Physiology* 131, pp. 384-392 (1987).

Guern, et al., "The Compartmentation of Secondary Metabolites in Plant Cell Cultures." In *Cell Culture and Somatic Genetics of Plants*, vol. 4, Constabel, et al. (eds.). Academic Press, New York, pp. 43-76 (1987).

Hamberg, et al., "Oxylipin Pathway to Jasmonates: Biochemistry and Biological Significance," *Biochimica et Biophysica Acta.* 1165, pp. 1-18 (1992).

Jia, et al., "Taxanes from *Taxus chinensis* I," *Chinese Science Bulletin* 36, pp. 1174-1177 (1991).

Jia, et al., "Taxanes from *Taxus chinensis* III," *Chinese Science Bulletin* 36, pp. 1967-1969 (1991).

Koda, "The Role of Jasmonic Acid and Related Compounds in the Regulation of Plant Development," *International Review of Cytology* 135, pp. 155-199 (1992).

Leroyer, et al., "Chemiluminescence and Oxygen Radical Generation by Walker Carcinosarcoma Cells following Chemotactic Stimulation," *Cancer Research* 47, pp. 4771-4775 (1987).

McKeon, et al., "Biosynthesis and Metabolism of Ethylene," In *Plant Hormones: Physiology, Biochemistry and Molecular Biology*, 2nd ed., Davies (ed.). Kluwer Academic Publishers, pp. 118-139 (1995).

Meyer, et al., "Occurrence of the Plant Growth Regulator Jasmonic Acid in Plants," *Journal of Plant Growth Regulation* 3, pp. 1-8 (1984).

Mirjalili, et al., "Methyl Jasmonate Induced Production of Taxol in Suspension Cultures of *Taxus cuspidata:* Ethylene Interaction and Induction Models," *Biotechnology Progress* 12(1), pp. 110-118 (1996).

Morandi, "Effect of Xenobiotics on Endomycorrhizal Infection and Isoflavonoid Accumulation in Soybean Roots," *Plant Physiol. Biochem.* 27(5), pp. 697-701 (1989).

Omata et al., "Volatile Components of Ginger Flowers Hedychium-Coronarium Koenig," *Flavour and Fragrance J.* 6(3), pp. 217-220 (1991).

Parthier, "Jasmonates: Hormonal Regulators or Stress Factors in Leaf Senescence?," *J. of Plant Growth Regulation* 9, pp. 57-63 (1990).

Parthier, "Jasmonates, New Regulators of Plant Growth and Development: Many Facts and Few Hypotheses on their Actions," *Bot. Acta* 104, pp. 446-454 (1991).

Ravnikar, et al., "Stimulatory Effects of Jasmonic Acid on Potato Stem Node and Protoplast Culture," *J. Plant Growth Regulation* 11, pp. 29-33 (1992).

Sakuta, et al., "Cell Growth and Accumulation of Secondary Metabolites," In *Cell Culture and Somatic Genetics of Plants*, vol. 4, Constabel, et al. (eds.). Academic Press, New York, pp. 97-114 (1987).

Sembdner, et al., "The Biochemistry and the Physiological and Molecular Actions of Jasmonates," *Annu. Rev. Plant Physiol. Plant Mol. Biol.* 44, pp. 569-589 (1993).

Seto, et al., "Structure-Activity Relationships of (±)-Cucurbic Acid Analogs on the Root Growth of Rice Seedlings and Height of Young Corn Plants," *J. Pesticide Sci.* 17, pp. 61-67 (1992).

Staswick, "Jasmonates, Salicylic acid and Brassinoldes" and "Jasmonate Activity in Plants." In *Plant Hormones: Physiology, Biochemistry and Molecular Biology*, 2nd ed., Davies (ed.). Kluwer Academic Publishers, pp. 179-187 (1995).

Threlfall, et al., "The use of biotic and abiotic elicitors to induce the formation of secondary plant products in cell suspension cultures of solanaceous plants," *Biochemical Society Transactions* 16, pp. 71-75 (1988).

Vick, et al., "Oxidative Systems for Modification of Fatty Acids: The Lipoxygenase Pathway," In *The Biochemistry of Plants*, vol. 9, Stumpf, et al. (eds.). Academic press, New York, pp. 53-89 (1987).

Walker-Simmons, et al., "Proteinase Inhibitor I Accumulation in Tomato Suspension Cultures," *Plant Physiol.* 80, pp. 68-71 (1986).

Wang, et al., "Enhanced Production of Taxol in Suspension Cultures of Taxus chinensis by Controlling Inoculum Size," *Biotechnology Letters* 19(4), pp. 353-355 (1997).

Wink, "Physiology of the Accmulation of Secondary Metabolites with Special Reference to Alkaloids." In *Cell Culture and Somatic Genetics of Plants*, vol. 4, Constabel, et al. (eds.) Academic Press, New York, pp. 17-42 (1987).

Xu, et al., "Determination of taxol in the extract of *Taxus chinensis* by reversed phase HPLC," *Chemical Abstracts* 112(1), Abstr. 3779c (Jan. 1, 1990).

Xu, et al., "Determination of taxol in *Taxus chinensis* by HPLC method," *Chemical Abstracts* 116(13), Abstr. 124148n (Mar. 30, 1992).

Xu, et al., "Plant Defense Genes are Synergistically Induced by Ethylene and Mehtyl Jasmonate," *The Plant Cell* 6, pp. 1077-1085 (1994).

Yamane, et al., "Synthesis of Jasmonic Acid Related Compounds and Their Structure-Activity Relationships on the Growth of Rice Seedings," *Agric. Biol. Chem.* 44(12), pp. 2857-2864 (1980).

Yukimune, et al., "Methyl Jasmonate-Indicued Overproduction of Paclitaxel and Baccatin III in *Taxus* Cell Suspension Cultures," *Nature Biotechnology* 14(9), pp. 1129-1132 (1996).

Asada, et al., "Stimulation of Ajmalicine Production and Excretion from *Catharanthus roseus:* Effects of adsorption in situ, Elicitors, and Alginate Immobilization," *Appl. Microbiol. Biotechnol.* 30, pp. 475-382 (1989).

Beaumont, et al., "Effects of Immobilizing Agents and Procedures on Viability of Cultured Celery (*Apium greveolens*) Cells," *Biotechnol. Lett.* 9, pp. 377-382 (1987).

Berlin, et al., "Formation of Mono-and Diterpenoids by Cultured Cells of *Thuja Occidentalis,*" *Phytochemistry* 27, pp. 127-132 (1988).

Bornman, "Possibilities and Constraints in the Regneration of Trees from Cotyledonary Needles of *Picea abies* in vitro," *Physiol. Plant.* 57, pp. 5-16 (1983).

Darvill, et al., "Phytoalexins and their Elicitors-A Defense Against Microbial Infection in Plants," *Ann. Rev. Plant Physiol.* 35, pp. 243-275 (1984).

Delfel, et al., "Antiumor Alkaloids in Callus Cultures of *Cephalotaxus harringtonia,"* *Phytochemistry* 16, pp. 1595-1598 (1977).

Ebel, "Induction of Phytoalexin Synthesis in Plants Following Microbial Infection or Treatment with Elicitors," *Bioregulators: Chemistry and Uses.* American Chemical Society, pp. 257-271 (1984).

Eilert, "Elicitation: Methodology and Aspects of Application." In *Cell Culture and Somatic Genetics of Plants*, vol. 4, Constabel, et al. (eds.). Academic Press, New York, pp. 153-196 (1987).

Heinstein, "Future Approaches to the Formation of Secondary Natural Products in Plant Cell Suspension Cultures," *Journal of Natural Products* 48, pp. 1-9 (1985).

Jaziri, et al., "Enzyme-linked Immunosorbent Assay for the Detection and the Semi-Quantitative Determination of Taxane Diterpenoids Related to Taxol in Taxus sp. and Tissue Cultures," *J Pharm. Belg.* 46, pp. 93-99 (1991).

Miyasaka, et al., "Regulation of Ferruginol and Cryptotanshinone Biosynthesis in Cell Suspension Cultures of *Salvia Miltiorrhiza,"* *Phytochemistry* 25, pp. 637-640 (1986).

Robins, et al., "The Stimulation of Anthraquinone Production by *Cinchona ledgeriana* Cultures with Polymeric Adsorbents," *Appl. Microbiol. Biotechnol.* 24, pp. 35-41 (1986).

Van Uden, et al., "The Accumulation of Podophyllotoxin-β-D-glucoside by Cell Suspension Cultures Derived form the Conifer *Callitris drummondii,"* *Plant Cell Reports* 9, pp. 257-260 (1990).

Westgate, et al., "Growth of *Cephalotaxus harringtonia* Plant Cell-Cultures," *Appl. Microbial. Biotechnol.* 34, 798-803 (1991).

Wickeramesinhe, et al., "Habituated Callus Cultures of *Taxus media* cultivar Hicksii as a Source for Taxol" (Abstract), *Plant Physiol.* 96 (Suppl.), p. 97 (1991).

Witherup, et al., "*Taxus* spp. Needles Contain Amounts of Taxol Comparable to the Bark of *Taxus brevifolia:* Analysis and Isolation," *Journal of Natural Products* 53, pp. 1249-1255 (1990).

Xu, et al., "Determination of Taxol in *Taxus chinensis* by HPLC Method," *Acta Pharmeceutica Sinica* 26, pp. 537-540 (1991).

Shetty, K. et al., "Growth Kinetics and Phenolics Production in Glycine Max Cell Suspension Cultures" *Applied Biochemistry and Biotechnology,* vol. 20/21 (1989), pp. 825-843.

Reid MS, "The Functioning of Hormones in Plant Growth and Development: Ethylene in Plant Growth, Development, and Senescence," in Davies, ed., *Plant Hormones and their Role in Plant Growth and Development,* Martinus Nijhoff Publishers (1987), pp. 257-279.

Doares SH, et al., "Oligogalacturonides and chitosan activate plant defensive genes through the octadecanoid pathway," *Proc. Natl. Acad. Sci. USA,* vol. 92, pp. 4095-4098, (1995).

Veen H., "Silver Thiosulphate: An Experimental Tool in Plant Science," *Scientia Horticulturae,* 20, pp. 211-224 (1983).

Yoshikawa M, "Diverse modes of action of biotic and abiotic phytoalexin elicitors", *Nature* 275, pp. 546-547 (1978).

Dahiya JS, et al., "Phytoalexin accumulation in plant tissues of *Brassica* spp. in response to abiotic elicitors and infection with *Leptosphaeria maculans,"* Bott. Bull. Academia Sinica 30: 107-115 (1989).

Galston, A.W. et al., "Polyamines as Endogenous Growth Regulators," in Davies, ed., *Plant Hormones: Physiology, Biochemistry and Molecular Biology,* Kluwer Academic Publishers (1995), p. 171.

Baker JE, "Preservation of Cut Flowers," in Nickell, ed., *Plant Growth Regulating Chemicals,* vol. II, CRC Press (1983) pp. 178-191.

Dodds, John H., et al., "Nutritional Components of Tissue Culture Media," *Experiments in Plant Tissue Culture,* Cambridge University Press, USA (1982).

Fujita, Masayuki, et al., "Induction of Phytochelatin and Variation of Glutathione Level in Fruits and Callus Cultures of Pumpkin by Treatment with Heavey Metals," *Journal of the Food Hygrenic Society of Japan,* 34(5):404-408 (1990).

Maity, Anuradha, et al., "Induction of Phytoalexin in Ricebean (*Vigna umbellata*) by Abiotic and Biotic Elicitors and its Modulation by Elevated Temperature," *J. Mycopathol. Res.,* 32(1):19-27 (1994).

Berlin, Jochen, et al., "Formation of Benzophenanthridine Alkaloids by Suspension Cultures of *Eschscholtzia californica," Z. Naturforsch,* 38c:346-352 (1983).

Kreis, Wolfgang, et al., The Production of Secondary Metabolites by Plant Cells Cultivated in Bioreactors, *Planta Medica* 55, pp. 409-416 (1989).

Payne, G.F., et al., *Plant Cell and Tissue Culture in Liquid Systems,* Chapter 6: Suspension Culture, pp. 147-176, John Wiley & Sons, Inc. (1993).

Xu, L.X.. et al., "Determination of Taxol in the Extract of *Taxus Chinensis* by Reversed Phase HPLC," ACTA Pharmaceutica Sinica, 24(7):552-555 (1989).

Payne, G., et al., "Plant Cell and Tissue Culture in Liquid System", 62-66 & 298-297 (Hanser Publishers 1991).

Di, C.K., et al., "Primary Research on Production of Callus From *Taxus chinensis* var. *mairei,* " Abstract from Annual Meeting of Beijing Plant Physiology Society (1991).

Yamakawa, T., et al., "Production of Anthocyanins by *Vitis Cells* in Suspension Culture," Agric. Biol. Chem., 47(10):2185-2191 (1983).

Robins, R.J. and M.J.C. Rhodes, "The Stimulation of Anthraquinone Production by *Cinchona ledgeriana* Cultures with Polymeric Adsorbents," Appl. Microbiol. Biotechnol., 24:35-41 (1986).

"Plant and Animals Cells: Process Possibilities", 29-30 (C. Webb and F. Mavituna eds., Ellis Horwood Limited 1987).

Kim, D., et al., "Two Stage Cultures for the Production of Berberline in Cell Suspension Cultures of *Thalictrum rugosum,"* Journal of Biotechnology, 16:297-303 (1990).

5141: Jasmone, The Merck Index, 827 (Susan Budavari ed., Merck & Co., Inc. 11th ed. 1989).

Toder, B.H., et al., "Regiospecific Methylation of Cyclopentenone Derivatives, " Synthetic Communications, 5(6):435-439 (1975).

The Difco Manual, Section VI: Peptones & Hydrolysates Selection Guide, 829, (11th ed.).

Cormier, F., et al., "Effects of Sucrose Concentration on the Accumulation of Anthocyanins in Grape (*Vitis vinifera*) Cell Suspension," Can. J. Bot. 68:1822-1825 (1990).

Fujita, Y. and Y. Hara, "The Effective Production of Shikonin by Cultures with an Increased Cell Population," Agric. Biol. Chem., 49(7):2071-2075 (1985).

Matsurbara, K., et al., "High Density Culture of *Coptis japonica* Cells Increases Berberine Production," J. Chem. Tech. Biotechnol. 46:61-69 (1989).

Mantell, S.H., et al., "The Effect of Initial Phospate and Sucrose Levels on Nicotine Accumulation in Batch Suspension Cultures of *Nicotiana tabacum* L., " Plant Cell Reports, 2:73-77 (Springer-Verlag 1983).

Yeoman, M.M, et al., "Accumulation of Secondary Products as a Facet of Differentiation in Plant Cell and Tissue Culture", Differentiation In Vitro, The Fourth Symposium of the British Society for Cell Biology, 65-82 (Cambridge University Press 1982).

Moore, T.C., Biochemistry and Physiology of Plant Hormones, 33-39, (Springer-Verlag New York Inc., 2nd ed. 1989).

George, E.F., et al., Plant Culture Media, vol. 1: Formulations and Uses, 427-441 & Tabel 1 (Exegetics Ltd. 1987).

Wysokinska, H. and L. Swlatek, "Production of Iridoid Glucosides in Cell Suspension Cultures of *Penstemon Serrulatus*. Effects of Nutritional Factors," Plant Science, 76:249-258 (1991).

Yun, J.W., et al., "Optimizations of Carotenoid Biosynthesis by Controlling Sucrose Concentration," Biotechnology Letters, 12(12):905-910 (1990).

Schiel, O., et al., "Increased Formation of Cinnamoyl Putrescines by Fedbatch Fermentation of Cell Suspension Cultures of *Nicotiana tabacum*" Plant Cell Reports, 3:18-20 (1984).

Miyasaka, H., et al., "Effect of Nutritional Factors on Cryptotanshinone and Ferruginol Production by Cell Suspension Cultures of *Salvia miltiorrhiza*," Phytochemistry, 26(5):1421-1424 (1987).

Bramble, J.L and D.J. Graves, "Calcium and Phosphate Effects on Growth and Alkaloid Production in *Coffea arabica*. Experimental Results and Mathematical Model," Biotechnology and Bioengineering, 37:859-868 (1991).

Mantell, S.H. and H. Smith, "Cultural Factors That Influence Secondary Metabolite Accumulation in Plant Cell and Tissue Cultures," Plant Biotechnology, 75-108 (S.H. Mantell and H. Smith eds., Cambridge University Press 1984).

Payne, G., et al., "Plant Cell and Tissue Culture in Liquid Systems," 49-70 (Hansen Publishers 1992).

Fett-Neto, A.G., et al., "Kinetics of Taxol Production, Growth, and Nutrient Uptake in Cell Suspensions of *Taxus cuspidata*," Biotechnology and Bioengineering, 44:205-210 (1994).

Srinivasan, V., et al., "Taxol Production in Bioreactors: Kinetics of Biomass Accumulation, Nutrient Uptake, and Taxol Production by Cell Suspensions of *Taxus baccata*," Biotechnology and Bioengineering, 47:666-676 (1995).

Hezari, M., "Taxol Production and Taxadiene Synthase Activity in *Taxus canadensis* Cell Suspension Cultures," Archives of Biochemistry and Biophysics, 337(2):185-190, (1997).

Mei, X., et al., "Kinetics of Taxol Biosynthesis in Biorectors," Med. Chem. Res., 6:256-263 (1996).

Taiz, L. and E. Zeiger, "Water and Plant Cells," Plant Physiology, 61 (The Benjamin/Cummings Publishing Company, Inc. 1991).

Dougall, D.K., "Chemicals from Plant Cell Cultures: Yields and Variation," Biotechnology in Plant Science: Relevance to Agriculture in the Eighties, 179-190 (Zaitlin, et al. eds., Academic Press, Inc. 1985).

Dougall, D.K. and K.W. Weyrauch, "Grothw and Anthocyanin Production by Carrot Suspension Cultures Grown Under Chemostat Conditions with Phosphate as the Limiting Nutrient," Biotechnology and Bioengineering, 22(2):337-352 (1980). (Abstract).

Sahai, O.P. and M.L. Shuler, "Environmental Parameters Influencing Pheolics Production by Batch Cultures of *Nicotiana tabacum*," Biotechnology and Bioengineering, 26(2):111-120 (1984). (Abstract).

Tabata, M. and Y. Fujita, "Production of Shikonin by Plant Cell Cultures", Biotechnology in Plant Cultures, Biotechnology in Plant Science: Relevance to Agriculture in the Eighties, 207-218 (Zaitlin, et al. eds., Academic Press, Inc. 1985).

Bednarek, J., 1992, In side pocket of U.S. Appl. No. 07/874,344 - Bednarek J. et al. Steroid 21-hydroxylase is a major autoantigen involved in adult onset autoimmune Addison's disease, vol. 309, No. 1, pp. 51-55 (1992).

Berlin, 1986, From EP Opposition (47) - (D5)- Botechnology in Agriculture and Forestry 4, Ed. Y.P.S. Bajaj; Springer Verlag pp. 41-46 (1986).

Beyer, 1976, "A Potent Inhibitor of Ethylene Action in Plants," *Plant Physiol*. 58:268-271 (1976).

Blechert, et al., 1995, "The octadecanoic pathway: Signal molecules for the regulation of secondary pathways," *Proc. Natl. Acad. Sci. USA* vol. 92, pp. 4099-4105, May 1995.

Bodnaryk, 1994, "Potent effect of jasmonates on indole glucosinolates in oilseed rape and mustard," *Phytochemistry* 35(2): 301-05 (1994).

Bohlmann et al., 1991, "Thionins," *Annu. Rev. Plant. Physiol. Plant Mol. Biol*. 42:227-40 (1991).

Cassab et al., 1988, "Cell Wall Proteins," *Ann. Rev. Plant. Physiol. Plant Mol. Biol*. 39:321-53 (1988).

Chi et al., 1989, "Ethylene Inhibitors Enhanced de novo shoot regeneration from cotyledons of *Brassica campestris* ssp. *chinensis* (chinese cabbage) in vitro," *Plant Science* 64:243-250 (1989).

Chraibi et al., 1991, "Stimulation of shoot regeneration from cotyledons of *Helianthus annuus* by the ethylene inhibitors, silver and colbalt," *Plant Cell Reports* 10:204-207 (1991).

Cohen et al., 1993, "Local and Systemic Protection Against *Phytophthora infestans* Induced in Potato and Tomato Plants by Jasmonic Acid and Jamonic Methyl Ester," Phytopathology 83:1054-62 (1993).

Conconi, et al., 1996, "Intracellular Levels of Free Linolenic and Linoleic Acids Increase in Tomato Leaves in Response to Wounding," *Plant Physiol*. (1996) 111:797-803.

Creelman, et al., 1992, "Jasmonic acid/methyl jasmonate accumulate in wounded soybean hypocotyls and modulate wound gene expression," *Proc. Natl. Acad. Sci USA* vol. 89, pp. 4938-4941, Jun. 1992.

Dixon et al., 1994, "Early Events in the Activation of Plant Defense Responses," *Annu. Rev. Phytopathol*. 32:479-501 (1994).

Doares, et al., , 1995, "Salicylic Acid Inhibits Synthesis of Proteinase Inhibitors in Tomato Leaves Induced by Systemin and Jasmonic Acid," *Plant Physiol*. (1995) 108:1741-1746.

Farmer, et al., 1994, "Diethyldithiocarbamic Acid Inhibits the Octadecanoid Signaling Pathway for the Wound Induction of Proteinase Inhibitors in Tomato Leaves," *Plant Physiol*. (1994) 106:337-342.

Gibson, et al., 1991, "Establishment of cell cultures of taxus brevifolia for taxol and ecdysone production," *Suppl. To Plant Physiology* 96(1):603 (1991).

Glick, *Glossary of Biochemistry and Molecular Biology* , Raven Press, New York.

Halitschke et al., 2001, "Molecular Interactions between the Specialist Herbivore *Manduca Sexta* (Lepidoptera, Sphingidae) and its Natural Host *Nicotiana attenuata*. III. Fatty Acid-Amino Acid Conjugates in Herbivore Oral Secretions Are Necessary and Sufficient for Herbicore-Specific Plant Responses," *Plant Physiol*. 125:711-717 (Feb. 2001).

Lau et al., 1976, "Inhibitors of Ethylene Production by Cobaltous Ion," *Plant Physiol*. 58:114-117 (1976).

Li et al., 1994, From U.S. Appl. No. 07/874,344 Feb. 16, 1994 Response - for T. chinesis not similar to T. brevifolia/isolating taxanes from T. chinensis - Li et al., Three new diterpenoids from Taxus chinensis, Chem. Pharm. Bull., 41(9) 1672-1673 (1993).

Lieberman, 1979, "Biosynthesis and Action of Ethylene," *Ann. Rev. Plant. Physiol*. 30:533-91 (1979).

Lighter, et al., 1993, "Isolation of signaling mutants of tomato (Lycopersicon esculentum)," *Mol. Gen. Genet*. (1993) 241:595-601.

Mattiacci et al., 1995, "β-Glucosidasse: An elicitor of herbivore-induced plant odor that attracts host-searching parasitic wasps," *Proc. Natl. Acad. Sci. USA* 92:2036-2040 (Mar. 1995).

McGurl, et al., "Polypeptide signalling for plant defence genes," *Biochem. Soc. Symp*. 60, 149-154.

Mohr, et al., "Biological Catalysis," *Plant Physiology* pp. 67, Springer.

Moura, et al., 2001, "Wound-Inducible Proteinase Inhibitors in Pepper. Differential Regulation upon Wounding, Systemin, and Methyl Jasmonate," *Plant Physiology*, May 2001, vol. 126, pp. 289-298.

Narcaez-Vasquez, et al., 1994, "A Sulfhydryl Reagent Modulates Systemic Signaling for Wound-Induced and Systemin-Induced Proteinase Inhibitor Synthesis," *Plant Physiol*. (1994) 105:725-730.

Orozco-Cardenas, et al., 2001, "Hydrogen Peroxide Acts as a Second Messenger for the Induction of Defense Genes in Tomato Plants in Response to Wounding, Systemin, and Methyl Jasmonate," *The Plant Cell*, vol. 13, 179-191, Jan. 2001.

Pena-Cortes, et al., 1993, "Aspirin prevents wound-induced gene expression in tomato leaves by blocking jasmonic acid biosynthesis," *Planta* (1993) 191:123-128.

Piel et al., 1997, "Cullulysin from the plant parasitic fungus *Trichoderma viride* eleicits volatile biosyntheis in higher plants via the octadecanoid signalling cascade," *FEBS Letters* ; 416:143-148 (1997).

Purnhauser et al., 1986, "Stimulation of shoot regeneration in *Triticum aestivum* and *Nicotiana plumbaginifolia* Viv. tissue cultures using the ethylene inhibitor $AgNO_3$," *Plant Cell Reports* 6:1-4 (1987).

Reid, 1987, "Plant Hormones and Their Role in Plant Growth and Development," 1987, pp. 260-261, 269-271.

Roustan et al, 1989, "Stimulation of *Daucus carota* somatic embryogenesis by inhibitors of ethylene synthesis: cobalt and nickel," *Plant Cell Reports* 8:182-185 (1989).

Ryan, 1992, "The search for the proteinase inhibitor-inducing factor, PIIF," *Plant Molecular Biology* 19:123-133, 1992.

Ryan, 2000, "The systemin signaling pathway: differential activation of plant defensive genes," *Biochimica et Biophysica Acta* 1477 (2000) 122-121.

Ryan, et al., 1998, "Systemin: A Polypeptide Signal for Plant Defensive Genes," *Annu. Rev. Cell Dev. Biol*. 1998, 14:1-17.

Sargent, 1996, "Re: Ethylene question," at http://plant-tc.coafes.umn.edu/listserv/1996/log9605/msg00116.html (posted Jun. 1, 1996) (visited Jul. 17, 2003).

Seibert and Kadkade, 1980, - from EP Opposition (47) - (D7) Seibert and Kadkade, Light. In "Plant Tissue Culture as a Source of Biochemicals" EJ Staba (ed) CRC Press, Boca Raton, Floride pp. 123-141 (1980).

Seabrook, 1980, from EP Opposition (47) - Plant Tissue Culture as a Source of Biochemicals, Ed. E. John Staba; CRC Press Inc 1980 pp. 1-6.

Songstad et al., 1988, "Effect of 1-aminocyclopropane-1-carboxylic acid, silver nitrate, and norbornadiene on plant regeneration from maize callus cultures," *Plant Cell Reports* , 7:262-265 (1988).

Staswick, 1992, "Jasmonate, Genes, and Frangrant Signals," *Plant Physiol*. 99, 804-807.

Stenesh, Dictionary of Biochemistry and Molecular Biology, Wiley Interscience Publication .

Stratmann, et al., 2000, "UVB/UVA Radiation Activates a 48 kDa Myelin Basic Protein Kinase and Potentiates Wound Signaling in Tomaoto Leaves," *Photochemistry and Photobiology*, 2000, 71(2): 116-123.

Vain et al., 1989, "Enhancement of production and regeneration of embryogenic type II callus in *Zea mays* L. by $AgNO_3$," *Plant Cell, Tissue and Organ Culture* 18:143-151 (1989).

Vasil, 1984, "Clonal Progagation: Adventitious Buds," *Cell Culture and Somatic Cell Genetics of Plants*, Vasil, I. ed., 1:53 (1984).

Vick et al., 1984, "Biosynthesis of Jasmonic Acid by Several Plant Species," *Plant Physiol*. (1984) 75, 458-461.

Vidensek, N. et al, 1994, From U.S. Appl. No. 7/874,344 Feb. 16, 1994 Response - for amount of dry weight Taxol from T. brevifolia - Vidensek, N. et al. Taxol content in bark, wood, root, leaf, twig and seeding from serveral Taxus species, J. Nat. Prod. 53(6), pp. 1609-1610 (1990).

Walling, 2000, "The Myriad Plant Responses to Herbivores," *J. Plant Growth Regul*. 19:195-216 (2000).

Ward et al., 1999, "Structural requirements for biology active jasmonates: Induction of protease inhibitors and coyledon senescence," *Plant Growth Regulation* 27:49-56 (1999).

Yang et al., 1984, "Ethylene Biosynthesis and Its Regulation in Higher Plants," *Ann. Rev. Plant Physiol*. 35:155-89 (1984).

Zhu, Wei Hua et al., *Chinese Medicine*, vol. 14, No. 9, (Sep. 1991).

| COMPOUND | DAY 25 | | | DAY 42 | | |
|---|---|---|---|---|---|---|
| | % D. W. | mg/L | % Extracellular | % D. W. | mg/L | % Extracellular |
| 10-Deacetylbaccatin III | 0.0000 | 0.00 | | 0.0000 | 0.00 | |
| Baccatin III | 0.0184 | 10.43 | 10.57 | 0.0420 | 19.83 | 14.72 |
| 7-Xylosyl-10-deacetyltaxol | 0.0127 | 7.19 | 24.62 | 0.0283 | 13.38 | 45.81 |
| 10-deacetyltaxol | 0.0122 | 6.95 | 17.37 | 0.0127 | 5.99 | 0.00 |
| Cephalomannine | 0.0000 | 0.00 | | 0.0119 | 5.60 | 86.02 |
| 10-deacetyl-7-epitaxol | 0.0081 | 4.61 | 62.42 | 0.0275 | 12.99 | 72.59 |
| Taxol | 0.0427 | 24.25 | 70.95 | 0.3244 | 153.34 | 87.52 |
| 7-Epitaxol | 0.0122 | 6.92 | 84.61 | 0.0154 | 7.26 | 85.28 |
| TOTAL-Unknown | 0.0452 | 25.67 | | 0.1625 | 76.83 | |
| TOTAL Taxanes | 0.1515 | 86.84 | | 0.6245 | 295.23 | |

FIG. 5A

ENHANCED PRODUCTION OF TAXOL AND TAXANES BY CELL CULTURES OF *TAXUS* SPECIES

This application is a continuation-in-part of International application PCT/US97/08907, designating the U.S., filed May 27, 1997, which is a continuation of Ser. No. 08/653,036, filed May 24, 1996, now abandoned. This application is also a continuation-in-part of U.S. Ser. No. 08/653,036, filed May 24, 1996, now abandoned, which is a continuation-in-part of U.S. Ser. No. 08/370,494, filed Jan. 9, 1995, now abandoned, which is a divisional of U.S. Ser. No. 07/874,344, filed Apr. 24, 1992, now U.S. Pat. No. 5,407,816, which is a continuation-in-part of U.S. Ser. No. 07/839,144, filed Feb. 20, 1992, now abandoned. The text of each priority application is expressly incorporated herein by reference to the extent that the text of the respective priority application differs from this application.

BACKGROUND OF THE INVENTION

A. Field of the Invention

This invention is directed to methods for the enhanced production and recovery of taxol, baccatin III and other taxanes by cell cultures of *Taxus* species.

B. Related Art

The Taxane Supply Challenge

Taxol is a diterpenoid alkaloid originally isolated from the bark of the pacific yew, *Taxus brevifolia* (Wani, et al. 1971, *J. Am. Chem. Soc.*, 93, 2325-2327). Interest in taxol began when the National Cancer Institute (NCI), in a large-scale screening program, found that crude bark extracts exhibited anti-tumor activities. Since then, clinical trials have confirmed that taxol is extremely effective against refractory ovarian cancers, and against breast and other cancers. Taxol has been pronounced as a breakthrough in chemotherapy because of its fundamentally different mechanism of cytotoxicity, i.e., by inhibiting depolymerization of microtubules (see Rowinsky, et al., 1990, *J. Natl. Cancer Inst.*, 82, 1247-1259).

A daunting variable in the taxol equation has been supply. Bark-derived taxol has been discontinued as the primary source of commercial drug; large-scale production has been achieved by semi-synthesis, i.e., chemical attachment of a side chain to the plant-derived precursor, 10-deacetylbaccatin III. Total synthesis, while accomplished by academic laboratories, shows little promise as a viable commercial route to taxol. There is therefore an urgent need to develop cost-effective, environmentally-benign, and consistent sources of supply to keep up with the growing demand for taxol.

In addition to taxol, there is an urgent need to develop processes for the commercial production of related taxane molecules. Derivatives of taxol such as Taxotere have already been introduced into the world market. Further, tremendous research activity is being focused on the discovery and development of novel taxane derivatives with advantageous activity. These advances are likely to create an ongoing need for large quantities of an appropriate starting "skeleton" molecule from which any given derivative could be effectively synthesized.

One example of such a molecule is the aforementioned precursor, 10-deacetylbaccatin III, which is used as the starting point for semi-synthetic taxol. Another desirable starting molecule for semi-synthetic production of taxol and other derivatives is baccatin III. Baccatin III is normally not accumulated as a major taxane in planta, and hence there is no facile large-scale natural source for this molecule. However, it is a very desirable starting point for semi-synthesis because of its chemical closeness to taxol; for example, the steps that are required for acetylation of the 10 position of 10-deacetylbaccatin III are circumvented if baccatin III is the starting point rather than 10-deacetylbaccatin III.

This invention is related to the development of plant cell culture-based processes for the commercial production of taxol, baccatin III and other taxanes.

Tissue Cultures as a Source of Plant-Derived Chemicals

The ability of plant cells to divide, grow, and produce secondary metabolites under a variety of different cultural regimes has been amply demonstrated by a number of groups. At present, two compounds, shikonin (a red dye and anti-inflammatory) and ginsengoside (a tonic in oriental medicine) are produced by tissue-culture processes in Japan. Many other processes are reportedly close to commercialization, including vanillin, berberine and rosmarinic acid (see Payne, et al. 1991, "Plant Cell and Tissue Culture in Liquid Systems," Hanser Publishers, Munich).

The advantages of a plant cell culture process for taxol, baccatin III, and taxanes are many: (i) A cell culture process ensures a limitless, continuous and uniform supply of product, and is not subject to pests, disasters and seasonal fluctuations, (ii) cell cultures can be cultivated in large bioreactors, and can be induced to overproduce the compound of interest by manipulating environmental conditions, (iii) cell cultures produce a simpler spectrum of compounds compared to bark or needles, considerably simplifying separation and purification, (iv) a cell culture process can adapt quickly to rapid changes in demand better than agriculture-based processes, (v) besides supplying taxol, baccatin III or other precursors, a cell culture process could also produce taxane compounds that exhibit advantageous bioactivity profiles, or that could be converted into other bioactive derivatives.

Since aseptic, large-scale, plant cell cultivation is inherently expensive, a cell culture process becomes commercially relevant only when these costs are offset by high productivity. Every plant species and target metabolite is different, and different approaches are necessary for every particular system. This invention focuses on creative and skilled approaches for obtaining highly productive plant cell cultures for taxol, baccatin III, and taxane production.

Problems with Tissue Cultures of Woody Plants and Conifers

A historical survey of the literature suggests that whereas herbaceous plants have been relatively easily manipulated in culture, productive cultures of woody plants and conifers have been achieved only with difficulty.

The growth of secondary metabolite producing gymnosperm- and conifer-cultures have been generally low. For example, Berlin and Witte, (1988, *Phytochemistry*, 27, 127-132) found that cultures of *Thuja occidentalis* increased their biomass by only ca. 30% in 18 days. Van Uden et al. (1990, *Plant Cell Reports*, 9, 257-260) reported a biomass increase of 20-50% in 21 days for suspensions of *Callitris drummondii*. Westgate et al. (1991, *Appl. Microbiol. Biotechnol.*, 34, 798-803) reported a doubling time of ca. 10 days for suspensions of the gymnosperm, *Cephalotaxus harringtonia*. As summarized by Bornman (1983, *Physiol. Plant.* 57, 5-16), a tremendous amount of effort has been directed towards medium development for spruce suspensions (*Picea abies*). This collective work demonstrates that gymnosperm suspensions are indeed capable of rapid growth, but that no generalities can be applied, and that media formulations for different cell lines must be optimized independently.

A survey of secondary metabolite productivity among gymnosperm cultures also points to the difficulty of inducing rapid biosynthesis compared to herbaceous species. For example, cultures of *Cephalotaxus harringtonia* produced terpene alkaloids at a level of only 1% to 3% of that found in the parent plant (Delfel and Rothfus, 1977, *Phytochemistry,* 16, 1595-1598). Even upon successful elicitation, Heinstein (1985, *Journal of Natural Products,* 48, 1-9) was only able to approach the levels produced in the parent plant (ca. 0.04% dry weight total alkaloids). Van Uden et al (1990) were able to induce suspension cultures of the conifer *Callitris drummondii* to produce podophyllotoxin, but only at levels one tenth of that produced by the needles. The ability of *Thuja occidentalis* to produce significant levels of monoterpenes (10-20 mg/L) and the diterpenoid dehydroferruginol (2-8 mg/L) has been convincingly demonstrated by Berlin et al. (1988). However, these results were obtained with a slow-growing (30% biomass increase in 18 days) and low cell density (5 to 7 grams dry weight per liter) culture.

Cell Culture for Taxane Production

The difficulties in achieving rapid growth and high productivity encountered in gymnosperm-suspensions have generally been reflected in the reports so far on taxane production in *Taxus* cell cultures.

Jaziri et al. (1991, *J Pharm. Belg.,* 46, 93-99) recently initiated callus cultures of *Taxus baccata,* but were unable to detect any taxol using their immunosorbent assay. Wickremesinhe and Arteca (1991, Plant Physiol., 96, (Supplement) p. 97) reported the presence of 0.009% dry weight taxol in callus cultures of *Taxus media* (cv. hicksii), but details on the doubling times, cell densities, and the time-scale over which the reported taxol was produced, were not indicated.

U.S. Pat. No. 5,019,504 (Christen et al. 1991) describes the production and recovery of taxane and taxane-like compounds by cell cultures of *Taxus brevifolia.* These workers reported taxol production at a level of 1 to 3 mg/L in a two- to four-week time frame. They also reported a cell mass increase of "5-10 times in 3-4 weeks", which corresponds to doubling times of ca. 7 to 12 days.

Significant increases in taxane titers and volumetric productivity are required before an economically-viable plant cell culture process for taxane production can supply the projected annual demand of many hundreds of kilograms per year.

SUMMARY OF THE INVENTION

The objects of this invention include the formulation of special environmental conditions to foster rapid growth, high cell densities, and high cell viabilities. (The growth characteristics reported in this study surpass previous results by a significant factor.)

An object of this invention is to produce taxanes at high rates by careful selection of cell lines, careful choice and manipulation of medium conditions, incorporation of enhancement agents, and careful selection of process-operating modes.

The objects of this invention include the ability to manipulate the profile of taxanes produced by altering media formulations and environmental conditions. In particular, it is an object to encourage cells to produce taxol or baccatin III as the predominant taxane product, and/or to suppress the production of the by-product cephalomannine, thereby providing an elegant biological solution to an expensive and important downstream separation and purification problem. These and other objects are met by one or more of the embodiments of this invention.

The inventors have discovered that taxol, baccatin III, and other taxol-like compounds, or taxanes, can be produced in very high yield from all known *Taxus* species, e.g., *brevifolia, canadensis, cuspidata, baccata, globosa, floridana, wallichiana, media* and *chinensis.* Further, by the methods of this invention it is possible to obtain taxol, baccatin III, and other taxanes in a much shorter time frame than previously reported. In particular, the inventors found that the species, *Taxus chinensis,* is capable of rapid growth and of producing extremely high levels of taxol, baccatin III, and taxanes within a short period of time. With the species *Taxus chinensis,* the inventors have been able to manipulate cells to yield taxol, baccatin III, and taxanes in amounts far in excess of the amounts obtained from tissue cultures of the other *Taxus* species.

Particular modifications of culture conditions (i.e., media composition and operating modes) have been discovered to enhance the yield of various taxanes from cell culture of all species of *Taxus.* Particularly preferred enhancement agents include silver ion or complex, jasmonic acid (especially the methyl ester), auxin-related growth regulators, and inhibitors of the phenylpropanoid pathway, such as 3,4-methylenedioxy-6-nitrocinnamic acid. These enhancement agents may be used alone or in combination with one another or other yield-enhancing conditions. While the yield of taxanes from plant cell culture of *T. chinensis* is particularly enhanced by use of one or more of these conditions, yield of taxanes for all *Taxus* species has been found to benefit from use of these conditions.

In one embodiment, this invention provides a method for producing taxanes in high yields in cell culture of a *Taxus* species comprising cultivating cells of a *Taxus* species in suspension culture in one or more nutrient media under growth and product formation conditions, and recovering one or more taxanes from said cells or said medium of said cell culture, or both, the cells being derived from callus or suspension cultures and the nutrient media containing an inhibitor of phenylpropanoid metabolism. Suitable inhibitors of phenylpropanoid metabolism include 3,4-methylenedioxy-6-nitrocinnamic acid, 3,4-methylenedioxycinnamic acid, 3,4-methylenedioxy-phenylpropionic acid, 3,4-methylenedioxyphenylacetic acid, 3,4-methylenedioxybenzoic acid, 3,4-trans-dimethoxycinnamic acid, 4-hydroxycinnamic acid, phenylpropiolic acid, fluorophenylalanine, 1-aminobenzotriazole, 2-hydroxy-4,6-dimethoxybenzoic acid, SKF-525A, ammonium oxalate, vinylimidazole, diethyldithiocarbamic acid, and sinapic acid.

In a preferred embodiment, at least one of the one or more nutrient media used in the method of this invention also comprises another enhancement agent which may be an inhibitor of ethylene action; jasmonic acid or an ester of jasmonic acid; or an auxin-related growth regulator. In particularly preferred embodiments, the other enhancement agent is an inhibitor of ethylene action which is a silver-containing compound, or a silver complex, or a silver ion. In another particularly preferred embodiment, the other enhancement agent is jasmonic acid or an alkyl ester thereof, and more preferably, the alkyl group esterified to jasmonic acid has from one to six carbon atoms. In an even more preferred embodiment, the enhancement agent is jasmonic acid or an alkyl ester thereof, and the medium also contains a silver-containing compound, a silver complex or silver ion. In yet another particularly preferred embodiment, the other enhancement agent is an auxin-related growth regulator, such as indoleacetic acid, picloram, α-naphthaleneacetic acid, indolebutyric acid, 2,4-dichlorophenoxyacetic acid, 3,7-dichloro-8-quinolinecarboxylic acid, or 3,6-dichloro-o-anisic acid.

In another embodiment, this invention provides a method for producing taxanes in high yields in cell culture of a *Taxus* species by cultivating cells of a *Taxus* species in suspension culture in one or more nutrient media under growth and product formation conditions, and recovering one or more taxanes from said cells or said medium of said cell culture, or both, the cells being derived from callus or suspension cultures and the nutrient media containing silver at a concentration of 900 µM or less in the form of a silver-containing compound, or a silver complex, or a silver ion, along with at least one enhancement agent which may be jasmonic acid or an ester of jasmonic acid or an auxin-related growth regulator. In a preferred embodiment, the enhancement agent is jasmonic acid or an ester of jasmonic acid, and the molar ratio of silver to enhancement agent is less than 9.5. In another preferred embodiment, the enhancement agent is an auxin-related growth regulator, and the molar ratio of silver to enhancement agent is at least 0.011.

In any of the above embodiments, the one or more nutrient media may also include a taxane precursor, which may be α-phenylalanine, β-phenylalanine, or a mixture thereof. In any of the above embodiments, the one or more nutrient media may also include glutamine, glutamic acid, aspartic acid or a mixture of these amino acids, or one or more nutrient media used in cultivation of the cells may include maltose, sucrose, glucose and/or fructose as a carbon source, preferably as the primary carbon source. In one embodiment, the nutrient medium is the same for cell culture growth and for taxol and taxane production. In an alternative embodiment, production of one or more taxanes is induced in the culture by changing the composition of the nutrient medium. In a preferred embodiment, the medium in the culture is periodically exchanged, and typically the medium exchange accomplishes periodic removal of taxanes from the culture. Preferably, cells of said *Taxus* species are cultivated by a fed-batch process.

Typically, taxol or baccatin III and/or other taxanes are recovered from said cells or said medium of said cell culture, or both. Generally, cultivation of *Taxus* species according to this invention provides an average volumetric productivity of taxanes which is at least 15 mg/L/day averaged over the period of taxane production. The average volumetric productivity of taxol is typically at least 10 mg/L/day computed for the period of taxol production. The average volumetric productivity of baccatin III is typically at least 15 mg/L/day computed for the period of taxane production.

Preferably, cells cultured according to the method of this invention are cells of *Taxus* species, and the species may be *T. brevifolia, T. canadensis, T. chinensis, T. cuspidata, T. baccata, T. globosa, T. floridana, T. wallichiana,* or *T. media.* Preferably, the cells of a *Taxus* species used in the method of this invention are cells which produce taxol above background by ELISA in callus culture or suspension culture in medium that contains no enhancement agents. More preferably, the cells of a *Taxus* species used in the method of this invention are cells which produce taxanes in suspension culture at an average volumetric productivity of 10 mg/L in a medium containing silver thiosulfate, methyl jasmonate and auxin.

DETAILED DESCRIPTION OF THE INVENTION

Figure 1:
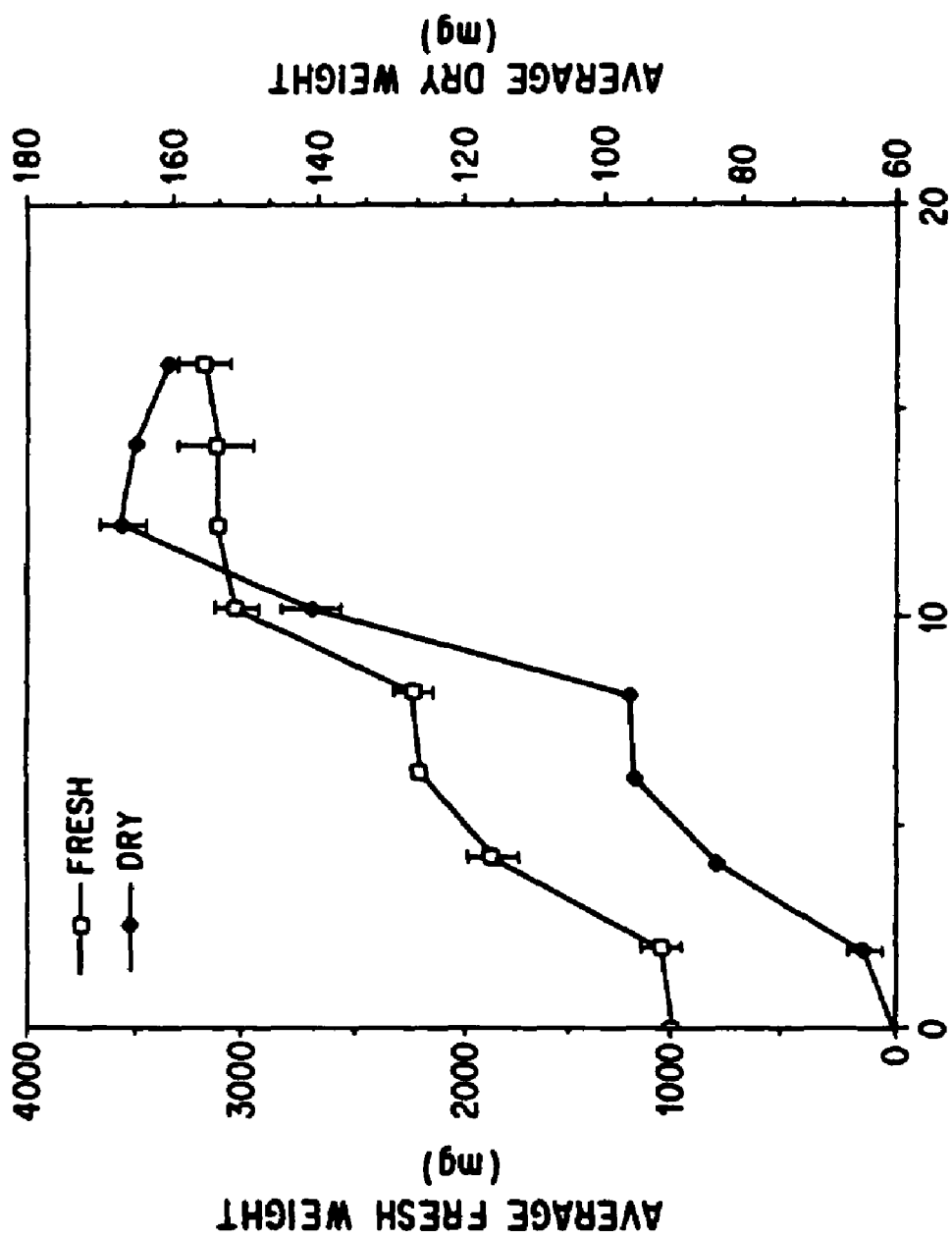
FIG. 1. Biomass increase in a *Taxus chinensis* suspension culture line K-1 over a typical batch growth cycle in Medium A. Error bars represent the standard deviation measured from duplicate flasks.

Plants have long provided important sources of pharmaceuticals and specialty chemicals. These products have typically been obtained through extraction of the harvested plant materials or by chemical synthesis. Taxol and taxanes have become one of the most important class of anticancer agents to recently emerge from the screening of natural products.

As used herein, the terms "taxol-like compounds", or "taxanes", are used interchangeably to describe a diterpenoid compound with a taxane ring. The taxanes may themselves possess antineoplastic activity, or may be modified to yield bioactive compounds. The term "total taxanes" refers to all taxanes that exhibit a characteristic UV absorbance as described in Example 5 below.

As used herein, the term "callus" is used to describe a mass of cultured plant cells that is structurally undifferentiated, and is cultivated on solidified medium. As used herein, the term "suspension culture" is used to describe structurally undifferentiated cells that are dispersed in a liquid nutrient medium. It is understood that suspension cultures comprise cells in various stages of aggregation. A range of aggregate sizes are encountered in the suspensions described in this invention, with sizes ranging from tens of microns in diameter (single cells or few-aggregated cells) to aggregates many millimeters in diameter, consisting of many thousands of cells.

The plant material useful in this invention may be obtained from any known *Taxus* species, e.g., *brevifolia, canadensis, cuspidata, baccata, globosa, floridana, wallichiana* (also referred to as *yunnanensis*), *media, fastigiata* and *chinensis* (including the synonymous species, such as *sumatrama, celebica,* and *speciosa,* and the subspecies *chinensis* var. *mairei*). In particular, the inventors have identified the species *Taxus chinensis* as capable of producing significant quantities of taxol, baccatin III, and taxanes at high volumetric productivities.

It has been found by the inventors that specific taxane content varies with plant species, and within plant species from tissue source and specific trees. Selecting a high yielding source and culture for taxane production is an important first step towards providing sufficient quantities of taxanes for therapeutic use.

Benchmarks for Commercial Relevance

A number of benchmarks may be used to gauge the commercial attractiveness and viability of a given plant-cell-culture-based process for taxane production. The benchmarks should characterize and underpin the key performance parameters of the process, including fermentation costs, the ease of downstream recovery, and the capacity of production. The benchmarks that will be described here are the broth titer and the volumetric productivity.

The broth titer is defined as the concentration of product in the whole broth, and is usually expressed as milligrams of product per liter of broth (mg/L). By definition, the whole broth titer does not distinguish between the intracellular and extracellular portions of the product. The broth titer is typically used to characterize the performance of a batch or fed-batch process. A higher broth titer implies a greater production capacity for a given reactor volume, and concomitantly, lower unit production costs. Similarly, a high-titer product is usually easier to recover in high yield, thus leading to further improvements in unit production costs.

The volumetric productivity is defined as the amount of product produced per unit reaction volume per unit time, and is commonly expressed in units of milligrams per liter per day. For the purposes of taxane production, the time scale is defined as the time frame during which production takes place at the production scale immediately preceding harvest and recovery. The volumetric productivity complements the titer as a benchmark for batch and fed-batch processes, and is particularly useful for characterizing processes where the product is removed during production, for example, by periodic medium exchange or another method of removal. A high volumetric productivity implies greater production capacity for a given reactor volume over a given time period, and concomitantly, lower unit production costs and greater overall process performance.

In certain cases the volumetric productivity is used to gauge the intrinsic capability of a biological process—for example, in the earlier stages of process development, it is useful to measure the productivity over the most productive part of the production cycle, i.e., over a short time period when the rates of biosynthesis are at their highest. This is typically referred to as the maximal instantaneous volumetric productivity. However, in gauging the performance of a process, the more appropriate benchmark is the average volumetric productivity in which the productivity is measured over the entire productive phase. Clearly, in order to achieve the highest average volumetric productivity, the maximal instantaneous productivity must be maintained through the majority of the productive phase. Unless otherwise qualified, the term volumetric productivity the average volumetric productivity, determined for the entire production phase Typically, production phase is initiated by changes in nutrient medium composition, either by replacing growth medium with production medium or by adding enhancement agents which induce a significant enhancement in taxane production.

Initiation of *Taxus* Cell Lines

*Taxus* plant material may be collected from all over North America as well as from other continents. The culture is initiated by selecting appropriate *Taxus* tissue for growth. Tissue from any part of the plant, including the bark, cambium, needles, stems, seeds, cones, and roots, may be selected for inducing callus. However, for optimum yield of taxol, needles and meristematic regions of plant parts are preferred. Most preferred are new growth needles (e.g., one to three months old), which can generally be identified by a lighter green color. The term "new growth" is broadly intended to mean plant needle production within that year's growing season.

To prevent contamination of the culture, the tissue should be surface-sterilized prior to introducing it to the culture medium. Any conventional sterilization technique, such as CLOROX (a trademark owned by the Clorox Company for bleach) treatment would be effective. In addition, antimicrobial agents such as cefoxitin, benlate, cloxacillin, ampicillin, gentamycin sulfate, and phosphomycin may be used for surface sterilization of plant material.

Callus Growth

Cultures will typically exhibit variability in growth morphology, productivity, product profiles, and other characteristics. Since individual cell lines vary in their preferences for growth medium constituents, many different growth media may be used for induction and proliferation of the callus.

The appropriate medium composition varies with the species being cultured. The preferred media for the different species are listed in Table 3. For example, although others may be used, the preferred growth nutrient media for *Taxus chinensis* are A, D, I, J, K, L, M, 0, P. These media preferably contain the ingredients listed in Table 2. Cultures are preferably carried out with medium components incorporated at the levels shown in Table 2, although the skilled artisan will recognize that some variation in these levels will not adversely affect cell growth. For example, when medium A is used, growth hormones or regulators are incorporated into the medium in an amount between 1 ppb to 10 ppm, and preferably at 2 ppb to 1 ppm. When medium D is used, the growth hormones or regulators are incorporated at levels ranging from 1 ppb to 10 ppm, and preferably at 2 ppb to 2 ppm. The amounts of other medium ingredients can be incorporated at levels ranging from $\frac{1}{10}$th the concentration to three times the concentrations indicated in Table 2.

Production of taxanes in large quantities is facilitated by cultivating *Taxus* cells in suspension culture. Generally, suspension culture can be initiated using a culture medium that was successful in callus culture. However, the requirements for suspension culture, and particularly for highly efficient production of taxanes, may be better met by modification of the medium. It has been found that when *Taxus* cells are cultured in modified culture medium and processing parameters tailored according to the method of this invention, the yield of one or more taxanes from the culture is substantially increased.

As used herein, the term "nutrient medium" is used to describe a medium that is suitable for the cultivation of plant cell callus and suspension cultures. The term "nutrient medium" is general and encompasses both "growth medium" and "production medium". The term "growth medium" is used to describe a nutrient medium that favors rapid growth of cultured cells. The term "production medium" refers to a nutrient medium that favors taxol, baccatin III, and taxane biosynthesis in cultured cells. It is understood that growth can occur in a production medium, and that production can take place in a growth medium; and that both optimum growth and production can take place in a single nutrient medium.

Suspension Growth

*Taxus* suspension cultures are capable of rapid growth rates and high cell densities like other plant cell cultures. However, optimal conditions may vary from one cell line to another, and accordingly, methods leading towards rapid optimization for any given cell line must be considered.

The cultures of various *Taxus* species are cultivated by transfer into nutrient media containing macro- and micro-nutrient salts, carbon sources, nitrogen sources, vitamins, organic acids, and natural and synthetic plant growth regulators. In particular, nutrient medium for suspension culture of *Taxus* cells will typically contain inorganic salts that supply the macronutrients calcium, magnesium, sodium, potassium, phosphate, sulfate, chloride, nitrate, and ammonium, and micronutrients such as copper, iron, manganese, molybdenum, zinc, boron, cobalt, iodine, and nickel. The medium will also typically contain vitamins such as myo-inositol, thiamine, ascorbic acid, nicotinic acid, folic acid, pyridoxine and optionally biotin, pantothenate, niacin and the like. These components may be present at concentration ranges of 1/30th to thirty times the concentrations listed in Table 2, and preferably at 1/20th to twenty times the concentrations listed in Table 2, more preferably at 1/3 to three times the concentrations listed in Table 2, and most preferably at the concentrations listed in Table 2.

The nutrient medium will also contain one or more carbon sources, and will typically contain a primary carbon source, which is defined as a source that provides over 50% of the total carbon in the nutrient medium. The primary carbon source is preferably lactose, galactose, raffinose, mannose, cellobiose, arabinose, xylose, sorbitol, or preferably glucose, fructose, sucrose or maltose. The concentration of the primary carbon source may range from 0.05% (w/v) to 10% (w/v), and preferably from 0.1% (w/v) to 8% (w/v).

The nutrient medium will also contain a nitrogen source, which, in addition to any nitrogen added in the form of macronutrient salts, will preferably be provided at least in part by an organic nitrogen source (e.g., one or more amino acids such as glutamine, glutamic acid, and aspartic acid, or protein hydrolyzates). These organic nitrogen sources may supply nitrogen at concentrations ranging from 0.1 mM to 60 mM, and preferably from 1 to 30 mM. The medium may also contain one or more organic acids such as acetate, pyruvate, citrate, oxoglutarate, succinate, fumarate, malate, and the like. These components may be included in the medium at concentrations of 0.1 mM to 30 mM, and preferably at concentrations of 0.5 mM to 20 mM.

The medium will also typically contain one or more natural or synthetic plant growth regulators, including auxin-related growth regulators such as picloram, indoleacetic acid, 1-naphthaleneacetic acid, indolebutyric acid, 2,4-dichlorophenoxyacetic acid, 3,7-dichloro-8-quinolinecarboxylic acid, 3,6-dichloro-o-anisic acid, and the like, cytokinin-related growth regulators such as $N^6$-benzyladenine, 6-[γ,γ-dimethylallylamino] purine, kinetin, zeatin, N-phenyl-N'-1,2,3-thidiazol-5-ylurea (thidiazuron) and related phenylurea derivatives and the like, gibberrellins such as $GA_3$, $GA_4$, $GA_7$, and GA derivatives, abscisic acid and its derivatives, brassinosteroids, and ethylene-related growth regulators. Additional suitable auxin-related plant growth regulators are listed below. It should be noted that the nutrient medium may contain more than one growth regulator belonging to a single class, for example, more than a single auxin-related regulator, or more than one cytokinin-related regulator. The growth regulators will be preferably incorporated into the medium at a concentration between $10^{-10}$ M to $10^{-3}$ M, preferably at $10^{-8}$ to $3\times10^{-5}$ M, and more preferably at the concentrations listed in Table 2.

Unless otherwise indicated, growth media as defined herein provide a suitable starting point for routine optimization of callus culture media and production media. It is a routine matter for those skilled in the art to incorporate, modify, and manipulate particular classes of components, and components from within a given class, to achieve optimum performance; particular media modifications are provided in the Tables and Examples below.

The liquid cultures are exposed to a gaseous environment such as air and preferably shaken or otherwise agitated to allow for proper mixing of culture components. The cultures are maintained at a temperature between 23° C. and 27° C., although under appropriate conditions and/or circumstances, temperatures could range from 0° C. to 33° C. The pH may be from about 3 to 7 and preferably between 4 to 6. The culture may be grown under light conditions ranging from total darkness to total light (narrow band and/or broad spectrum) for various periods of time.

Doubling times have been measured by monitoring time-dependent biomass increase, as well as by simply monitoring the growth index during routine subculture. Maximum dry weight densities of 15-24 grams per liter have been achieved. The growth characteristics of various *Taxus* species suspensions are elaborated in Example 4.

Taxane Production Conditions

If secondary metabolite formation in a suspension culture takes place concurrently with growth, the metabolite is termed growth-associated, and a single medium formulation may be sufficient to achieve good growth and high level production. In many other systems, it has been found that rapid growth and high product formation do not take place concurrently. In such cases, growth and production phases are separated and a medium for each phase is developed independently (reviewed in Payne et al. 1991, Plant Cell and Tissue Culture in Liquid Systems, Hanser publishers, Munich). In the case of taxane production in *Taxus*, growth and product formation can be separated, and independent media have been developed for each.

In a preferred mode of this invention, the composition of the medium during the cell growth phase is different from the composition of the medium during the taxane production phase. For example, the identity and level of the carbon sources, particularly the primary carbon source, may change between the growth phase and the production phase. Preferably the production medium will contain sugar at a level higher than that of the growth medium. More preferably the initial sugar level in the production medium may be 2-20 times higher in the production phase than the growth phase. The primary carbon source is preferably lactose, galactose, raffinose, mannose, cellobiose, arabinose, xylose, sorbitol, or preferably glucose, fructose, sucrose or maltose. The concentration of the primary carbon source may range from 0.05% (w/v) to 10% (w/v), and preferably from 0.1% (w/v) to 8% (w/v). Particularly preferred carbon sources for production of taxol or baccatin are maltose, sucrose, glucose and/or fructose. In particularly preferred embodiments, these sugars will be incorporated in initial nutrient medium at concentrations of at least 3.5%.

The identity and the level of organic supplements, which may include, vitamins, organic nitrogen sources such as amino acids, as well as the presence or levels of the enhancement agents described below, may change or may differ in the media. The identity and levels of the natural or synthetic plant growth regulators may differ between the media. Similarly the levels and identity of macronutrient and micronutrient salts may also differ between the growth and production media. Preferably, the salt content is reduced in the production medium relative to the growth medium, optionally, nitrate and sulfate salts are reduced disproportionately and more preferably the extent of reduction is a reduction by a factor of 2-20 fold. However, it is understood that a single growth/production medium may be formulated for this culture.

The production media developed here not only increase taxane formation, but also direct cellular biosynthesis towards production of particular taxanes, such as taxol or baccatin III. In addition, production of interfering by-products such as cephalomannine is minimal compared to bark tissue. The production media developed here also promote prolonged cell viability and biosynthesis, and in addition, cause significant levels of product to be secreted into the extracellular medium. These characteristics are extremely important in the operation of an efficient commercial scale process for taxane production.

Methods for the extraction and recovery of taxol and taxanes from cells and the medium follow conventional techniques (see, e.g., Example 5). The immuno-assay (ELISA) technique largely followed the protocols supplied by Hawaii Biotechnology in the commercially available kit (see also, Grothaus et al. 1995, *Journal of Natural Products,* 58, 1003-1014 incorporated herein by reference). The antibody may be specific for any taxane, such as taxol or baccatin III, or less specifically, for the taxane skeleton. High performance liquid chromatography methods were slightly modified from existing protocols as elaborated in Example 5. Under the conditions used in this invention, clear resolution of taxane peaks was achieved, resulting in accurate detection and quantitation. Because of the possibility of co-eluting non-taxane components, the spectral purity of taxane peaks were routine by checked by diode array before integration of peak areas. Retention times of taxane standards are listed in Example 5, and a sample chromatogram is included in FIG. 4.

For higher plants, light is a potent factor in secondary metabolism both in intact plant as well as in cell cultures. Both the intensity and wavelength of light are important (Seibert and Kadkade 1980, "Plant Tissue Culture as a Source of Biochemicals." E. J. Staba (ed), CRC Press, Boca Raton, Fla., pp. 123-141). For example, flavanoid and anthocyanin biosynthesis are usually favored by high intensity continuous light, while dark-cultivated cultures may be preferable for other metabolites. Increase in greening or photosynthetic capacity of cultured cells may also increase product formation or product spectrum. The inventors' studies involved the use of broad-band as well as specific narrow-band light sources. As shown in Example 7.3., light exposure can bring about increased taxol accumulation as well as secretion into the medium. The stimulatory effect of light on taxol production suggests the existence of unique control mechanisms for biosynthesis of taxanes. The nature of the photoreceptor and biochemical characteristics of light-induced stimulation are not yet clear. However, the incorporation of enhancement agents, in accordance with the teachings of this invention, render the role of light less critical for optimum performance.

In addition to non-volatile dissolved nutrients, gaseous components, primarily oxygen, carbon dioxide, and ethylene (a plant hormone), play critical roles in growth and product formation. Two parameters are important. The dissolved gas concentrations favoring growth and taxol formation are obviously important since they dictate reactor operating conditions. In addition, the rates of consumption or production need to be incorporated into reactor design, so that the optimum specified concentrations can be maintained.

Besides its importance in respiration, oxygen can also dramatically affect the rate of secondary metabolite biosynthesis. A high saturation constant for an oxygen-requiring step on a secondary biosynthetic pathway may require cells to be subjected to high oxygen levels in the reactor. The importance of $CO_2$ supplementation in maintaining high growth rates has been documented. Ethylene, a plant hormone, plays pleiotropic roles in all aspects of plant growth and development, including secondary metabolism (e.g., see Payne et al., 1991).

The inventors have found that certain gas concentration regimes may favor growth and secondary metabolism in cell cultures. For example, a range of oxygen concentrations may be compatible with culture cultivation, from 1% of air saturation to up to 200% of air saturation, and preferably in the range of 10% to 100%, and most preferably in the range of 25% to 95%. A range of carbon dioxide concentrations may be compatible with culture cultivation, from 0.03% (v/v in the gas phase that is in equilibrium with the culture medium) to 15% (v/v), and preferably in the range of 0.3% to 8% (v/v). The optimal concentrations of dissolved gases may differ with respect to the cell metabolism, for example, cells undergoing rapid growth may have different optima than cells undergoing taxane biosynthesis, which typically favor higher oxygen levels, and are less sensitive to higher carbon dioxide levels. The optima may also vary with the kinetics of the culture; for example, cells in the lag phase may prefer different dissolved gas concentrations than cells in the logarithmic growth phase.

Dissolved gases may interact with other culture components and with the action of enhancement agents in many ways. For example, oxygen requirements may change upon elicitation or stimulation of biosynthesis. Increases in respiration rates as a wound response are commonly observed when plant cell cultures are elicited. Elicitors or stimulators may mediate their action via ethylene, or may affect ethylene production independently of promoting secondary metabolism. In such cases, it may be desirable to substitute a microbial elicitor preparation with ethylene, and perhaps prevent toxicity associated with other microbial components in the elicitor preparation. Alternatively, it may be advantageous to inhibit the action of ethylene, thereby allowing the elicitor or stimulant to promote secondary metabolism in a more exclusive, and thereby more effective, manner. As described below, silver ion, a component known to affect ethylene action, does advantageously modify taxane biosynthesis.

Enhancement Agents

Production of secondary metabolites is a complex process, requiring coordinated action of many different enzymes to produce and sequentially modify the precursors which are ultimately converted into the secondary metabolites. At the same time, secondary metabolite production will be lowered if other enzymes metabolize precursors of the desired metabolite, draining the precursor pools needed to build the secondary metabolites.

Limitation of the amount of available precursor, due to low production or subsequent diversion, or limitation in the conversion of a precursor or intermediate to a downstream intermediate, or limitation in the activity of a given enzyme, will limit the production of secondary metabolites. In any particular culture system, the rate at which a secondary metabolite is produced will be controlled by one of these limitations, forming a bottleneck in the pathway by which the precursor(s) are converted into the secondary metabolite. Relieving the limitation which causes the bottleneck will increase the rate of secondary metabolite production in that culture system up to the point at which another step in the pathway becomes limiting. The particular step which limits the overall rate of production will vary between different cultures, as will the action which relieves the limitation.

Taxanes are secondary metabolites which are produced through a series of many enzymatic steps, and the present inventors have determined several classes of enhancement agents which relieve one or more of the rate limiting steps in taxane biosynthesis. Addition of one of these enhancement agents to a culture of taxane-producing cells will enhance the rate of taxane production. Furthermore, the inventors have determined that use of the enhancement agents discussed herein will have at least some enhancing effect in most taxane-producing cultures, suggesting that the overall production rate is determined not by a single rate-limiting step, but by a complex interaction among a multiplicity of limiting factors. Relief of any one of the limiting factors will enhance taxane production, although the magnitude of the enhancement will depend on particular culture conditions which determine the relative limiting effects of other steps in taxane biosynthesis, once a particular limitation has been relieved. Culture conditions which affect the interaction between various limiting factors include the genetic make up of the cells, the composition of the culture medium and the gaseous environment, temperature, illumination and process protocol, and the enhancement agent(s) added to a particular culture will usually be selected in view of the limiting factors in that culture, which may be determined empirically by comparing the effects of individual enhancement agents as set forth herein. Furthermore, it has been discovered that further enhancement of taxane production will be achieved if more than one enhancement agent is present in the culture.

Representative enhancement agents within the contemplation of this invention are exemplified in Table 1. The enhancement agents of this invention will be discussed under several general classes. These classes are: anti-browning agents, anti-senescence agents, anti-ethylene agents, plant growth regulators, such as auxin-related growth regulators, precursors, inhibitors, elicitors, stimulants and jasmonate-related compounds.

One class of enhancement agents contemplated by this invention are anti-browning agents. As used herein, the term "anti-browning agents" refers to components that are added to the nutrient medium to prevent the formation of pigments during cell cultivation. These pigments include phenolics and related compounds that are generally observed to have a deleterious effect on cell growth, viability, and product formation. A typical anti-browning agent used in the nutrient media according to this invention is ascorbic acid. Anti-browning agents may be typically incorporated in the medium at a concentration range of 10 ppb to 1000 ppm.

Another class of enhancement agents is anti-senescence agents. An anti-senescence agent is a compound of biological or non-biological origin that protects cells from senescence. Such agents could act by, for example, blocking the production of compounds that promote senescence, blocking the action of senescence-promoting factors, providing radical-scavenging or anti-oxidant activities, protecting the integrity of cellular membranes and organelles, or by other mechanisms. Such agents include antagonists of ethylene action; polyamines and their metabolites, such as spermine, spermidine, diaminopropane, and the like; anti-browning agents, inhibitors of phenolics production, and radical scavengers, such as reduced glutathione, propyl gallate, and sulfhydryl compounds such as β-mercaptoethanolamine.

Anti-ethylene agents are defined as substances that interfere with ethylene production or ethylene action. Anti-ethylene agents that interfere with ethylene metabolism may be further classified as ethylene-biosynthesis antagonists, and ethylene-action antagonists. Ethylene-biosynthesis antagonists are compounds that interfere with the biosynthetic pathway to ethylene; examples of enzymes along this biosynthetic pathway that are inhibited include ACC synthase, ACC oxidase, and ethylene oxidase. Examples of ethylene biosynthesis antagonists include α-aminoisobutyric acid, acetylsalicylic acid, methoxyvinylglycine, aminooxyacetic acid and the like.

Examples of ethylene action antagonists include silver containing compounds, silver complexes, or silver ions, carbon dioxide, 1-methylcyclopropene, 2,5-norbornadiene, trans-cyclooctene, cis-butene, diazo-cyclopentadiene and the like. Suitable silver salts include silver nitrate, silver thiosulfate, silver phosphate, silver benzoate, silver sulfate, silver salt of toluenesulfonic acid, silver chloride, silver oxide, silver acetate, silver pentafluoropropionate, silver cyanate, silver salt of lactic acid, silver hexafluorophosphate, silver nitrite, and the trisilver salt of citric acid. Illustrative examples of the enhancement of taxane biosynthesis by a variety of silver salts are shown in Example 10.

Anti-ethylene agents may be incorporated into the medium at levels of 10 ppb to 1000 ppm. When silver is incorporated in the medium, it will be added at a concentration of less than 900 µM, preferably less than 500 µM, and more preferably less than 200 µM. When silver is incorporated in the medium, it will be added at a concentration of at least 10 nM, preferably 100 nM, more preferably 1 µM, and typically at 10 µM.

Enhancement agents contemplated in this invention include plant growth regulators, particularly auxin-related growth regulators, which will include auxins, compounds with auxin-like activity, and auxin antagonists. Auxin-related growth regulators will typically be incorporated in the medium at concentrations of between $10^{-10}$ M to $10^{-3}$ M, preferably between $10^{-8}$ to $10^{-5}$ M. Most preferred examples of auxin-related growth regulators include 1-Naphthaleneacetic acid, 2-Naphthaleneacetic acid, 1-Naphthaleneacetamide/Naphthylacetamide, N-(1-Naphthyl)phthalamic acid, 1-Naphthoxyacetic acid, 2-Naphthoxyacetic acid, beta-Naphthoxyacetic acid, 1-Naphthoxyacetamide, 3-Chlorophenoxyacetic acid, 4-Chlorophenoxyacetic acid, 4-Iodophenoxyacetic acid, Indoleacetamide, Indoleacetic acid, Indoylacetate, Indoleacetyl leucine, Gamma-(3-Indole)butyric acid, 4-Amino-3,5,6-trichloropicolinic acid, 4-Amino-3,5,6-trichloropicolinic acid methyl ester, 3,6-Dichloro-o-anisic acid, 3,7-Dichloro-8-quinolinecarboxylic acid, Phenylacetic acid, 2-Iodophenylacetic acid, 3-Iodophenylacetic acid, 2-Methoxyphenylacetic acid, Chlorpropham, 4-chloroindole-3-acetic acid, 5-Chloroindole-3-acetic acid, 5-Bromo-4-chloro-3-indoyl butyrate, Indoleacetyl phenylalanine, Indoleacetyl glycine, Indoleacetyl alanine, 4-chloroindole, p-chlorophenoxyisobutyric acid, 1-pyrenoxylbenzoic acid, Lysophosphatidic acid, 1-naphthyl-N-methylcarbamate, and Ethyl-5-chloro-1H-Indazole-3-ylacetate-3-Indolebutanoic acid. Other preferred examples of auxin-related growth regulators include Naphthalene-2,6-dicarboxylic acid, Naphthalene-1,4,5,8-tetracarboxylic acid dianhydride, Naphathalene-2-sulfonamide, 4-Amino-3,6-disulfo-1,8-naphthalic anhydride, 3,5-dimethylphenoxyacetic acid, 1,8-Naphthalimide, 2,4-Dichlorophenoxyacetic acid, 2,3-Dichlorophenoxyacetic acid, 2,3,5-Trichlorophenoxyacetic acid, 2-Methyl-4-chlorophenoxyacetic acid, Nitrophenoxyacetic acids, DL-alpha-(2,4-Dichlorophenoxy)propionic acid, D-alpha-(2,4-Dichlorophenoxy)propionic acid, 4-Bromophenoxyacetic acid, 4-Fluorophenoxyacetic acid, 2-Hydroxyphenoxyacetic acid, 5-Chloroindole, 6-Chloro-3-indoylacetate, 5-Fluoroindole, 5-Chloroindole-2-carboxylic acid, 3-Chloroindole-2-carboxylic acid, Indole-3-pyruvic acid, 5-Bromo-4-chloro-3-indoylbutyrate, 6-Chloro-3-indoylbutyrate, Quinoline-2-thioglycolic acid, Aminophenylacetic acids, 3-Nitrophenylacetic acid, 3-Chloro-4-hydroxybenzoic acid, Chlorflurenol, 6-Chloro-3-indoyl acetate, N-(6-aminohexyl)-5-chloro-1-Naphthalenesulfonamide hydrochloride, 2-chloro-3(2,3-dichloro-phenyl) propionitrile, O-chlorophenoxyacetic acid, 6,7-dimethoxy-1,2-benzisoxazole-3-acetic acid, 3-oxo-1,2,-benzisothiazoline-2-ylacetic acid, Mastoparan, 2,3,5-Triiodobenzoic acid, 2-(3-chlorophenoxy)propanoic acid, and Mecoprop. Other examples of suitable auxin-related growth regulators include Naphthoic acid hydrazide, 2,4-Dibromophenoxyacetic acid, 3-Trifluoromethylphenoxyacetic acid, Oxindole, Indole-2-carboxylic acid, Indole-3-lactic acid, Beta-(3-Indole)propionic acid, 2-Bromophenylacetic acid, 3-Bromophenylacetic acid, 2-Chlorophenylacetic acid, 3-Chlorophenylacetic acid, 2-Methylphenylacetic acid, 3-Methylphenylacetic acid, 3-Trifluoromethylphenylacetic acid, 3-Methylthiophenylacetic acid, Phenylpropionic acid, 4-chloro-2-methylphenylthioacetic acid, 2-Chlorobenzoic acid, 3-Chlorobenzoic acid, 2,3-Dichlorobenzoic acid, 3,4-Dichlorobenzoic acid, 2,3,5-Trichlorobenzoic acid, 2,4,6-Trichlorobenzoic acid, 2-Benzothiazoleoxyacetic acid, 2-Chloro-3-(2,3-dichlorophenyl)propionitrile, 2,4-Diamino-s-triazine, Naphthalic anhydride, Dikegulac, chlorflurecolmethyl ester, 2-(p-chlorophenoxy)-2-methylpropionic acid, 2-chloro-9-hydroxyfluorene-9-carboxylic acid, 2,4,6-trichlorophenoxyacetic acid, 2-(p-chlorophenoxy)-2-methyl propionic acid, Ethyl 4-(chloro-o-tolyloxy)butyrate, [N-(1,3-dimethyl-1H-Pyrazol-5-yl)-2-(3,5,6-Trichloro-2-pyridinyl)oxy]acetamide, 4-Chloro-2-oxobenzothiazolin-3-yl-acetic acid, 2-(2,4-Dichlorophenoxy)propanoic acid, 2-(2,4,5-Trichlorophenoxy) propanoic acid, 4-Fluorophenylacetic acid, 3Hydroxyphenylacetic acid, Orthonil, 3,4,5-Trimethoxycinnamic acid, 2(3,4-dichlorophenoxy)triethylamine, Indole-3-propionic acid, Sodium Ioxynil, 2-Benzothiazoleacetic acid, and (3-phenyl-1,2,4-thiadiazol-5-yl)thioacetic acid.

Other classes of plant growth regulators may also be incorporated into the nutrient medium as enhancement agents. These include cytokinin-related growth regulators such as $N^6$-benzyladenine, 6-[γ,γ-dimethylallylamino] purine, kinetin, zeatin, N-phenyl-N'-1,2,3-thidiazol-5-ylurea (thidiazuron) and related phenylurea derivatives and the like, gibberrellins such as $GA_3$, $GA_4$, $GA_7$, and GA derivatives, abscisic acid and its derivatives, brassinosteroids, and ethylene-related growth regulators. Such growth regulators may be incorporated in the medium at concentrations between $10^{-10}$M and $10^{-3}$M, preferable between $10^{-8}$M and $10^{-5}$M.

Another class of enhancement agents are "precursors" or biosynthetic precursors. As used herein, the term precursors are used to describe compounds added to the nutrient medium that are metabolized and incorporated by the cells into taxol and taxanes. Suitable precursors include precursors of isoprenoid compounds such as acetate, pyruvate and the like; α-phenylalanine, β-phenylalanine (3-amino-3-phenylpropionic acid), phenylisoserine, N-benzoylphenylisoserine, benzoic acid, shikimic acid, glutamine, cinnamic acid, and the like. Derivatives of the aforementioned molecules are also suitable as precursors.

Another class of enhancement agents are inhibitors. Inhibitors are compounds which inhibit enzymatic or other cellular activities As used herein, the term "metabolic inhibitors" is used to describe compounds added to the nutrient medium that interfere with specific biosynthetic pathways. For example, a metabolic inhibitor may be used to enhance taxol, baccatin III, or other taxane biosynthesis by blocking a different pathway that competes for an early biosynthetic precursor. Particularly effective enhancement agents of this class include inhibitors of phenylpropanoid metabolism, which are compounds capable of inhibiting the synthesis or metabolism of cinnamic acid or its derivatives. These compounds include preferably p-Coumaric acid, 4-Fluoro-DL-tyrosine, 4-Methoxybenzoic acid, 3-dimethylaminobenzoic acid, 4-methoxycinnanic acid, 4-nitrocinnamic acid ethyl ester, 4-Nitrocinnamaldehyde, Mercaptoethanol, 4-hydroxycoumarin, Cinnamylfluorene, 2-cyano-4-hydroxycinnamic acid, Cinnamylidenemalonic acid, 4-dimethylaminocinnamic acid, N-cinnamylpiperazine, N-Trans-cinnamoylimidazole, 2-Aminoindan-2-Phosphonic acid, Benzylhydroxylamine, Procaine, Monensin, N-(4-Hydroxyphenyl)glycine, 3-(4-hydroxyphenyl)propionic acid, 3-(2-hydroxyphenyl) propionic acid, more preferably D-Phenylalanine, N-(2-mercaptopropionyl) glycine and its acetic acid salt complex, DL-Metafluorophenylalanine, p-Fluoro-DL-phenylalanine, Dithiothreitol, 4-Fluorocinnamic acid, Trans-3,4-Difluorocinnamic acid, 3,4-Difluoro-D-Phenylalanine, diethyldithiocarbanic acid, 4-Fluoro-(1-amino-2-phenylethyl) phosphonic acid, 3,4-methylenedioxybenzoic acid, and most preferably 3,4-methylenedioxy-6-nitrocinnamic acid, 3,4-methylenedioxycinnamic acid, 3-[3,4-methylenedioxyphenyl] propionic acid, 3,4-methylenedioxyphenylacetic acid, 4-Fluoro-L-Phenylalanine, 4-Hydroxyphenylpyruvic acid, 4-Fluoro-DL-Tyrosine, Trans 3,4-Dimethoxycinnamic acid, phenylpropiolic acid, L-2-Hydroxy-3-Phenylpropionic acid, 2-hydroxy-4,6-dimethoxybenzoic acid, SKF-525A (2-(diethylamino) ethyl ester of α-phenyl-α-propylbenzeneacetic acid), vinylimidazole, ammonium oxalate, sinapic acid, and 1-aminobenzotriazole and related analogs. When incorporated into the medium, the inhibitors will be added at a concentration between 10 ppb and 1000 ppm, preferably at a concentration between 100 ppb and 100 ppm, and more preferably at a concentration of 1 ppm to 50 ppm.

In order to improve the yield of taxol, baccatin III, and other related taxanes in cell cultures, the inventors have undertaken a number of approaches. One of the approaches that has been used to enhance productivity is the use of so-called elicitors. As used herein, the term "elicitors" is used for compounds of biological and non-biological origin that cause an increase in secondary metabolite production when applied to plants or plant-cell cultures (Eilert 1987, "Cell Culture and Somatic Genetics of Plants," Vol. 4, F. Constabel and I. K. Vasil (eds.), Academic Press, New York, pp. 153-196; Ebel, 1984, *Bioregulators: Chemistry and Uses*. 257-271; and Darvill et al., 1984, *Ann. Rev. Plant Physiol.*, 35, 243-275). Many different compounds can act as elicitors, depending upon their nature of origin and their mode of action with cell metabolism. In these studies, the inventors have used two major kinds of elicitors: 1) Biotic elicitors which usually comprise cell wall extracts or filtrates from a selected group of fungi, bacteria and yeasts, and also their purified fractions. 2) Abiotic elicitors which have included chemical stress agents as well as some compounds of biological origin (see elicitors listed in Table 1). In addition, salts and complexes containing heavy metal ions may also be considered as effective abiotic elicitors; these include examples such as cobalt, nickel, lanthanum, selenium, vanadium, lead, cadmium, chromium, aluminium, iodine, barium, bismuth, lithium, rubidium, strontium, and gold. It should be noted that certain compounds that mediate elicitation, for example, the jasmonate-related compounds described below, may also be considered as elicitors.

Christen et al. (1991) report the use of fungal elicitors and selected compounds for production of taxol by suspensions of *Taxus brevifolia*; however, the increases in the level of taxol accumulation due to elicitor treatments have not been specified.

In general, both kinds of elicitors were effective, although the extent to which elicitation (taxane accumulation in cell cultures as well as their secretion into the medium) occurred differed from elicitor to elicitor and from species to species. The highest production increase was attained with chitosan glutamate, lichenan, ferulic acid and benzoic acid. Chitosan and lichenan are complex polysaccharides derived from microbial cell walls. Chitosan when used alone is insoluble in medium, and is toxic and causes permanent cell damage. Chitosan glutamate, on the other hand, is readily soluble in medium and does not affect cell viability. Ferulic and benzoic acids are synthesized chemicals of biological origin, and are generally used as anti-oxidants in biological systems.

Elicitors and metabolic stress agents may be utilized according to this invention to maximize taxol, baccatin III, and total taxane production and secretion in tissue culture by assessing elicitor specificity and concentration, timing, and duration, as a function of culture age and media composition.

Another class of enhancement agents contemplated in this invention are stimulants. As used herein the term stimulant is used to describe compounds added to the nutrient medium that stimulate or activate specific biosynthetic pathways, for example those leading to biosynthesis.

Jasmonate-related compounds are a class of compounds that mediate the elicitation reaction, thereby stimulating secondary metabolite biosynthesis. Jasmonate-related compounds include jasmonic acid and its alkyl esters, such as methyl jasmonate, ethyl jasmonate, propyl jasmonate, butyl jasmonate, pentyl jasmonate, hexyl jasmonate; dihydrojasmonic acid and its alkyl esters, such as methyl dihydrojasmonate, ethyl dihydrojasmonate, n-propyl dihydrojasmonate, butyl dihydrojasmonate, pentyl dihydrojasmonate, hexyl dihydrojasmonate; epimethyl jasmonate, fluoromethyl jasmonate, cis-jasmone, isojasmone, tetrahydrojasmone, 12-oxophytodienoic acid, dihydrojasmone, jasmonyl acetate, apritone, amylcyclopentenone, hexylcyclopentenone, hexylcyclopentanone, and related derivatives and analogs. Preferred jasmonate-related compounds include alkyl esters of jasmonic acid, where the alkyl group esterified to jasmonic acid has form one to four carbon atoms. Jasmonate-related compounds are incorporated into the medium at concentrations of $10^{-9}$ M to $10^{-3}$ M and preferably at concentrations of $10^{-6}$ to $5 \times 10^{-4}$ M, and more preferably at concentrations of $10^{-5}$ M to $2 \times 10^{-4}$ M. It should be noted that more than one jasmonate-related compound may be incorporated into the nutrient medium. It will be recognized by the skilled artisan that the concentration of enhancement agents such as jasmonate-related compounds, auxin-related growth regulators, precursors, and other nutrients will change as these compounds are metabolized in the culture. Unless otherwise indicated, the concentrations recited herein refer to the initial concentration in the nutrient medium.

Combining enhancement agents from at least two of the following classes of enhancement agents has been shown to enhance taxane production by *Taxus* cells beyond the maximum enhancement observed for any one of the agents when used alone. These classes of enhancement agents are elicitors, jasmonate-related compounds, inhibitors of ethylene action, inhibitors of phenylpropanoid metabolism, antisenescence agents, precursors and auxin-related growth regulators. Therefore, in a preferred mode, this invention provides methods for enhancing production of one or more taxanes by culturing cells of a *Taxus* species in the presence of enhancement agents selected from at least two of these agent groups.

Preferred methods for taxane production use the prototype inhibitor of ethylene action, silver, in combination with at least one other enhancement agent, and in particularly preferred methods the other agent is methyl jasmonate, or an inhibitor of phenylpropanoid metabolism, such as 3,4-methylenedioxynitrocinnamic acid.

When used in combination with each other, jasmonate-related compounds and ethylene-action inhibitors may be incorporated into the nutrient medium in certain proportions to each other. For example, when methyl jasmonate and silver thiosulfate are used in combination, the molar ratios of methyl jasmonate to the silver ion may be in the range between 0.0001 to 9.5, preferably in the range between 0.001 to 8, more preferably in the range between 0.1 to 7, and most preferably in the range between 1 to 5.

When used in combination with each other, auxin-related growth regulators and ethylene-action inhibitors may be incorporated into the nutrient medium in certain proportions to each other. For example, when an auxin-related growth regulator and silver thiosulfate are used in combination, the molar ratios of auxin-related growth regulator to silver ion may be in the range between 0.011 to 1000, preferably in the range between 0.015 to 100, and more preferably in the range between 0.02 to 50, and most preferably between 0.05 to 30.

Generally, when culturing of *Taxus* cells for the production of taxanes, one or more auxin-related growth regulator will be added to the culture medium. Presence of auxin-related growth regulator(s) will promote cell growth, but more significantly will enhance production of taxanes by the culture. Further enhancement can be obtained by adding at least one other enhancement agent contemporaneously with the auxin-related growth factor.

In a preferred mode of this invention, one or more enhancement agents are added to the culture in an amount sufficient to enhance the production of one or more taxanes by at least 3-fold, preferably by at least 5-fold, more preferably by at least 10-fold, and even more preferably by at least 30-fold relative to the level of production in the absence of the enhancer(s). In another preferred mode of this invention, one or more enhancement agents are added to the culture in an amount sufficient to enhance the volumetric productivity of taxol to at least to 10 mg/L/day, more preferably to at least 15 mg/L/day, and even more preferably to at least 22 mg/L/day. In another preferred mode of this invention, one or more enhancement agents are added to the culture in an amount sufficient to enhance the whole broth titer of taxol to at least 150 mg/L, more preferably to at least 200 mg/L, and even more preferably to at least 350 mg/L. In another preferred mode of this invention, one or more enhancement agents are added to the culture in an amount sufficient to enhance the volumetric productivity of baccatin III to at least 15 mg/L/day, more preferably to at least 20 mg/L/day, and even more preferably to at least 25 mg/L/day. In another preferred mode of this invention, one or more enhancement agents are added to the culture in an amount sufficient to enhance the whole broth titer of baccatin III to at least 100 mg/L, more preferably to at least 150 mg/L, and even more preferably to at least 250 mg/L. In another preferred mode of this invention, one or more enhancement agents are added to the culture in an amount sufficient to enhance the volumetric productivity of taxanes to at least 15 mg/L/day, more preferably to at least 25 mg/L/day, and even more preferably to at least 40 mg/L/day. In another preferred mode of this invention, one or more enhancement agents are added to the culture in an amount sufficient to enhance the whole broth titer of taxanes to at least 200 mg/L, more preferably to at least 300 mg/L, and even more preferably to at least 400 mg/L.

Many of the compounds described as enhancement agents above have been used in other plant systems. Formulation, administration, and appropriate physiological concentration levels in these non-*Taxus* systems will provide guidance for the skilled artisan to apply these agents in accordance with this invention.

Cellular Material

Suitable cells for culture in the method of this invention may be from any species of *Taxus*. Preferably, the cells will be from a cell line that inherently produces taxanes in relatively high yield. Typically, such cells have the ability to produce high levels of one or more taxanes under standard conditions or exhibit high average volumetric productivities of taxanes under standard conditions. Suitable cell lines may be identified by culturing cells of the cell line under standard taxane production conditions and observing the level of one or more taxanes produced in the culture or determining the average volumetric productivity for one or more taxanes by the cells in the culture by the following procedures.

Cells for use in the production culture testing procedure are grown in a suitable medium adapted for the particular cell line. Following completion of log phase growth, an aliquot of cells is cultured for test production of taxanes. Production culture is generally performed in liquid medium, although callus culture on solid medium may be used. In production culture, the cells are cultivated in medium N from Table 2, in medium N from Table 2 except for replacement of sucrose by 7% (w/v) maltose, or in a nutrient medium optimized for growth and maintenance of the particular cell line. In the production culture, the cell density should be in the range of 15-20 percent (w/v) on a fresh weight basis. Cells are cultured for 10-20 days at 25° C. under dark conditions. Liquid cultures should be appropriately agitated and aerated, for example on a rotary shaker at 120-180 rpm.

Production cultures for evaluating cell line characteristics will include suitable enhancement agents. Generally, six alternative enhancement cocktails (combinations of up to five enhancement agents) are tested for each cell line. The combinations are shown in Table A below.

At the end of the culture, titer of individual taxanes in the culture may be measured by ELISA assay performed as described herein, or the profile of taxanes produced in the culture may be determined by HPLC analysis as described in Example 5. Preferred cell lines will produce one or more taxanes above the minimum target taxane levels in one or more of the enhancement cocktails. Preferred cell lines will exceed the target levels for both titre and productivity for at least one enhancement cocktail, and more preferably for two or more enhancement cocktails. Minimum target taxane titer at the end of production culture for suitable cell lines will be at least 100 mg/L taxanes. Alternatively, the minimum average volumetric productivity target over the course of the production culture will be 10 mg/L/day taxanes. More preferred cell lines will achieve minimum taxane titer at the end of production culture of at least 100 mg/L taxol or 200 mg/L baccatin III, or average volumetric productivity over the course of the production culture of 10 mg/L/day taxol or 15 mg/L/day baccatin III.

Table A. Enhancement Cocktails

Combinations of Enhancement Agents:
1. 20 μM Naa+30 μM Mdna
2. 20 μM Naa+30 μM Mdna+50 μM Slts
3. 20 μM Naa+30 μM Mdna+89 μM Mjs
4. 20 μM Naa+30 μM Mdna+89 μM Mjs+50 μM Slts
5. 20 μM Naa+30 μM Mdna+89 μM Mjs+50 μM Slts+5 mM Gln
6. 20 μM Naa+89 μM Mjs+50 μM Slts Gln=glutamine
Naa=1-naphthaleneacetic acid
Mdna=3,4-methylenedioxy-6-nitrocinnamic acid
Mjs=methyl jasmonate
Slts=silver thiosulfate Suitable production media for the various species are listed in Table 5, although others may be used. For example, Media B, C and N from Table 2 are particularly suitable production media for *Taxus chinensis*. Media preferably contain the ingredients listed in Table 2. These media preferably contain major and minor inorganic salts, organics and growth hormones or growth regulators, in the amounts generally with the preferred ranges starting with the 1/10th to three times the concentration of each medium ingredient indicated in Table 2. Where medium B or N is used, the growth regulators are typically incorporated into the medium in an amount between 0.1 ppm to 20 ppm, and preferably between 1 ppm to 10 ppm. When Medium C or N is used, the growth regulators are incorporated preferably at levels ranging from 0.1 ppm to 5 ppm.

It will be understood by the skilled artisan that within the contemplation of this invention modifications may be made in the media described herein, such as substitution of other conventional compositions (such as organics, vitamins, amino acids, precursors, activators and inhibitors), addition or deletion of various components, including growth regulators, or alteration of proportions, so as to produce growth and taxane production equal to or better than that observed with the media in Table 2.

Modes of Process Operation

The operating mode for a plant cell culture process refers to the way that nutrients, cells and products are added or removed with respect to time (Payne et al. 1991). When all the nutrients are supplied initially, and the culture contents comprising cells and product are harvested at the end of the culture period, the operating mode is termed a "one-stage batch process". When a batch process is divided into two sequential phases, a growth and a production phase, with the medium being exchanged in between the two phases, the operating mode is termed a "two-stage batch process". Within the contemplation of this invention, the transition from the growth medium to production medium, may occur by an abrupt stepwise change, or progressively by a series of continuous steps, or by progressive change. In one extreme the progressive change is accomplished by progressive replacement of medium, of incrementally changing composition. In another alternative, the progressive change is accomplished by feeding one or more components of the production medium into the growth phase culture. This is one example of the fed-batch process.

In a "fed-batch" operation, particular medium components such as nutrients and/or one or more enhancement agents are supplied either periodically or continuously during the course of a culture. It should be noted that certain components may be incorporated into the nutrient medium initially in the batch mode, then added in fed-batch mode, or may be added to the nutrient medium exclusively in the fed-batch mode.

Using fed-batch operation, it has been found that cells can be sustained in a productive state for a prolonged period, and in fact, that productivity of the cells could be enhanced. As illustrated in Examples 15 and 17, and in Tables 16 and 18, adding certain nutrients and enhancement agents in a fed-batch manner gave significant improvements in overall performance for taxanes generally, and for specific taxanes such as taxol and bacctin III. Further, this mode of operation has been found to be compatible with a variety of different cell lines under a variety of different media conditions.

Fed-batch addition of components is particularly advantageous when the concentration of the particular component has to be maintained at a low level in the culture, for example, to circumvent the effects of substrate inhibition. Similarly, fed-batch addition is advantageous when cells react negatively to a component when it is either added initially to the nutrient medium or if stoichiometrically-meaningful quantities of a component cannot be added due to solubility or toxicity limitations. Further, continuous or continual (periodic) fed-batch addition of a feed solution containing a component is particularly preferred when cells react negatively to the component when it is added in a more rapid manner such as pulse addition. Particular components to which cells respond favorably when added in a fed-batch mode include taxane precursors such as alpha- and beta-phenylalanine; carbon sources such as maltose, fructose and glucose; amino acids such as glutamine, glutamic acid, aspartic acid; macronutrients such as phosphate, calcium, and magnesium; and enhancement agents such as auxin-related growth regulators and jasmonate-related compounds.

It will be apparent to the skilled artisan, that the composition of the feed may be varied to obtain the desired results such as extension of the production phase to increase taxane yield or extension of the growth phase to achieve higher biomass density. Selection of suitable conditions to achieve optimum productivity and performance is easily within the skill of the ordinary artisan in view of the teachings described herein. Similarly variations of other operating parameters, such as the timing and duration of the addition and the rate of the addition of the fed-batch components, to achieve the desired results, are within the reach of the skilled artisan in view of the teachings described herein.

Medium exchange as described herein refers to the removal of spent medium from the culture followed by addition of fresh medium to the culture; the cells are largely retained in the culture during the operation. In the method of this invention, medium exchange operation is an advantageous method to obtain and sustain high volumetric productivities of taxane production, resulting in superior process performance and overall production levels, compared to a batch process. The extracellular product resulting from such an operation may lend itself to more facile downstream recovery and purification than other process modes.

As illustrated in Example 14 and Table 15, medium exchange is successful in sustaining high productivities for taxanes generally, and for specific taxanes such as taxol, baccatin III, and 10-deacetylbaccatin III. In addition, this mode of operation resulted in the increase in the volumetric productivity relative to batch operation for taxanes generally, and for specific taxanes such as taxol and baccatin III. Further, this mode of operation is compatible with a variety of different cell lines under a variety of different media conditions. As further illustrated in Example 7.2, the removal of spent medium and replenishment of fresh medium every 3 days contributed to significant enhancement of taxane and taxol production in growth conditions, as well as to an increase in the amounts of extracellular product.

The stimulatory effects of medium exchange may have been due to removal of product in situ, which would prevent feedback inhibition and product degradation. Such positive effects of in situ product removal on secondary metabolite production and secretion in suspension cultures have been documented by, among others, Robins and Rhodes (1986, *Appl. Microbiol. Biotechnol.*, 24, 35-41) and Asada and Shuler (1989. *Appl. Microbiol. Biotechnol.*, 30, 475-481). The periodic removal of spent medium incorporates the above advantages, and additionally, may serve to de-repress secondary biosynthesis by removing other, non-taxane, inhibitory components (such as phenolic compounds) from the medium.

The replenishment of fresh medium to cells undergoing active biosynthesis may also enhance production by providing essential nutrients that have been depleted. For example, Miyasaka et al. (1986, *Phytochemistry*, 25, 637-640) were able to stimulate stationary phase cells of *Salvia miltiorhiza* to produce the diterpene metabolites, cryptotanshinone and ferruginol simply by adding sucrose to the medium. Presumably, biosynthesis had ceased due to carbon limitation in the stationary phase. The periodic-medium-exchange protocol used in the present work could have been beneficial as a result of any of the above factors. It is understood that the amount of medium exchanged, the frequency of exchange, and the composition of the medium being replenished may be varied. The ability to stimulate biosynthesis and secretion by medium exchange has important implications for the design and operation of an efficient commercial process in the continuous, semi-continuous or fed-batch mode.

When a substantial portion, but not all, of the contents of a batch culture is harvested, with addition of fresh medium for continued cell growth and production, the process resembles a "repeated draw and fill" operation, and is termed a "semi-continuous process". When fresh medium is continuously supplied, and effluent medium is continuously removed, the process is termed "continuous". If cells are retained within the reactor, the process is termed a "perfusion mode" If cells are continuously removed with the effluent medium, the continuous process is termed a "chemostat".

It is understood that these various modes of process operation are compatible with the taxane-production system described herein.

EXAMPLES

The following examples are provided to further describe the materials and methods which may be used in carrying out the invention. The examples are intended to be illustrative and are not intended to limit the invention in any manner.

Example 1

Callus Initiation

Samples of *Taxus* plant material were collected from a number of wild and cultivated plants. Samples were processed upon arrival at the laboratory or stored at 4° C. until they could be used.

The material was first washed in dilute soap solution, rinsed in water, and the surface sterilized in a CLOROX solution (1% hypochlorite, pH 7) for 10 minutes. Under sterile conditions the material was then rinsed 3 times with sterile water. Needles were then cut in a 1% polyvinylpyrrolidone (PVP) solution with 100 mg/l ascorbic acid. Needles were placed with the cut end in Medium E (see Table 2). Thirty to forty explants were cultured per plate of medium. Plates containing explants were incubated at 25±1° C. in the dark. Plates were monitored daily for the appearance of contaminating micro-organisms, and where they were present, uncontaminated needles were removed and placed in a fresh plate of Medium E. Substantial callus formation was observed and the callus was separated from the explant at 20 days and placed on the various callus proliferation media listed in Table 3. For example, calli of *Taxus chinensis* were transferred to Medium D (see Table 2). This initiation procedure was very efficient, resulting in low contamination rate and high frequency of callus induction of over 90% of explants initiated. The same procedure was successfully used to initiate cultures of *Taxus brevifolia, Taxus canadensis, Taxus cuspidata, Taxus baccata, Taxus globosa, Taxus floridana, Taxus wallichiana, Taxus media,* and *Taxus chinensis*.

Example 2

Callus Proliferation

Once calli were removed from the explant, they were cultivated at 25±1° C. in the dark. Healthy parts of the callus were transferred to fresh medium every 7 to 10 days, and this frequency of transfer was found to be extremely important for prevention of browning and for prolonged callus maintenance. The preferred growth and maintenance media for calli of various species are summarized in Table 3.

Example 3

Suspension Initiation 1 g fresh weight of callus material was aseptically inoculated into a 125 ml Erlenmeyer flask containing 25 ml of liquid medium appropriate to each species (see Table 3). For example, Medium D was used for *Taxus chinensis*. The flask was covered with a silicone foam cap (Bellco, N.J.) and placed on a gyratory shaker at 120 rpm at 24±1° C. in darkness. Suspension cultures were formed in approximately 3 to 10 days. Initially, medium was exchanged by suction filtering the flask contents through a buchner funnel containing a miracloth filter (Calbiochem), and resuspending all the biomass in fresh medium. Upon cell growth, 1-2 g (fresh weight) of cells, and were generally transferred into a new 125 ml flask containing 25 mL of fresh medium and were thereafter subcultured weekly.

Example 4

Growth of Suspended Cells

The typical growth rates and cell densities achieved in suspension cultures of representative species are listed in Table 4.

As a detailed example, the increase in biomass (fresh and dry weight) with time for *Taxus chinensis* line K-1 is shown in FIG. 1. The maximum growth rate was measured by taking the slope at points of most rapid biomass increase on the growth curves. Cell cultures of *Taxus chinensis* grew at a maximum doubling time of 2.5 days. This growth rate is significantly higher than that reported previously for *Taxus* species suspension cultures. For example, Christen et al. (1991) reported a 5- to 10-fold increase in biomass after 3 to 4 weeks of culture, which translates to an average doubling time for *Taxus brevifolia* suspensions of 7 to 12 days.

The ability to cultivate cells at a high density is important in maximizing the volumetric productivity of a cell culture process. While cultures of *Taxus brevifolia* reached a cell density of less than 1 g dry weight per liter (calculated from data presented in Christen et al. (1991)), suspensions of *Taxus chinensis* were able to reach densities of up to 8 to 20 g dry weight per liter after 18 days of growth. The viability of cells was determined by staining cells with a 0.05% solution of fluorescein diacetate in acetone (Widholm, 1972, *Stain Technol.*, 47, 189-194), and by counting the number of green fluorescing cells upon excitation with blue light in an inverted fluorescence microscope (Olympus IMT-2, Japan). Cell viability was higher than 90% throughout the growth phase.

The ability to cultivate cells under rapid growth conditions to high cell densities while retaining high viability is an important pre-requisite to the economic operation of a plant cell culture process for producing taxol, baccatin III, and taxanes.

Example 5

Analysis of Taxol, Baccatin III and Other Taxanes 5.1. ELISA Methods

ELISA analysis (Hawaii Biotech #TA-01) was used for detection of taxol in cell culture extracts (see Grothaus, et al., 1995). This method provides high sensitivity (0.1 ng/mL), however, because a polyclonal antibody is used, cross-reactivity with other taxanes is observed. Preparative (analytical scale) HPLC with fraction collection showed cross-reactivity with 10-deacetyltaxol, 7-xylosyl-10-deacetyltaxol, cephalomannine, 10-deacetyl-7-epitaxol, 7 epitaxol, as well as other unidentified taxanes. Despite such cross-reactivity this method was found to be extremely useful for detection of taxane production and allowed large numbers of cell lines to be screened quickly. Cell extracts showing significant production of taxanes were then analyzed in detail using the HPLC procedures outlined below.

A monoclonal ELISA analysis (Hawaii Biotech #TA-02) was also used for detection of taxol in cell culture extracts. This method provides high sensitivity (0.1 ng/mL) and significantly less cross-reactivity.

5.2. Extraction of Taxol, Baccatin III, and Other Taxanes

Extraction of taxanes from supernatants were performed by several methods depending on the concentrations present.

When sufficient amounts of taxanes (approx. 1-5 mg/L) are present in liquid media, samples were prepared very rapidly and efficiently. Media (2 μL) were dried completely (in vacuo) and a measured amount of methanol (0.5-2.0 mL) was added. This mixture was agitated ultrasonically until complete dissolution or dispersion of the sample was accomplished. Solids were removed by centrifugation prior to HPLC analysis. Quantitative recoveries have been obtained at 1 mg/L levels with detection levels well below 0.1 mg/L.

When concentration of taxanes in the culture supernatants were very low (less than 1 mg/L), the medium was extracted three times with an equal volume of a mixture of methylene chloride and isopropyl alcohol (IPA) (9:1 by vol.). The organic layer was reduced to dryness and reconstituted in a measured volume of methanol (50-250 mL). Multiple extraction typically recovered 90-95% of the taxol, cephalomannine, and baccatin III at 0.6 mg/L levels.

When taxane concentrations in the supernatant exceeded ~5 mg/L a more rapid sample preparation was employed. One part (vol.) of supernatant was mixed with 3 parts (vol.) of methanol containing 0.1% acetic acid. This mixture then was sonicated for 30 minutes, filtered, and analyzed by HPLC.

Samples of whole broth (culture supernatant containing cells) were prepared using a method similar to that described in the preceding paragraph. One part (vol.) of whole broth was mixed with 3 parts (vol.) of methanol containing 0.1% acetic acid. This mixture then was sonicated for 30 minutes, allowed to stand for an additional 30 minutes, filtered and then analyzed by HPLC.

Cell materials were extracted by freezing freshly harvested cells (-5° C.), followed by vacuum drying, and methanol soxhleting for 50 cycles. The volume of methanol was reduced (~100 fold) by rotary evaporation and the resulting sample was analyzed by HPLC. 70 to 80% of the taxanes were generally recovered with 10-15% measurable decomposition. It was later found that exhaustive drying of the sample prior to soxhlet resulted in less than 5% degradation of taxol The extraction of solid media and callus was accomplished identically to that of cells when taxane levels were low, however, methylene chloride/IPA vs. water partitioning of the final methanol extract was always performed. When taxane levels exceeded ~5 mg/L the whole broth extraction method was employed to prepare samples of callus on solidified medium.

5.3. High Performance Liquid Chromatography Methods

Analytical high performance liquid chromatography (HPLC) was performed on a high-carbon loaded diphenyl column (Supelco, 5 mM, 4.6 mm×25 cm) with an LDC Analytical binary gradient high pressure mixing system consisting of CM3500/CM3200 pumps, a CM4100 variable volume autosampler and an SM5000 photo diode array detector interfaced to a personal computer. Column temperature was regulated at 35° C. with an Eldex CH150 column oven. Quantitative HPLC analysis of taxanes was accomplished using a binary gradient elution scheme as follows:

| Time | % Eluant A | % Eluant B | Flow |
|---|---|---|---|
| 0 | 75 | 25 | 1 mL/min |
| 40 | 35 | 65 | " |
| 42 | 25 | 75 | " |
| 47 | 25 | 75 | " |
| 50 | 75 | 25 | " |

Eluant A = 0.015 mM $KH_2PO_4$ brought to pH 3.5 with trifluoroacetic acid
Eluant B = acetonitrile The chromatographic methods used resemble several published methods (Witherup et al. 1989, *J. Liq. Chromatog.*, 12, 2117-2132) with the exceptions that a phosphate buffer containing trifluoroacetic acid has been used and that a longer gradient is employed. These differences significantly improve the resolution of taxol and other taxanes from the mixture. The relative retention times observed for taxanes are shown below. Taxol elutes between 31 and 33 minutes depending on the column and hardware used.

| Compound | Relative Retention Time |
|---|---|
| 10-deacetylbaccatin III | 0.38 |
| baccatin III | 0.56 |
| 7-xylosyl-10-deacetyltaxol | 0.80 |
| 10-deacetyltaxol | 0.87 |
| cephalomannine | 0.94 |
| 10-deacetyl-7-epitaxol | 0.98 |
| taxol | 1.00 |
| 7-epitaxol | 1.12 |

The retention times of taxol, cephalomannine and baccatin III were determined using authentic samples obtained from the National Cancer Institute. The retention times of the other taxanes listed above were compared to analytical standards provided by Hauser Chemical (Boulder, Colo.). Identification of known taxanes was based on retention time and ultraviolet spectral comparisons. Compounds that exhibited a UV spectrum similar to that of taxol and baccatin III, but that did not correlate to the relative retention times of these taxanes were considered taxanes. Quantitation of taxol, cephalomannine and baccatin III was based on response factors determined from authentic materials. Quantitation of 10-deacetylbaccatin III was performed using the response factor determined for baccatin III. Where appropriate, quantitation of the remaining taxanes was based on the response factors measured for taxol and baccatin III. The term total "taxanes" represents the sum of the taxanes that exhibited a characteristic UV similar to taxol and baccatin III. Total taxanes identified in *Taxus* cultures include, among others, 10-deacetylbaccatin III, 9-dihydrobaccatin III, 7-epi-10-deacetylbaccatin III, baccatin III, 9-dihydro-13-acetylbaccatin III, 7-xylosyl-10-deacetylcephalomannine, 7-xylosyl-10-deacetyltaxol, 7-epibaccatin III, 10-deacetyltaxol, 7-xylosyltaxol, cephalomannine, 7-epi-10-deacetltaxol, taxol, 2-benzoyl-2-deacetyl-1-hydroxybaccatin I, taxol C, 7-epitaxol, and 2-benzoyl-2-deacetylbaccatin I.

Taxanes that did not exhibit the characteristic UV absorbance, but did exhibit characteristics taxane-mass-fragmentation characteristics upon mass spectrometry, were also observed in *Taxus* cell cultures. Examples of such taxanes produced in *Taxus* cell cultures are, among others, Taxuyunnanine C, and its analogs and derivatives.

Each of the standards (10 μL) was typically injected (initially then after 3 or 4 samples) and areas for each of the three components were integrated from the 227 nm chromatogram. Response factors for each of the components was obtained by linear least-squares analysis of the data. 10 μL each sample was injected and the amount per injection was calculated based on the standard data regression. These results were converted to amount per liter or percent dry weight. FIG. 4 illustrates a typical chromatogram of a supernatant sample.

5.4 Rapid High Performance Liquid Chromatography Methods

In addition to the above method, several rapid methods of HPLC analysis were developed to allow greater sample throughput. Two of these methods are described in detail below.

Method 1). Rapid high performance liquid chromatography (HPLC) was performed on a Phenomenex Curosil-G column (5 μM, 4.6 mm×25 cm with 4.6 mm×3 cm guard) at ambient temperature using the hardware described above. Quantitative HPLC analysis of taxanes was accomplished using a binary gradient elution scheme as follows:

| Time | % Eluant A | % Eluant B | Flow |
|---|---|---|---|
| 0 | 60 | 40 | 1.5 mL/min |
| 10 | 25 | 75 | " |
| 11 | 25 | 75 | " |

Eluant A=0.01 mM $KH_2PO_4$ brought to pH 3.5 with trifluoroacetic acid

Eluant B=acetonitrile

The relative retention times observed for taxanes are shown below. Taxol elutes at about 8 minutes depending on the column and hardware used.

| Compound | Relative Retention Time |
|---|---|
| 10-deacetylbaccatin III | 0.42 |
| baccatin III | 0.61 |
| taxol | 1.00 |

Standards containing taxol, baccatin III and 10-deacetylbaccatin III were prepared at 50 mg/L, 10 mg/L, and 1 mg/L levels. A standard was injected initially and then after every ninth sample and areas for each of the three components were integrated from the 227 nm chromatogram. Response factors for each of the components was obtained by linear least-squares analysis of the data. 10 μL of each sample was injected and the amount per liter was calculated from the peak area based on the sample dilution and the standard data regression.

Method 2). Rapid high performance liquid chromatography (HPLC) was also performed on a Phenomenex IB-SIL Phenyl column (3 μM, 4.6 mm×15 cm with 4.6 mm×3 cm guard) at ambient temperature using the hardware described above. Quantitative HPLC analysis of taxanes was accomplished using a binary gradient elution scheme as follows:

| Time | % Eluant A | % Eluant B | Flow |
|---|---|---|---|
| 0 | 65 | 35 | 1.0 mL/min |
| 10 | 30 | 70 | " |
| 12 | 30 | 70 | " |

Eluant A=0.015 mM $KH_2PO_4$ brought to pH 3.5 with trifluoroacetic acid

Eluant B=acetonitrile

The relative retention times observed for taxanes are shown below. Taxol elutes at about 9.5 minutes depending on the column and hardware used.

| Compound | Relative Retention Time |
|---|---|
| 10-deacetylbaccatin III | 0.41 |
| baccatin III | 0.61 |
| taxol | 1.00 |

Quantitation was performed as described above.

Modifications of the above methods with respect to flow rate and gradient span and time were also found to perform suitable chromatography for plant cell culture analysis.

5.4. MS/MS Confirmation of Taxol

The identity of taxol in cell culture supernatant has been confirmed using an MS/MS method (as shown in FIG. 6) which couples flow injection with ion spray atmospheric pressure chemical ionization. Details of the procedures used for acquiring the data presented in FIG. 6 were as follows: Mass Spectrometer: Sciex API 3 triple quadrupole with an atmospheric pressure ionization source. Nitrogen was used as the curtain gas and argon was used as the collision gas for the CID spectra. Interface: Ion Spray interface producing ions by Ion Evaporation Ionization (Electrospray). Zero air was used as the nebulizer gas. LC Pump: ABI 140B dual syringe pump operating at 5 μL/minute. Solvents: 50/50 acetonitrile/H2O 2 mM NH4OAc+0.1% formic acid. Injection Volume: 5 μL, all spectra taken by flow injection analysis. This method provided unequivocal confirmation for the presence of taxol in cell culture samples, and also provided quantitation with excellent agreement to HPLC results.

Example 6

Taxol Production by Various Species

The taxol produced by cell cultures of various *Taxus* species is summarized in Table 5. Callus was cultivated for 20 days in the dark on the indicated solidified medium for each species. The cells and medium were dried and methanol-extracted together, and assayed by either ELISA or HPILC as indicated.

Example 7

7.1. Production in Growth Medium

The production of taxol and taxanes commenced within the first 2 days of transfer of *Taxus chinensis* cell line K-1 into growth Medium A. The maximum taxol observed was on day 15, at 8.81 μg/flask, which corresponds to 0.44 mg/liter taxol. Of this, 46.1% was present in the extracellular medium. On day 15, the total taxane concentration was 72.87 μg/flask, or 3.6 mg/liter, of which 58.6% was present in the extracellular medium. The viability of cells was always greater than 90% as measured by fluorescence staining (Example 4), suggesting that the presence of extracellular taxol and taxanes was due to secretion rather than due to cell lysis.

The production levels of taxol, baccatin III, and related taxanes have been characterized for numerous different cell lines under a number of different growth conditions (elaborated in Table 2 and in other examples) in which taxane biosynthesis is not enhanced. These collective data indicate that when cultures are cultivated under conditions optimized for growth, but not for taxane biosynthesis, taxol production levels are typically less than or equal to 0.5 mg/L, and always less than or equal to 2 mg/L; the taxol volumetric productivities typically range from 0.03 mg/L/day to 0.07 mg/L/day, and are always less than 0.3 mg/L/day. Similarly, baccatin III production levels are typically less than or equal to 0.5 mg/L, and always less than or equal to 1 mg/L; the baccatin III volumetric productivities are typically less than or equal to 0.03 mg/L/day, and always less than 0.15 mg/L/day. Similarly, total-taxane titers are typically less than 5 mg/L, and are always less than or equal to 20 mg/L; the total taxane volumetric productivities are typically less than 1 mg/L/day, and always less than 3 mg/L/day.

7.2. Medium Exchange for Productivity Enhancement

Figure 2A:
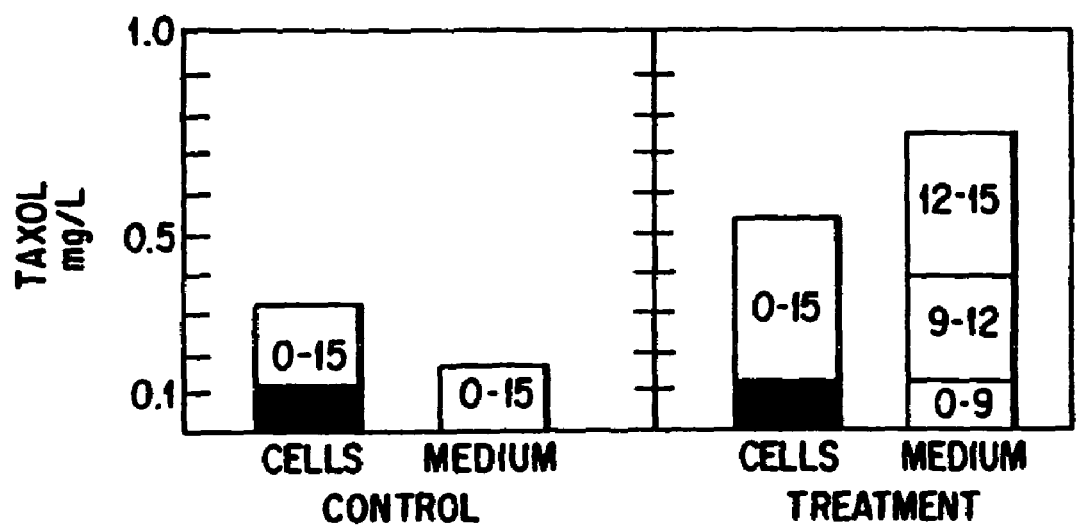
FIG. 2. Effect of medium exchange on days 9 and 12 on taxol (A) and total taxane (B) productivity in a 15-day experiment. The numbers in each box represent the time interval (days) over which the product was produced. The darkened portion of the intracellular boxes represents the taxol or total taxanes that were present in the cell inoculum at the start of the experiment. All treatments were performed in duplicate. *Taxus chinensis* suspension cell line K-1 was used with Medium A as elaborated in Table 2.
Figure 2B:
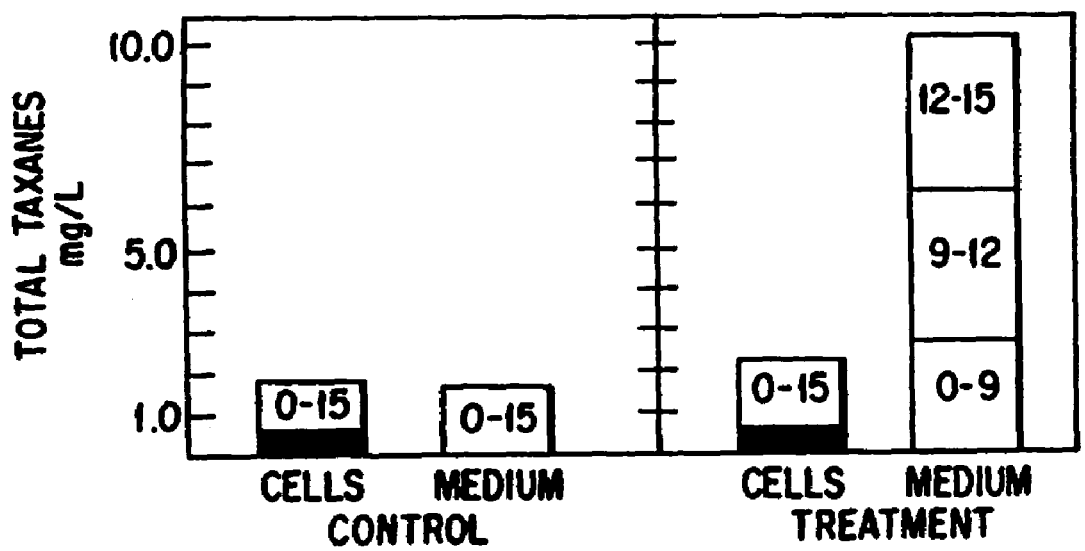

Significant improvements in taxol and total taxane productivity were obtained by aseptically suctioning off growth Medium A on day 9, replacing with fresh medium and repeating the procedure on day 12. The experiment was terminated on day 15, and the results are shown in FIG. 2. The important increases in productivity due to medium exchange are summarized in Table 6. The total amounts of taxol and taxanes produced were ca. 4.6-fold higher with medium exchange compared to controls without treatment. Importantly, ca. 4.9-fold higher taxol, and ca. 5.9-fold higher total taxanes were recovered in the extracellular medium compared to controls without medium exchange treatment.

The ability to markedly enhance taxol and total taxane productivities, and moreover, to cause extracellular product accumulation is important for operation of an efficient, continuous process with biomass reuse and simplified downstream purification.

7.3. Effect of Light on Taxane Production in Growth Medium

Light is known to play an important role not only in photosynthesis, but also in various aspects of secondary metabolism in plant cell cultures (Seibert and Kadkade 1980). Whereas the experiments described in Examples 4, 7.1, and 7.2 were conducted in darkness, the response of *Taxus chinensis* cultures to light is described here.

Figure 3:
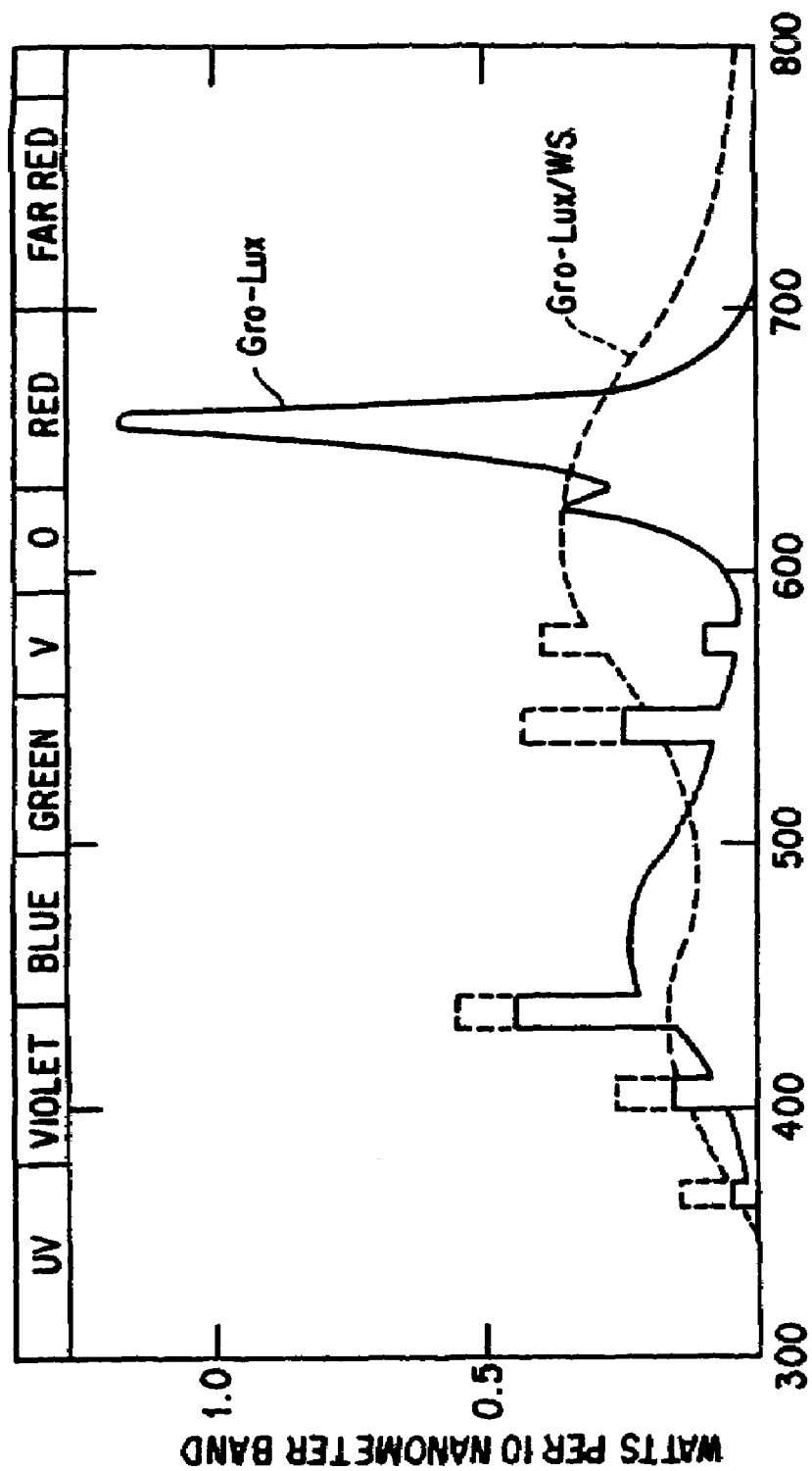
FIG. 3. Spectral characteristics of a Standard Gro-Lux lamp (GTE Sylvania, Danvers, Mass.) used in Example 7.3.
Figure 4A:
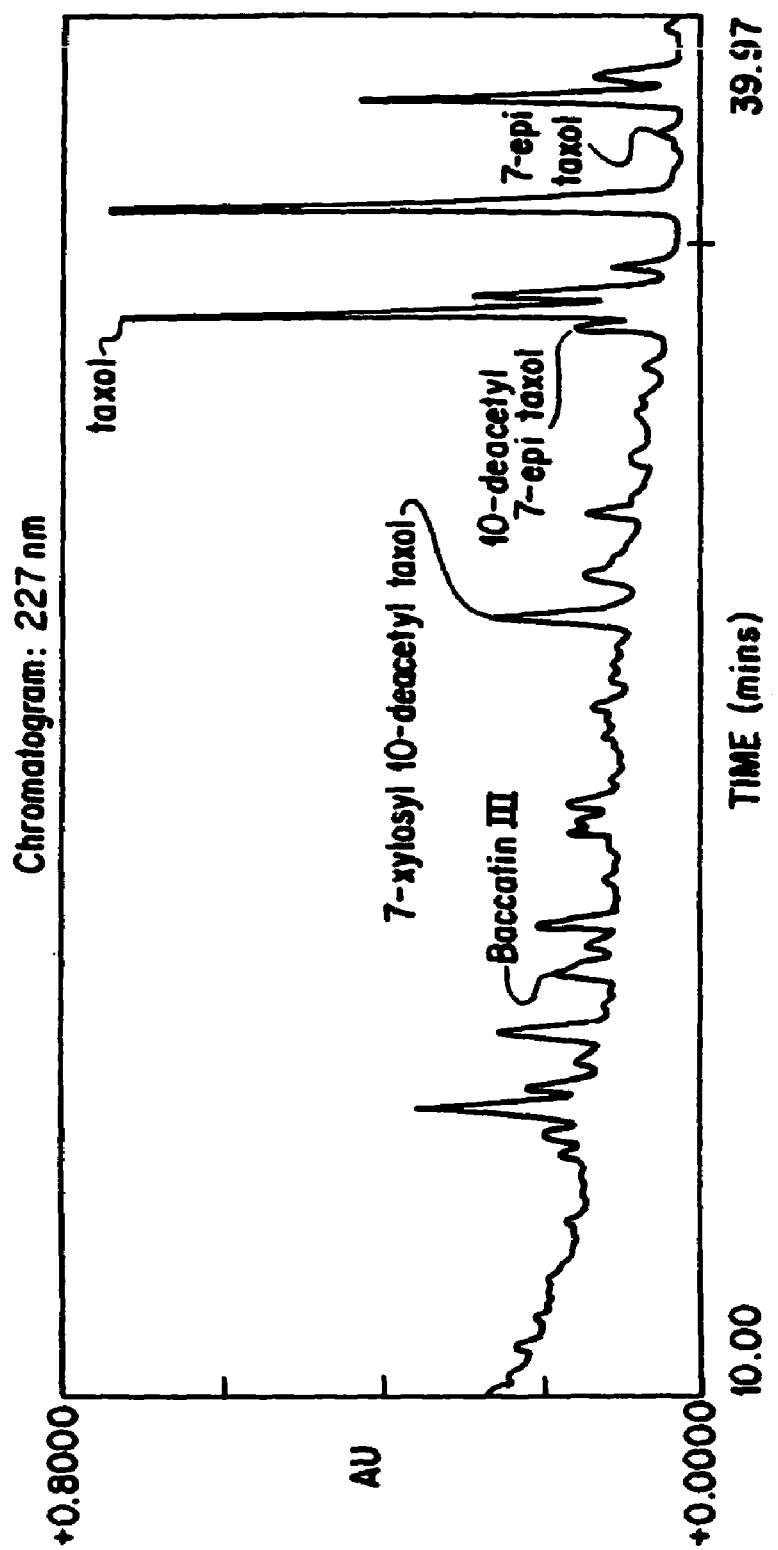
FIG. 4. Taxane production in *Taxus chinensis* cell suspension K-1. The portion of the chromatogram from 10 to 40 minutes is shown. Diode array scans of selected taxane peaks show a characteristic taxane UV absorption spectrum, with a peak at 227 nm.
Figure 4B:
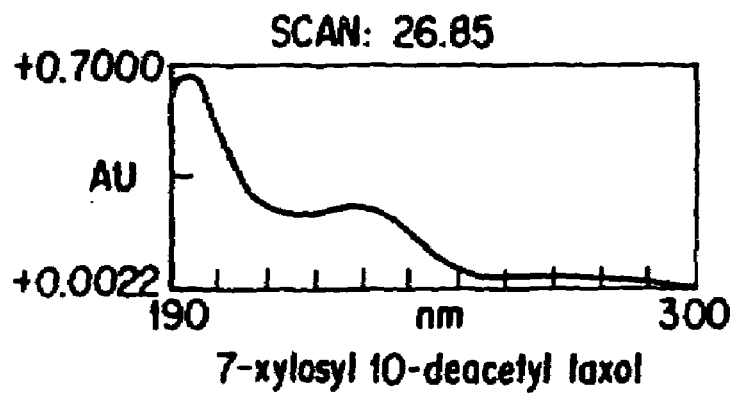
Figure 4C:
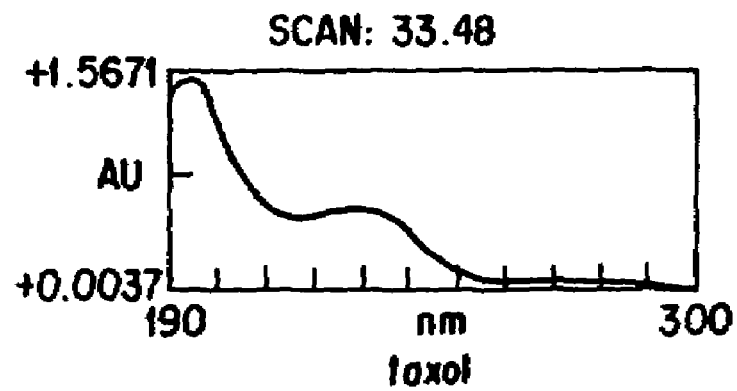
Figure 4D:
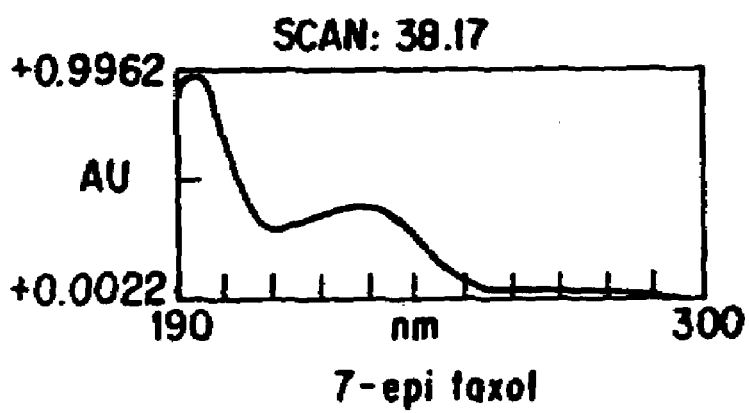

One gram fresh weight of 7-day old cells of *Taxus chinensis* line K-1 were inoculated in 25 ml of growth Medium A (see Table 2) in 125 ml Erlenmeyer flasks and incubated at 24±1° C. on a gyratory shaker at 120 rpm. Duplicate flasks were placed in the dark and under a Standard GroLux lamp at a distance of 3 feet. Spectral characteristics of the lamp are shown in FIG. 3. Results are shown in Table 7.

Exposure of cultures to light did not affect total taxane levels or the extent of extracellular accumulation. However, taxane profiles were significantly altered in the two treatments. For example, cells cultivated in the light produced 2.8 fold higher taxol than did cells in the dark. The proportion of extracellular taxol was also significantly higher than in the dark treatment (76% vs 56%). The use of light treatment, especially of specific spectral quality, might be useful in a cell culture process for taxol production.

Example 8

Elicitors

The term elicitors is used for compounds of biological (or biotic) and non-biological (or abiotic) origin that cause an increase in secondary metabolism when added to plant cell cultures.

While a number of elicitors have been found useful, a representative illustrative example is described here in detail, namely, the use of chitosan glutamate. While chitosan has been previously tried as an elicitor in some plant cell culture systems, the accompanying toxic reactions such as browning and loss of viability have made its use impractical (Beaumont and Knorr 1987, *Biotechnol. Lett.* 9, 377-382). Indeed such toxic side reactions are a common drawback of many elicitors reported in the literature. The use of chemically modified chitosans such as chitosan glutamate to specifically induce taxol and taxane biosynthesis while circumventing toxic side-effects is a novel approach.

Suspensions of *Taxus chinensis* line K-1 grown in Medium D for 7 to 8 days were suction filtered aseptically using a sterile Buchner funnel fitted with a miracloth (Calbiochem) filter. 2 g fresh weight cells were aseptically transferred to 25 ml of medium C (see Table 2) in a 125-mL Erlenmeyer flask. A solution of 0.05% chitosan glutamate was prepared freshly and filter-sterilized through a 0.22 micron cartridge filter. 825 µL of this solution was added to the flask at the start of the experiment, corresponding to a level of 165 mg elicitor per gram dry weight cells. The flasks were incubated at 24±1° C. on a gyratory shaker at 110 rpm in the dark. The flasks were destructively sampled on day 15, and observations on growth, color of the cells and medium and cell viability were recorded. Samples were analyzed for taxanes as described in Example 5. The results of this experiment are shown in Table 8.

Elicitor treatment resulted in a modest improvement in the per-cell total taxane production (0.53% vs. 0.42% dry weight taxanes) over non-treated controls. The non-toxic nature of the elicitor is evident from the high viabilities (75-80%) observed in both treatments. In fact, an increased dry weight in elicitor treatment compared to controls has been reproducibly observed (14.2 g/l vs. 10.1 g/l dry weight). The higher cell densities resulted in an 1.8-fold greater titer of total taxanes in the elicitor treatment, i.e., 75.8 mg/L versus 42.4 mg/L for the control.

The elicitor treatment resulted in increased taxol biosynthesis, both on a per-cell basis (0.098% vs. 0.054% dry weight taxol, a 1.8-fold increase) and in a titer comparison (13.9 mg/L versus 5.4 mg/L, a 2.6-fold increase). The extent of secretion was higher for the elicitor treatment compared to the control (85% versus 72% extracellular product).

The elicitor treatment described herein results in increased taxol production, a more favorable product profile, enhanced product secretion and retention of high cell viability. These production characteristics represent a significant improvement for a cell culture process for taxol production.

Example 9

Production Medium Development

In an effort to increase taxol productivities over the levels described in example 6, nutrient levels were manipulated to formulate special 'production media'. 7 to 8 day old suspensions of *Taxus chinensis* line K-1 grown in Medium D were suction filtered aseptically using a sterile Buchner funnel fitted with a MIRACLOTH (rayon polyester cloth with acrylic binder) filter (Calbiochem). 500 mg fresh weight cells were aseptically transferred to 5 ml of production Media B and C (see Table 2). The vessels were incubated for varying time periods of 18, 25, and 42 days at 24±1° C. on a gyratory shaker at 110 rpm in the dark. Treatments were destructively sampled, and observations on growth, color of the cells and medium, and cell viability were recorded. Samples were analyzed for taxanes as described in Example 5. The results of this experiment are shown in Table 9.

9.1. Results of 18-Day Cultivation

*Taxus chinensis* cell cultures responded to the altered medium compositions by producing significant levels of taxanes and taxol. These data are summarized in Table 9, and a sample chromatogram is shown in FIG. 4. In medium B, 99.8 mg/liter of total taxanes were produced, with 24.1 mg/liter of taxol. In Medium C, 110 mg/liter of total taxanes were produced, with 21.3 mg/liter of taxol. On a dry weight basis, cells produced 0.18% dry weight taxol on medium B, and 0.065% dry weight taxol on medium C.

9.2. Prolonged Cultivation

Figure 5B:
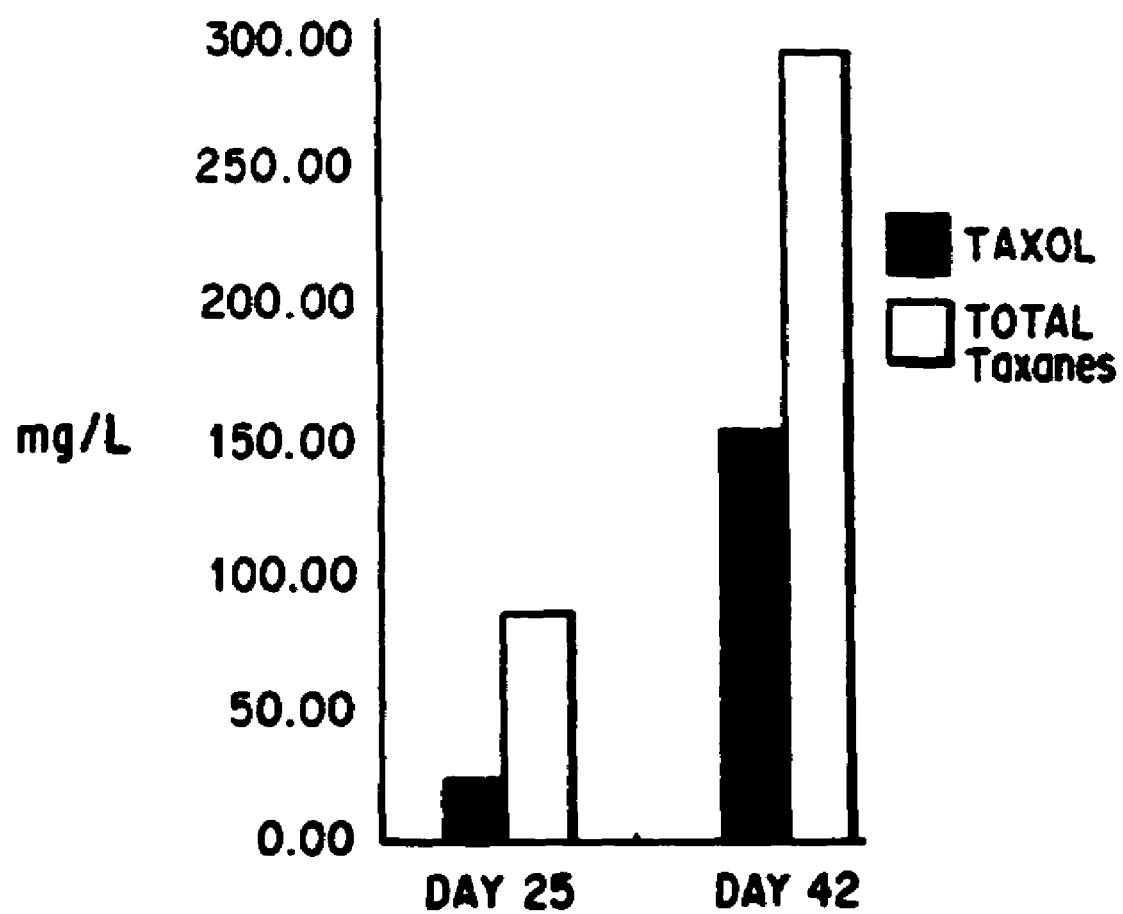
FIG. 5. Taxol and taxane production after prolonged cultivation in Medium by *Taxus chinensis* cell line K-1. Panel A tabulates the data for the known and unknown taxanes, whereas Panel B shows incremental taxol and taxane production in the 25 to 42 day time period.
Figure 6A:
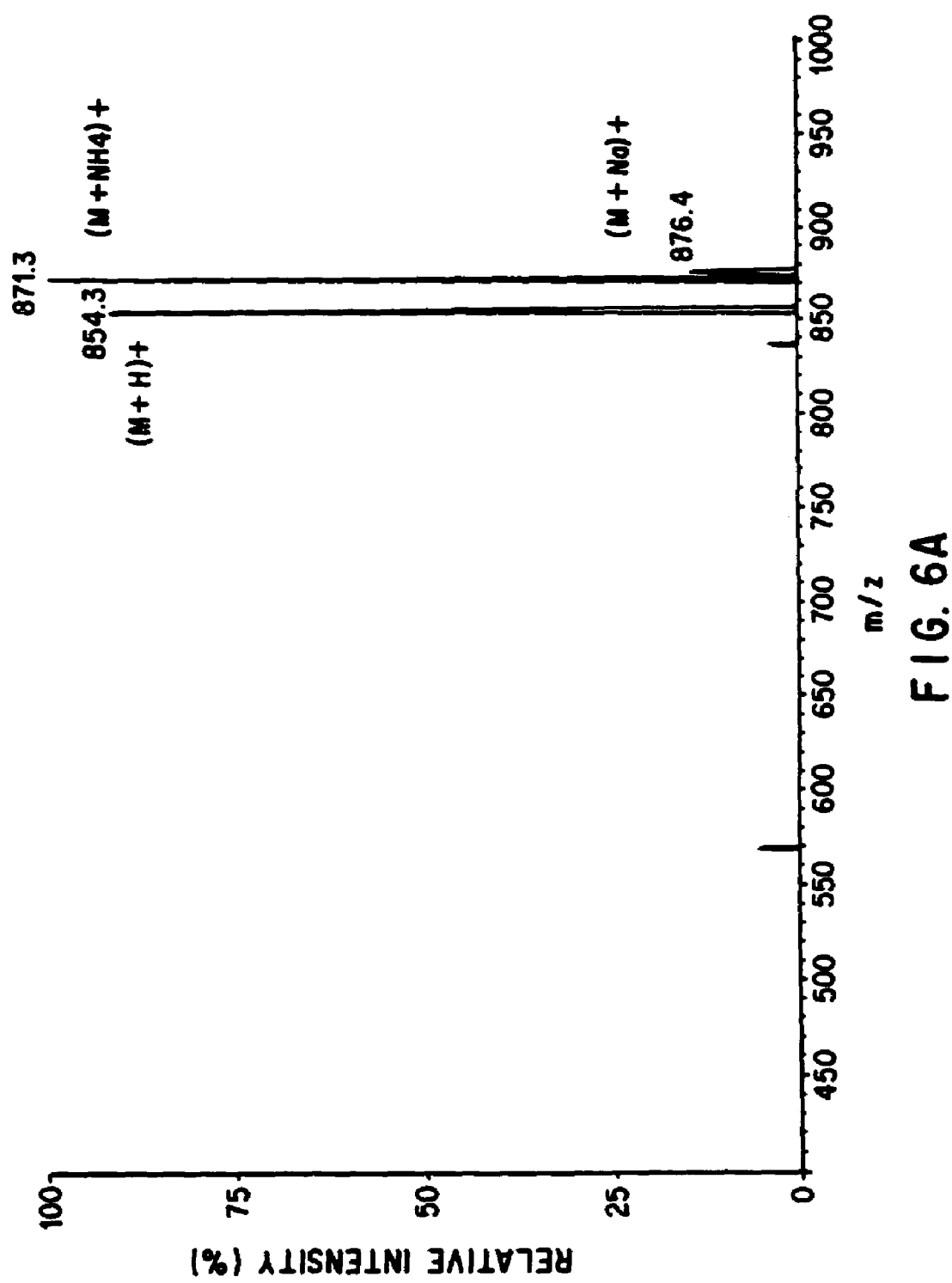
FIG. 6. MS/MS confirmation of taxol in cell culture supernatant. Panel A shows the ion spray APCI mass spectrum of authentic taxol and panel B shows the daughter ion spectrum of the parent peak (m/z 871=taxol+NH4+). Panel C represents the ion spray APCI spectrum from a crude cell culture extract and shows m/z 854 and 871 characteristic of taxol. Panel D shows the corresponding daughter spectrum of m/z 871 and provides unequivocal evidence for the presence of taxol in cell culture supernatant.
Figure 6B:
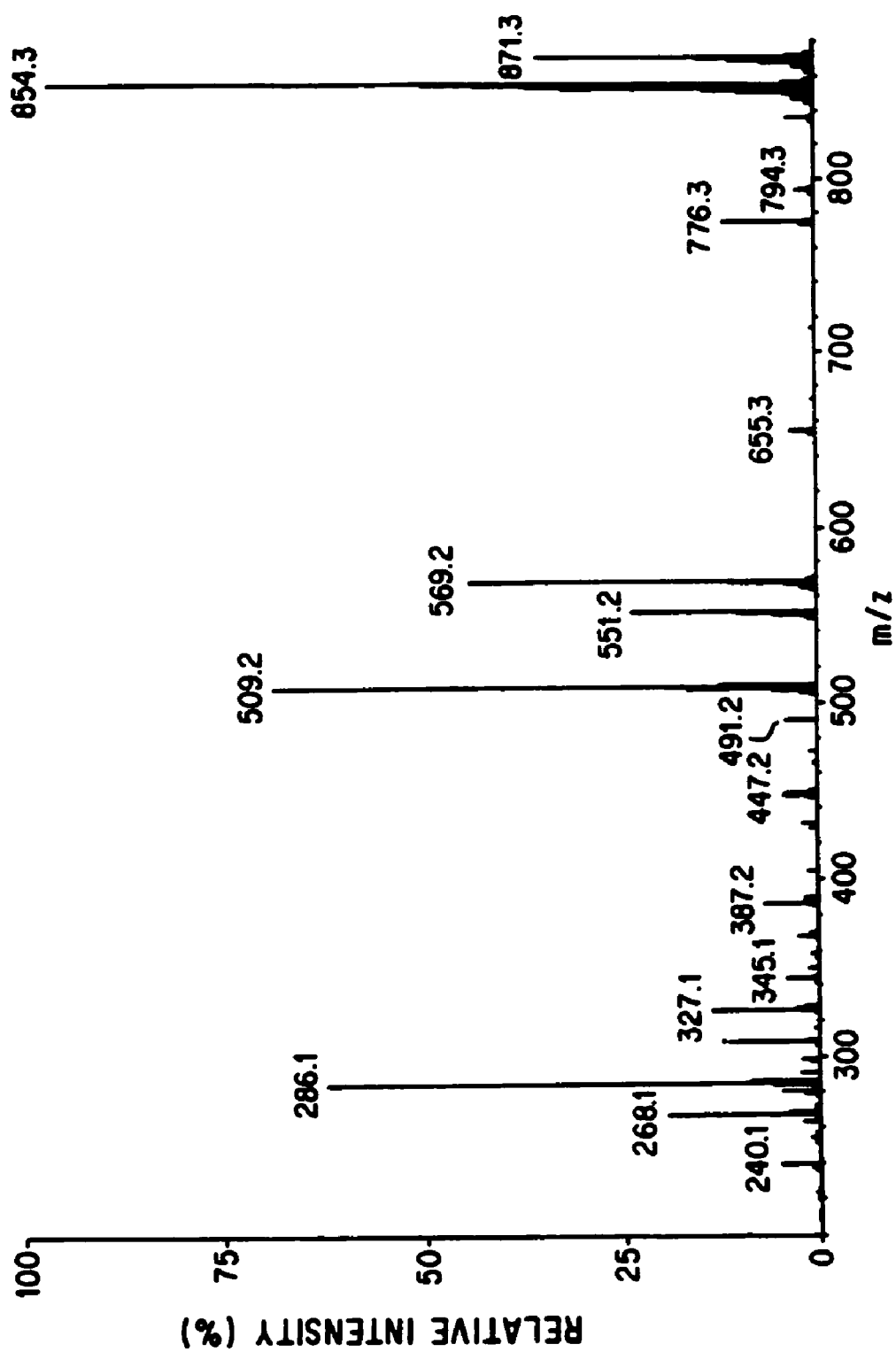
Figure 6C:
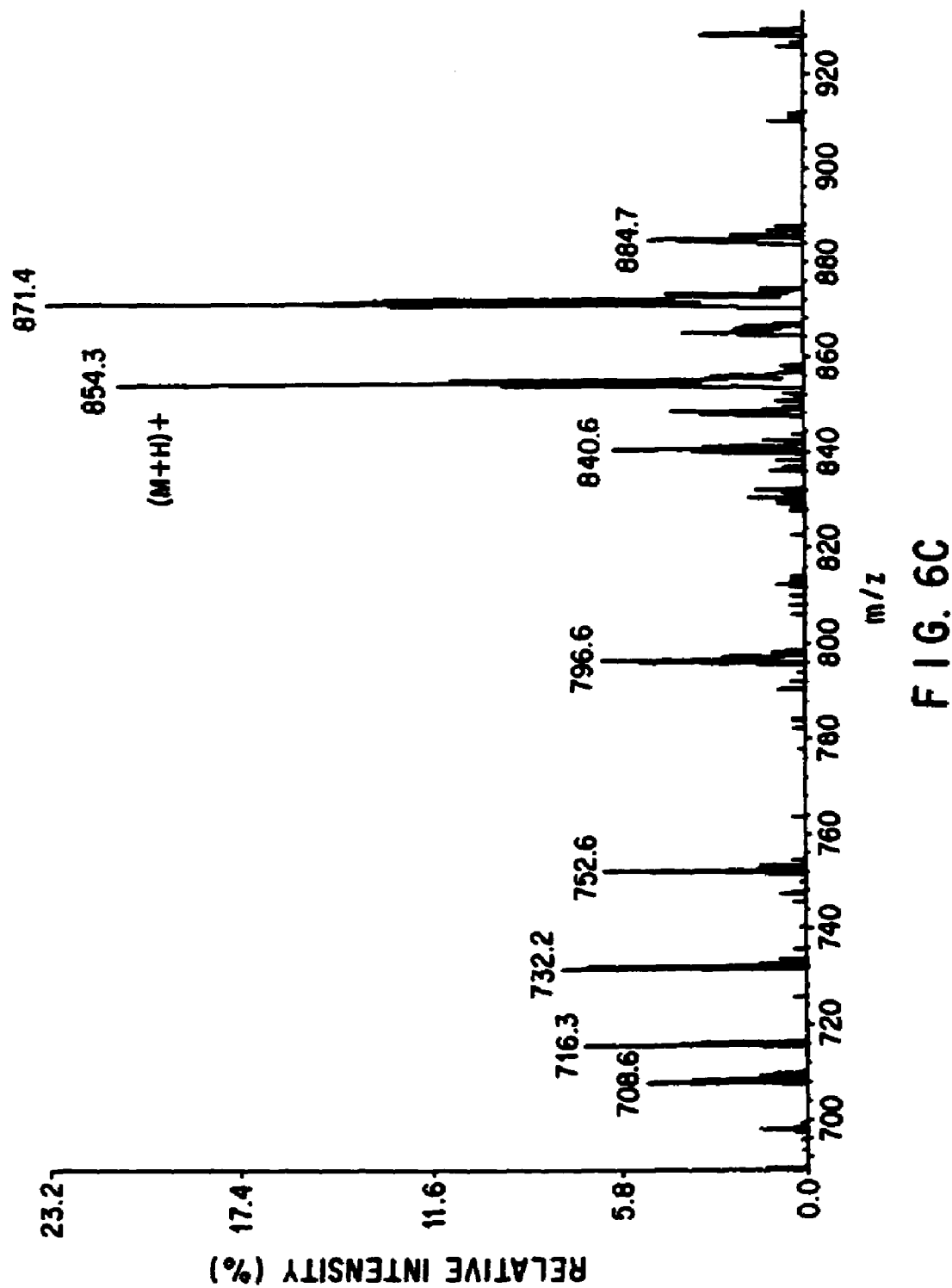
Figure 6D:
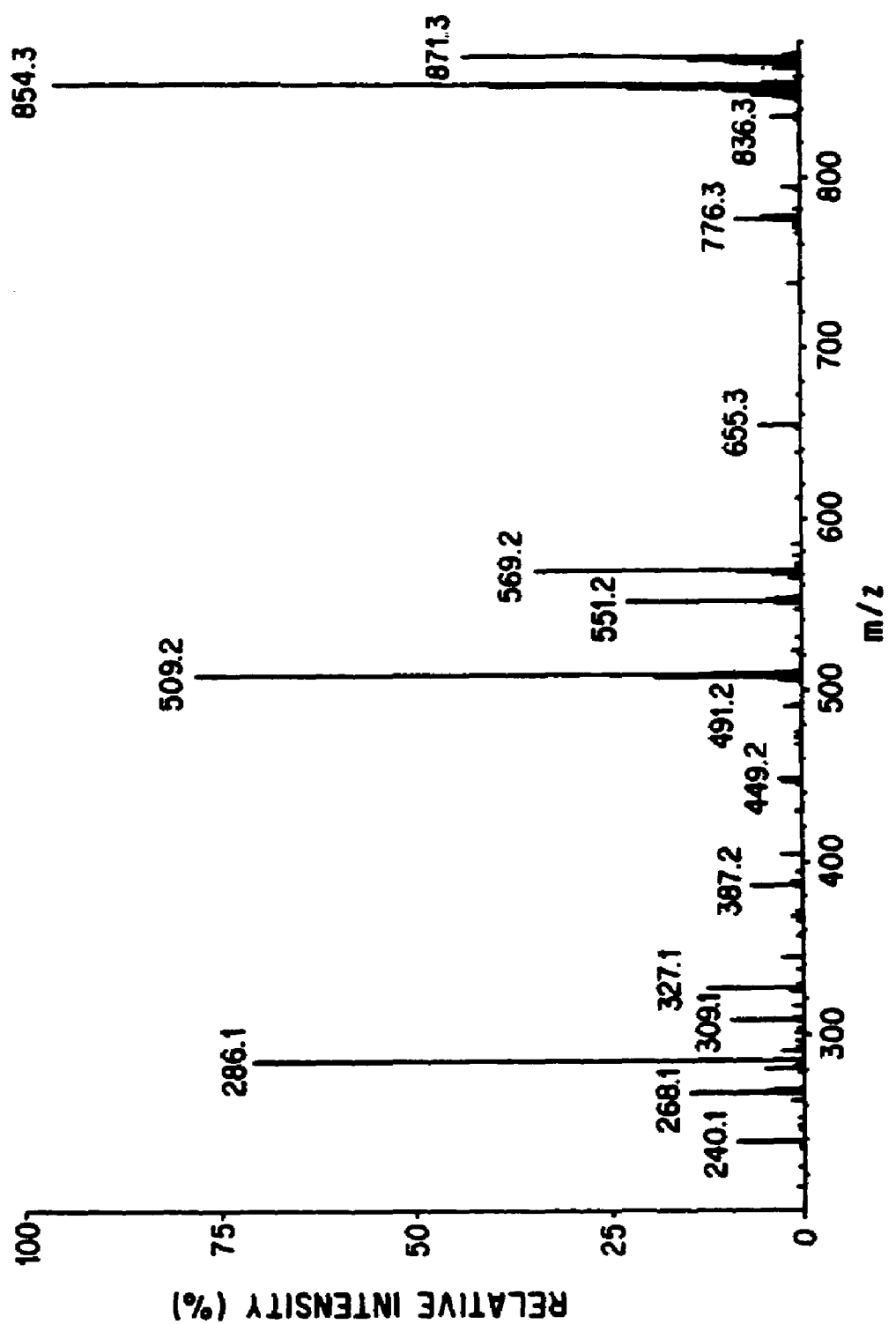

Taxol and taxane production after prolonged cultivation of *Taxus chinensis* cells (line K-1) for 25 and 42 days was studied in medium C, the results for which are summarized in FIG. 5. The following significant observations can be summarized:

(i) *Taxus* suspension cultures are capable of producing significant levels of taxol and other taxanes. Highest accumulation occurred at 42 days, with 0.32% dry weight taxol, and 0.62% dry weight total taxanes; corresponding to titers of 153 mg/L taxol and 295 mg/L total taxanes based on final medium volume. The analysis of this sample by tandem mass spectrometry confirmed the presence of taxol as shown in FIG. 6. Quantitation by MS/MS showed excellent agreement with HPLC.

(ii) The rate of taxol biosynthesis between days 25 and 42 was at ca. 7.6 mg taxol per liter per day assuming linear production in the 17-day period. This rate is significantly higher than the rate of production in the first 25 days. The rate of total taxane biosynthesis between days 25 and 42 was 12.3 mg per liter per day. The average volumetric productivities for taxol, baccatin 111, and total taxanes were 3.6, 0.5, and 7.0 mg/L/day respectively.

(iii) Production medium formulations can induce up to 45-fold increases in specific taxol content compared to rapid-growth conditions (in which taxane biosynthesis is unenhanced) such as those described in Example 7.

(iv) The product spectrum can be manipulated so as to funnel biosynthesis towards the desired end-product taxol, while minimizing production of undesirable taxanes. For example, on day 25, taxol constituted 28% of the total taxanes and on day 42, taxol constituted 52% of the total taxanes in contrast to growth medium (see Example 7.1), in which taxol constituted only 12.2% of the total taxanes. This ability to manipulate product profiles will have important repercussions for downstream purification and for product purity-related regulatory issues. For example, the ability to suppress production of the taxane by-product, cephalomannine could greatly simplify downstream purification compared to purification of taxol from bark tissue.

(v) *Taxus* cell cultures have been induced to secrete significant amounts of taxol (87% on day 42) and other taxanes. That the presence of extracellular taxol and taxanes is due to secretion rather than due to cell lysis is corroborated by several independent observations: (a) Continued biosynthesis occurred between days 25 and 42, suggesting that cells were viable and active. Independent observations have shown that >70% viability have been observed after 18 days in production medium. (b) Different percentages of different taxanes were secreted. If cells had lysed, the percentage in the medium might have been expected to be similar for the different taxanes.

(vi) The ability of this *Taxus* cell line to thrive and produce taxol at high rates in an extracellular environment so rich in product is particularly worth noting.

(vii) The *Taxus* cell line with which these results were obtained is also capable of rapid growth to high cell densities, and expressed the reported productivities after 20 generations under rapid-growth conditions, attesting to its stability and commercial potential.

The levels of taxol and taxanes produced by cell lines of *Taxus chinensis* under the conditions described herein are higher than previously reported results by a factor of 35- to 150-fold. For example, Christen et al. (1991) reported the production of 1 to 3 mg/liter of taxol by suspension cultures of *Taxus brevifolia* after 2 to 4 weeks of cultivation. Wickeramesinhe and Arteca (1991) reported the production of taxol at 0.009% dry weight in cell cultures of *Taxus media*.

In summary, our data show that with careful initiation and selection of *Taxus chinensis* cultures, and with specially formulated growth medium conditions, cells can be induced to grow rapidly to high cell densities. When these cells are transferred to production medium conditions, cells are able to biosynthesize and secrete significant levels of taxol and other taxanes for prolonged periods while maintaining high viabilities. The incorporation of periodic medium exchange, light and elicitors with production medium results in further synergistic productivity enhancements. These properties are critical prerequisites for an efficient commercial process for taxol and taxane production using tissue culture technology.

Example 10

10.1. Enhancement of Taxane Production Using Silver

Silver, in the form of silver containing compounds, silver complexes, or silver ions, was found to be a useful enhancement agent of taxol, baccatin III, and taxane biosynthesis in cell cultures of *Taxus* species. The combination of silver and other enhancement agents has also been found to be useful in obtaining and sustaining high rates of taxane production.

Seven-day old cells of *Taxus chinensis* suspension KS1A cultivated in Medium L (Table 2) were suction filtered aseptically using a sterile Buchner funnel fitted with a MIRACLOTH (Calbiochem) filter. Approximately 0.75 to 1 gram fresh weight cells were inoculated into 4 to 5 mL of culture medium of the given composition indicated in Table 10, to yield a fresh weight cell density in the range of 15% to 20% (w/v). The vessels were incubated at 25±1° C. at 120 RPM on a gyratory shaker (1" throw) in the dark. Evaporation was corrected for by addition of sterile distilled water. Samples of whole broth (i.e., both extracellular and intracellular taxanes) were taken at periodic intervals, and were processed and analyzed by HPLC according to the methods outlined in Example 5.

The data summarized in Table 10 indicate that the production of taxol, baccatin III, and other taxanes can be successfully enhanced by a variety of silver containing compounds. This enhancement is due primarily to the presence of silver in the medium, as demonstrated in Table 10, which shows enhancement for a variety of different silver containing compounds and different counterions. These levels of production are significantly higher than that observed in unenhanced cultures (the production levels for which are elaborated in Example 7).

10.2. Enhancement of Taxane Production Using Silver Thiosulfate

Based on considerations of toxicity and ease of preparation and storage, silver thiosulfate was used in subsequent experiments. The method used for the preparation of silver thiosulfate was as follows: 1.98 grams of sodium thiosulfate (pentahydrate) was dissolved in 80 mL of water. 20 mL of a 0.1M solution of silver nitrate was added while stirring vigorously, resulting in 100 mL of a 20 mM stock solution of silver thiosulfate. Potassium thiosulfate could be used in place of sodium thiosulfate with equally efficacious results. The stock solutions were filter-sterilized using 0.22 μM cartridge filters into cell culture media at the start of a given experiment. Alternative methods for preparing similar silver thiosulfate solutions are also suitable. The cell culture protocols were similar to those described for the experiments described in Table 10.

Table 11 summarizes data obtained by using silver as an enhancement agent for a number of different cell cultures of *Taxus chinensis*. These data show that silver effects a fundamental enhancement of taxane biosynthesis generally. The specific product profile observed in any given case reflects characteristics of the cell line and the culture medium. Silver ion/complex can be particularly effective in enhancing taxane production when used in conjunction with other factors in the medium favoring biosynthesis such as growth regulators, carbon source, salts, micronutrients, and the like.

Example 11

Enhancement of Taxane Production Using Methyl Jasmonate and Jasmonate-Related Compounds The methyl ester of jasmonic acid (methyl jasmonate), as well as jasmonic acid and related compounds, were found to be useful as enhancement agents of taxane biosynthesis in cell cultures of *Taxus* species. The combination of methyl jasmonate and other enhancement agents has also been found to be useful in obtaining and sustaining high rates of taxane production.

Seven-day old cells of *Taxus chinensis* suspensions cultivated in Medium M (Table 2) were suction filtered aseptically using a sterile Buchner funnel fitted with a MIRACLOTH (Calbiochem) filter. Cells were inoculated into culture medium of the given composition indicated in Table 12, at a fresh weight cell density in the range of 15% to 20% (w/v). The cultures were incubated at 24±1° C. at 120 or 180 RPM (depending on the vessel size) on a gyratory shaker (1" throw) in the dark. Evaporation was corrected for by adding sterile distilled water. Samples of whole broth (i.e., both extracellular and intracellular taxanes) were taken at periodic intervals, and were processed and analyzed by HPLC according to the methods outlined in Example 5.

Table 12 summarizes data obtained by using jasmonic acid and its methyl ester as enhancement agents for several representative *Taxus chinensis* cell lines. These data show that jasmonic acid and its methyl ester effect a fundamental enhancement of taxane biosynthesis generally. The specific product profile observed in any given case reflects characteristics of the cell line and the culture medium. These levels of production obtained in the presence of these enhancing agents are significantly higher than that observed in unenhanced cultures (the production levels for which are elaborated in Example 7).

Jasmonic acid, its methyl ester, and related compounds, are effective enhancement agents of taxane biosynthesis when used in conjunction with other factors in the medium favoring biosynthesis such as other enhancement agents, growth regulators, carbon source, salts, micronutrients, and the like.

Example 12

Enhancement of Taxane Production Using 3,4-Methylenedioxy-6-nitrocinnamic acid

The cinnamic acid analog, 3,4-methylenedioxy-6-nitrocinnamic acid (MDNA) and related compounds were found to be useful enhancement agents of taxane biosynthesis in cell cultures of *Taxus* species. The combination of MDNA and other enhancement agents has also been found to be useful in obtaining and sustaining high rates of taxane production.

Seven-day old cells of *Taxus chinensis* suspension culture SS122-42 cultivated in Medium M (Table 2) were suction filtered aseptically using a sterile Buchner funnel fitted with a MIRACLOTH (Calbiochem) filter. Cells were inoculated into culture medium conditions at a fresh weight density of 15% to 20% (w/v). The vessels were incubated at 24±1° C. at 180 RPM on a gyratory shaker (1" throw) in the dark. Treated cultures were sampled and analyzed using the methods described in Example 5 at various time points. Evaporation was corrected for by adding sterile distilled water at periodic intervals. Samples of whole broth (i.e., both extracellular and intracellular taxanes) were taken at periodic intervals, and were processed and analyzed by HPLC according to the methods outlined in Example 5.

Table 13 summarizes data obtained by using 3,4-methylenedioxynitrocinnamic acid as an enhancement agent for taxane biosynthesis in *Taxus chinensis* cell cultures. These data show that MDNA effects a fundamental enhancement of taxane biosynthesis generally. Cultivation in Medium II i.e., in the presence of MDNA and silver, further enhances the production of taxanes. The specific product profile observed in any given case reflects characteristics of the cell line and the culture medium. These levels of production are significantly higher than that observed in unenhanced cultures (the production levels for which are elaborated in Example 7).

Example 13

Enhancement of Taxane Biosynthesis Using a Combination of Enhancement Agents

Various enhancement agents, used in combination, gave significant and synergistic improvements in taxane production.

Seven-day old cells of *Taxus chinensis* suspension cultures cultivated in Medium P (SS64-412), Medium O (SS64-561, SS64-571), Medium I (SS124-77, SS85-26), Medium M (SS122-29) (the composition of these media are listed in Table 2) were suction filtered aseptically using a sterile Buchner funnel fitted with a MIRACLOTH (Calbiochem) filter. Cells were inoculated into culture medium (indicated in Table 14) at a fresh weight density of 20% (w/v). The cultures were incubated at 24±1° C. at 180 RPM on a gyratory shaker (1" throw) in the dark. Evaporation was corrected for by adding sterile distilled water at periodic intervals. Samples of whole broth (i.e., both extracellular and intracellular taxanes) were taken at periodic intervals, and were processed and analyzed by HPLC according to the methods outlined in Example 5.

Table 14 summarizes data obtained by using various combinations of enhancement agents for taxol, baccatin III, and taxane biosynthesis in *Taxus chinensis* cell cultures. The data demonstrates substantial further enhancement of taxane production by combinations of enhancement agents over that seen for individual agents, and over production levels in unenhanced conditions (the production levels for which are elaborated in Example 7).

Example 14

Enhancement of Taxane Production by Medium Exchange

This example demonstrates that high productivity in culture can be sustained by replenishing medium components and removing spent medium.

Cell lines were initially cultivated in Medium O (Paella), Medium I (SS29-3A5), and Medium I (SS45-146). The detailed compositions of these cultivation media are described in Table 2. Seven day-old cells of these cell lines were suction-filtered aseptically using a sterile Buchner funnel fitted with a MIRACLOTH (Calbiochem) filter. Approximately 1.5 grams fresh weight cells were inoculated into 4.25 mL of the respective culture media indicated in Table 15. The vessels were incubated at 24±1° C. at 120 RPM on a gyratory shaker (1" throw) in the dark. Evaporation was corrected for by addition of sterile distilled water at periodic intervals. For the medium exchange treatments, the spent production medium was suctioned off using a sterile pipette after 10 to 11 days of batch cultivation, leaving the cells behind in the vessel. The spent supernatant was analyzed for extracellular taxanes using the methods described in Example 5. Fresh culture medium of the same composition as the first batch culture was added to the vessel containing productive cells. The cells were cultured under the same environmental conditions described above. The medium exchange cycle was repeated after an additional 10 to 11 days of cultivation. The total extracellular taxanes for batch production is compared with that of medium exchange production in Table 15. The medium exchange concentration values denote the total amount of taxane produced in the extracellular medium divided by the volume of the cell suspension culture (i.e., 5.75 mL).

Table 15 indicates that cells can be sustained in a productive state for a prolonged period, and in fact, that productivity of the cells can be enhanced by repeated medium exchange. Enhancement by repeated medium exchange is feasible using a range of different enhancement conditions, and with a variety of cell cultures.

The data demonstrates substantial further enhancement of taxane production over production levels in unenhanced conditions (the production levels for which are elaborated in Example 7).

Example 15

Enhancement of Taxane Production by Fed Batch Operation

Seven day-old cells of cell lines cultivated in Medium I (CR-128, SS36-245), Medium L (SS36-359) (the compositions of these media are described in Table 2) were suction filtered aseptically using a sterile Buchner funnel fitted with a MIRACLOTH (Calbiochem) filter. Approximately 1 gram fresh weight of cells were inoculated into 4 ml of culture medium of the given composition indicated in Table 16.a. The vessels were incubated at 24±1° C. at 120 RPM on a gyratory shaker (1" throw) in the dark. Evaporation was corrected for by addition of sterile distilled water at periodic intervals. For fed batch operation, sterile feed solutions of predetermined compositions were fed continuously into the culture vessels at predetermined rates of feeding, e.g. 10 mL feed solution per liter of culture per day. Details of the fed batch operation are described in Table 16.b., including compositions of the feed solutions and feeding protocols. Treated cultures were sampled and analyzed using the methods described in Example 5.

Table 16.a. indicates that cells can be sustained in a productive state for a prolonged period, and in fact, that productivity of the cells can be enhanced by fed batch operation, resulting in the accumulation of high levels of baccatin III, taxol, and other taxanes. The relative amounts of particular taxanes reflect the interaction of feeding protocol and feed composition with the cell line and culture conditions. This Table also indicates that feeding phenylalanine results in enhanced production of taxol relative to other taxanes.

The data demonstrates substantial further enhancement of taxane production over production levels in unenhanced conditions (the production levels for which are elaborated in Example 7).

Example 16

Enhancement of Taxane Biosynthesis Using a Combination of Enhancement Agents

Various enhancement agents, used in combination, gave significant and synergistic improvements in taxol, baccatin III, and taxane production.

Seven-day old cells of *Taxus chinensis* suspension cultures (SS122-41, cr427, SS122-30, cr857, cr452) cultivated in Medium M (the composition of the medium is listed in Table 2) were suction filtered aseptically using a sterile Buchner funnel fitted with a MIRACLOTH (Calbiochem) filter. Cells were inoculated into culture medium (indicated in Table 17) at a fresh weight density of 20% (w/v) unless described otherwise in Table 17. The cultures were incubated at 24±1° C. at 180 RPM on a gyratory shaker (1" throw) in the dark. Evaporation was corrected for by adding sterile distilled water as necessary. Samples of whole broth (i.e., both extracellular and intracellular taxanes) were taken at periodic intervals, and were processed and analyzed by HPLC according to the methods outlined in Example 5.

Table 17 summarizes data obtained by using various combinations of enhancement agents for taxol and taxane biosynthesis in *Taxus chinensis* cell cultures. The data demonstrates substantial further enhancement of taxane production by combinations of enhancement agents over that seen for individual agents, and over unenhanced conditions (the details of which are provided in Example 7).

Example 17

Enhancement of Taxane Production by Fed Batch Operation

Seven-day old cells of cell lines cultivated in Medium M (SS122-41) (the compositions of these media are described in Table 2) were suction filtered aseptically using a sterile Buchner funnel fitted with a Miracloth (Calbiochem) filter. Approximately 1 gram fresh weight of cells were inoculated into 4 ml of culture medium of the given composition indicated in Table 18.a. The vessels were incubated at 24±2° C. at 120 RPM on a gyratory shaker (1 throw) in the dark. Evaporation was corrected for by addition of sterile distilled water. For fed batch operation, sterile feed solutions of predetermined compositions were fed continuously into the culture vessels. Details of the fed batch operation, including compositions of the feed solutions and feeding protocols are described in Table 18.b. Treated cultures were sampled and analyzed using the methods described in Example 5.

Table 18.a. indicates that cells can be sustained in a productive state for a prolonged period, and in fact, that volumetric productivity of the cells can be enhanced by fed batch operation, resulting in the accumulation of high levels of baccatin III, taxol, and other taxanes. The relative amounts of particular taxanes reflect the interaction of feeding protocol and feed composition with the cell line and culture conditions.

The data demonstrates substantial further enhancement of taxane production over production levels in unenhanced conditions (the production levels for which are elaborated in Example 7).

For purposes of clarity of understanding, the foregoing invention has been described in some detail by way of illustration and example in conjunction with specific embodiments, although other aspects, advantages and modifications will be apparent to those skilled in the art to which the invention pertains. The foregoing description and examples are intended to illustrate, but not limit the scope of the invention. Modifications of the above-described modes for carrying out the invention that are apparent to persons skilled in the art are intended to be within the scope of the invention, which is limited only by the appended claims.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

TABLE 1.a.

List of Elicitors Used in Elicitation of *Taxus* spp. Cell Cultures

I. Biotic Elicitors (microorganisms)

| | |
|---|---|
| *Botrytis cinerea* | *Phytophthora megasperma* |
| *Pinellas stripticum* | *Oligosporus* sp. |
| *Pythium mamillatum* | *Pythium sylvaticum* |
| *Verticillium dahliae* | *Verticillium* sp. |
| *Penicillium minioluteum* | *Phytophthora lateralis* |
| *Cytospora cincta* | *Cytospora leucostoma* |
| *Alternaria brassicicola* | *Alternaria solani* |
| *Alternaria cucumerina* | *Botrytis squamosa* |
| *Cochliobolus heterostrophus* | *Colletotrichum trifolii* |
| *Colletotrichum orbiculare* | *Colletotrichum graminicola* |
| *Colletotrichum gloeosporioides* | *Cylindrocladium floridanum* |
| *Fusarium crookwellense* | |
| *Fusarium heterosporium* | |
| *Fusarium oxysporum* f. sp. *conglutinans* | |
| *Fusarium oxysporum* f. sp. *lycopersici* | |
| *Fusarium oxysporum* f. sp. *pisi* | |
| *Gibberella zeae* | |
| *Gaeumannomyces graminis* var. *tritici* | |
| *Geotrichum* sp. | |
| *Leptosphaeria korrae* | |
| *Nectria haematococca* MPVI | |
| *Mycosphaerella pinodes* | |
| *Ophiostoma ulmi* | |
| *Phoma lingam* | |
| *Phoma pinodella* | |
| *Phytophthora infestans* | |
| *Pythium aristosporum* | |
| *Pythium graminicola* | |
| *Pythium ultimum* | |
| *Rhizoctonia solani* | |
| *Sclerotinia* sp. | |
| *S. nodorum* D-45 | |

TABLE 1.a.-continued

List of Elicitors Used in Elicitation of *Taxus* spp. Cell Cultures

*Trametes versicolor*
*Ustilago maydis*
*Venturia inaequalis*

II. Biotic Elicitors (Microbial fractions or products)

| | |
|---|---|
| Chitosan | Cellulysin |
| Lichenan | Multifect XL |
| Glucomannan | Multifect CL |
| Pleuran | Resinase |
| Glucan | Pulpxyme |
| Carboxymethylglucan | SP431 |
| Hydroxymethylglucan | Pectinol |
| Sulfoethylglucan | Rapidase |
| Mannan | Klerzyme |
| Xylan | Chitinase |
| Mannobiose | |
| Mannotriose | |
| Mannopentaose | |
| Mannotetraose | |

III. Abiotic Elicitors (Chemical Stress Agents as well as some naturally occurring biochemicals)

| | |
|---|---|
| Arachidonic acid | Elaidic acid |
| Cyclic AMP | Dibutyryl Cyclic AMP |
| Methyl jasmonate | Cis - Jasmone |
| Miconazol | Ferulic acid |
| AMO-1618 | Triton X-100 |
| Benzoic acid and derivatives | Salicylic acid and derivatives |
| Propyl gallate | Sesamol |
| Chlorocholine chloride | 3,4-dichlorophenoxy triethyl |
| Chloroethylphosphonic acid | (amine) |
| Nordihydroguaiaretic acid | Diethyldithiocarbamic acid |
| Dithiothreitol | Sodium metabisulfite |
| Potassium metabisulfite | b-amino-DL-Phenylalanine |
| Vanadyl sulfate | Uniconazol |
| Paclobutrazol | Spermine |
| Spermidine | Putrescine |
| Cadavarine | |
| Protamine Sulfate | |
| SKF-7997 | |
| MER 29 | |
| Ancymidol | |
| Triadimefon | |
| Phosphon D | |
| Thiourea | |
| Dextran Sulfate | |
| Hydroquinone | |
| Chitosan glutamate | |
| Fenpropemorph | |
| Prochloraz | |
| Naptifine | |
| EDU | |
| HTA | |
| MPTA | |
| Glutathione | |
| EGTA | |
| Gibberellins | |
| Abscisic Acid | |
| 1,3-Diphenyl urea | |
| Diazolidinyl urea | |
| Phloroglucinol | |
| Sodium alginate | |
| Carragenan | |

TABLE 1.b.

List of Precursors, Inhibitors & Stimulants or Activators Used in Regulation of Biosynthesis of Taxol & Taxanes in T. spp. cell cultures.

| Precursors | Inhibitors | Stimulants |
|---|---|---|
| Phenylalanine | Chlorocholine chloride | Cyclic AMP |
| Lysine | Uniconazol | Dibutyryl Cyclic AMP |
| Tyrosine | Paclobutrazol | Methyl jasmonate |

TABLE 1.b.-continued

List of Precursors, Inhibitors & Stimulants or Activators Used in Regulation of Biosynthesis of Taxol & Taxanes in T. spp. cell cultures.

| Precursors | Inhibitors | Stimulants |
|---|---|---|
| Tryptophan | SKF-7997 | Cis-Jasmone |
| Methionine | MER 29 | Chloroethylphosphonic acid |
| Tyramine | Ancymidol | Spermine |
| Acetic acid and its' salts | Triadimefon | Spermidine |
| | Phosphon D | Putrescine |
| | Fenpropemorph | Cadavarine |
| Mevalonic acid | Prochloraz | MPTA |
| Farnesyl acetate | Naptifine | DCPTA |
| Geranyl acetate | Miconazol | DIPTA |
| Geranylgeraniol acetate | Silver Nitrate | ACC |
| Tryptamine | Norbornadiene | HTA |
| Menthol | AMO 1618 | Brassinosteroids |
| a-Pinene | Alar | BHA |
| Trans-cinnamic acid | 4-amino-5-Hexynoic acid | BHT |
| Cambrene A | Phenylethanolamine | OTA |
| Verticillene | Phenethylamine | |
| Verticillol | Glyphosate | |
| Camphor | Dihydrocycloeucalenol | |
| Quercetin | Methionine Sulfoxide | |
| Levulinic acid | β-Hydroxyphenethylamine | |
| Abietic acid | 5-Methyl-DL-Tryptophan | |
| Borneol | a-Fluorophenylalanine | |
| | 5-2 Aminoethyl-L-cysteine hydrochloride | |

TABLE 1.c.

ELICITORS

| | |
|---|---|
| Xylanase | Butaclore |
| Chitooligosaccharides | Butylisothiocynate |
| Spermine Bis Nitric oxide Adduct | Chloramben |
| N,N'-Diacetylchitobiose isopropylamine Bis Nitric oxide Adduct | Ethyl carbamate |
| | 2-Hydroxyethylhydrazine |
| | Hydroxyglutaric acid disodium |
| Diethylamine Bis (Nitric oxide) Adduct | Tryptophol |
| | Thiourea |
| Benzyl N,N'-Diacetyl-β-chitobioside | Thioacetamide |
| | 2,4,6-Trichlorphenol |
| Syringic acid | Pyridine-2-aldoxime methochloride |
| Benzothiadiazole | Potassium oxalate monohydrate |
| Bipyridyl | Poly-L-Lysine hydrobromide |
| Gossypol and derivatives | Nerol |
| 2-chlor-4-methylisonicotinic acid | N-(1-Naphthyl) phthalamic acid |
| Indomethacin | Oxalate |
| N,N',N'-Triacetylchitotriose | Octapomine hydrochloride |
| N,N'-Diacitylchitobiose | Oxizamide |
| Diammoniun oxalate | 2-Methylpyrazine |
| Nigeran | Methoxyacetic acid |
| p-hydroxyacetophenone | N-Ethoxycarbonyl-2-ethoxy-1,2-Dihydroquinoline |
| Pectic acid | |
| Lysozyme | Lanthanum acitate |
| Nitric oxide | Linolenic acid |
| Glutathione (reduced) | Lipase |
| 1,2-Diaminopropane | Iodoacetamide |
| 1,3-Diaminopropane | 2-hydroxyethylhydrazine |
| β-mercaptoethylamine | Dinocap |
| Hydroxylamine | 1,3-Diphenylurea |
| Deoxyglucose | Hydrogen peroxide |
| 2-chlorobenzoic acid | Urea hydroperoxide |
| 2-Methyl-1,2-DL (3-Pyridyl) | Sebacic acid |
| 1-Propane | Benzoyl peroxide |
| 5-Bromouracil | N-methylmaleimide |
| 7-Nitrondazole | Cumen peroxide |
| 8-Hydroxyquinoline | N-Acetyl-D-Glucosamine |
| Acedoamidocinnamic acid | Octyl-β-D-Glucopyranoside |
| 2-Aminoanthraquinone | Diisopropyl fluorophosphate |
| N-Acetyl-L-glutamic acid | Isopropyl-β-D-thiogalactopyranoside |
| Agmatin | Hydroxyexhyl-β-1,3-glucan |

TABLE 1.c.-continued

ELICITORS

| | |
|---|---|
| 3-Acetyl pyridine | Dextran |
| Butyryl Butyryl Lactate | Lucifer yellow |
| 7-Bromo-5-chloro-8-hydroxy-quinoline | |
| Benzylbenzoate | |
| Bromoxynil | |
| Syringaldehyde | |
| Chitinase | |
| Bacitracin | |
| Calcium cyanide | |
| Glucans | |
| Glutaric acid | |
| Morpholine | |
| Octamethylcyclotetrasiloxane | |
| Trigonelline hydrochloride | |
| Anthranilic acid | |
| Colistin methane sulfonate | |
| Colchicine | |
| 2,4-Dichlorophenol | |
| L-Phenylalanine-2-naphthylamide | |
| Hydroxyglutaric acid, and its salts | |
| DL-2-Hydroxy-3-methylbutyric acid | |
| 1-10-Phenanthroline monohydrate | |
| N-sulfosuccinimidyl-3-(4-Hydroxyphenyl)propionate | |
| Trans-1,6-diphenylhexatriene | |
| Arachidonic acid | |
| Urea hydrogen peroxide | |
| Hydrogen peroxide | |
| Bestatin | |
| Butylated hydroxyanisole | |
| Butylated hydroxytoluene | |
| Gellan gum | |
| cellulase | |
| Pimelic acid | |
| Diisopropyl phosphochloridate | |
| Nitrapyrin | |
| t-Butyl hydroperoxide | |
| DL-Phosphinothricin ammonium | |
| Methyl syringate | |
| Trifluralin | |
| Tridecanone | |
| Mimosine | |
| Narigenin | |
| Dimethylaminopyridine | |
| 1-Benzylimidazole | |
| DL-o-chlorophenylalanine | |
| Cetylpyridinium chloride | |
| Hydroquinone | |
| Syringomycin | |

TABLE 1.d.

PRECURSORS

| | |
|---|---|
| Dimethylphenylalanine | D-fructose-1,6-Diphosphate |
| Geranyl chloride | β-Hydroxypyruvic acid |
| Geranylgeraniol | 4-Hydroxyphenylpyruvic acid |
| trans-Cinnamic acid | Methyl acetate |
| Pyruvic acid | Methyl laurate |
| Phenylpyruvic acid | Oxaloacetic acid |
| Orthosuccinylbenzoic acid | Pinenes |
| 2,3-dihydrobenzoic acid | Geranyl acetate |
| o-hydroxyphenylpyruvic acid | Nerol |
| Postassium acetate | Phellandrene |
| Glutamic acid | Benzoyl chloride |
| Aspartic acid | R(−)Citramalic acid |
| DL-β-phenylserine | Aspargine |
| Hippuric acid | 2,3-Dichlorobenzoic acid |
| p-Hydroxycinnamic acid | Isoleucine |
| Benzyl acetate | Leucine |
| Phenylacetic acid | Phosphoglyceric acid |
| 3-Benzoylpropionic acid | Serine |

TABLE 1.d.-continued

| PRECURSORS | |
|---|---|
| Citric acid | 2-Hydroxycinnamic acid |
| Calcium benzoate | 3-Hydroxycinnamic acid |
| Arginine | 4-Hydroxycinnamic acid |
| N-Benzoyl-DL-Phenylalanine | Borneol |
| 3,4-Dihydroxycinnamic acid | Phosphoglycerate Potassium Salt |
| Phosphoenolpyruvic acid | Glyceraldehyde-3-phosphate |
| Phenylisoserine | Dihydroxyacetone phosphate |
| 4-Hydrocoumarin | Glycine |
| Glutamine | Ethyl acetate |
| Ornithine | Methyl cinnamate |
| Methionine | Potassium acetate |
| Shikimic acid | DL-Glyceraldehyde-Phosphate free acid |
| Oxoglutamic acid | |
| DL-3-Amino-3-phenylpropionic acid | Calcium benzoate |
| a-Phenylalanine | Oxoglutamic acid |
| β-Phenylalanine | Phosphoenolpyruvic acid |
| N-Benzoylphenylisoserine | Menthol |
| Geraniol | Cambrene A |
| Linalool | Verticillol |
| Geranyl linalool | Verticellene |
| Isoborynyl isovalerate | Abietic acid |
| Cinnamyl acetate | Succinic acid |
| Cinnamyl propionate | Fumaric acid |
| Cinnamyl chloride | Acetoacetate Potassium Salt |

TABLE 1.e.

| INHIBITORS | |
|---|---|
| Rhizobitoxine | Trans-3,4-difluorocinnamic acid |
| a-Canaline | Mercaptoethanol |
| a-Aminosobutyric acid | 4-Hydroxycoumarin |
| cis-Propenylphosphonic acid | Cinnamulfluorene |
| Flurprimidol | 2-Cyano-4-Hydroxycinnamic acid |
| Chloromethyl Cyclopropane | Cinnamylidenemalonic acid |
| Diazocyclopentadiene | 4-Dimethylaminocinnamic acid |
| Diammonium succinate | N-Cinnamylpiperazine |
| g-Glutamylmethylamide | N-trans-Cinnamoylimidazole |
| 2,3-Dimercaptosuccinic acid | Cinnamylideneacetophenone |
| p-Nitrophenylphosphate | 3,4-Methylenedioxy cinnamic acid |
| Pervanadate | 3,4-Methylenedioxy-6-nitrocinnamic acid |
| Orthovanadate | |
| N-Acetyl-DL-homocysteine | 3-(3,4-Methylenedioxyphenyl) propionic acid |
| Thiolactone | |
| 2,3-diphosphoglyceric acid salts | 3,4-Methylenedioxyphenylacetic acid |
| p-Hydroxymercurylbenzoate | |
| Methylmercury chloride | 3,4-trans-Dimethoxycinnamic acid |
| Methylcyclopropane | 4-Methoxycinnamic acid |
| Methylcyclopropane carboxylate | 2-Methoxycinnamic acid |
| Cyclooctodine | 4-Nitrocinnamic acid ethyl ester |
| Methoxyvinyl glycine | Methoxycinnamic acid |
| Ibuprofen | 4-Nitrocinnamaldehyde |
| Piperonylic acid | 3-Nitrocinnamic acid |
| Phenylpropiolic acid | 2-Nitrocinnamic acid |
| L-2-Hydroxy-3-phenylpropionic acid | 3,4-Dimethoxy-6-nitrocinnamic acid |
| Amino oxyacetic acid | |
| D-Phenylalanine | Ammonium oxalate |
| Phenylpyruvic acid | Sinapic acid |
| L-Tyrosine | 2-Hydroxy-4,6-dimethoxybenzoic acid |
| 4-Fluoro-(1-amino-2-phenylethyl) | |
| Phosphonic acid | 3-dimethylaminobenzoic acid |
| 4-Hydroxyphenylpyruvic acid | 3,4-dimethoxybenzoic acid |
| m-Fluoro-DL-phenylalanine | 4-Methoxybenzoic acid |
| p-Fluoro-DL-phenylalanine | N(G)-Nitro-D-Arginine |
| m-Fluoro-DL-tyrosine | N(G)-Nitro-L-Arginine |
| 3,4-Difluoro-D-phenylalanine | Malonic acid |
| 1-Aminobenzotriazol | Maleic acid hydrozide |
| 4-Fluorocinnamic acid | Okadaic acid |
| SKF-525A | 1,4-Cyclohexanedione |
| Diethyldithiocarbamic acid, Sodium Salt | Diisopropyl fluorophosphate |
| | Oxamic acid |
| Dithiothreitol | Oxamic acid, derivatives |
| p-Coumaric acid | Sulfanilamide |
| Vinylimidazole | N-Acetyl-S-farnesyl-L-cysteine |

TABLE 1.e.-continued

| INHIBITORS | |
|---|---|
| a-Hydroxyfarnesylphosphonic acid | Chaetomellic acid A, sodium salt |
| N6-Monomethyl-L-arginine | Isonicotinic acid hydrazide |
| 7-Nitroondazole | 2,3-dimercaptopropanol |
| Norflurazon | Salicylhydroxyamic acid |
| Cyclooctodieneα-Fluorophenyl-alanine | 3-amino-4-hydroxybenzene-sulphonic acid |
| Diethyldithiocarbamic acid | Hydroxyurea |
| SKF-7997[Tris-(2-diethylamino-ethyl)-phosphate trichloride] | 6,7-dimethoxy-1,2-benzisoxazole-3-acetic acid |
| Triadimefon | 3-oxo-1,2-benzisothiazoline-2-ylacetic acid |
| 2,3,4-Trimethoxycinnamic acid | |
| 2,4-Dimethoxycinnamic acid | 2,3,5-Triiodobenzoic acid |
| 3-Hydroxyphenylacetic acid | 2-(p-Chlorophenoxy)-2-methylpropionic acid |
| 4-Aminotriazole | |
| 4-Fluorocinnamic acid | N-(1-Naphthyl)phthalamic acid |
| 4-Chloro-2-methylphenoxyacetic acid | 1-Pyrenoxylbenzoic acid |
| 1,3-Dichloropropane | 2-Chloro-9-hydroxyfluorene-9-carboxylic acid |
| N-Ethylmaleimide | |
| Semicarbizide | Chlorocholine chloride |
| 4-Chlororesorcinol | 2'-Isopropyl-4'-(trimethyl-ammonium chloride)-5-methyl phenylpeperidone carboxylate |
| 1,2-Dichloropropane | |
| Idoacetamide | |
| Phenylhydrazine | Sesamol |
| Silver thiosulfate | Ancymidol |
| Silver chloride | Daminozide |
| Thiosemicarbazide | Lovastatin |
| N-(phosponomethyl)-Glycine | Simvastatin |
| p-Chlorophenoxyisobutyric acid | Caffeic acid |
| Triton x-100 | Ferulic acid |
| Triparanol | 2,5-Dihydroxycinnamic acid |
| Chlorphonium chloride | 2,5-Dihydromethoxycinnamic acid |
| Mepiquat | 4-Hexylresorcinol |
| Prohexadione calcium salt | Cetylpyridinum chloride |
| Chloromequat | Stourosporine |
| Tetcyclasis | Dimethylthiourea |
| 2-Aza-2,3-dihydrosqualene | Phenylpropiolic acid |
| Dinoconazole | Ammonium oxalate |
| Tridemorph | 1-Aminobenzotriazole |
| 2,3-Iminosqualene | 1-Vinylimidazole |
| Glyphosine | Mercaptoethanol |
| Isoprophyl-N-phenyl carbamate | 3,5-Diido-4-hydroxybenzoic acid |
| Oryzalin | 5-Methyl-7-chloro-4-ethoxycarbanylmethoxy-2,1,3-benzothiadiazole |
| Caffeine | |
| D-Arginine | |
| α-Methylornithine | Bromoxynil |
| Conavanine | 3,4,5-Trichlorophenol |
| Abscisic acid | N-Methylmaleimide |
| 3-Amino-1,2,4-triazole | 4-Fluoro-DL-tyrosine |
| 4-Nitrocinnamic acid | Ethyl-3-nitrocinnamate |
| 3,4-Dimethoxyphenylacetic acid | Conavanin |
| N-Cinnamylpiperazine | Methylacetylenic putrescine |
| Hydroxylamine | Methylpyruvic acid |
| 2,4-Dinitrophenylhydrazine | α-Hydroxy-2-pyridinemethane sulfonic acid |
| Tetramethylammonium bromide | |
| Clotrimazole | Acetohydroxamic acid |
| Valinonycin | Isopropyl-N-phenyl carbamate |
| Procaine | D1-phenylene iodonium |
| Monensin | 2-Aminoindan-2-phosphonic acid |
| Uniconazole | Potassium-arsenate |
| Paclobutrazole | α-aminooxy-β-phenylpropionic acid |
| 4-Aminotriazole | |
| Benzyl isothiocyanate | Benzyl hydroxylamine |
| Selenomethionine | Piperonyl butoxide |
| 1-Acetyl-2-thiourea | |
| 3,4-Dehydro-DL-proline | |
| 2-Ethylnaphthalene | |
| 3-Nitrobenzoic acid | |
| Silver salts such as Silver chloride, Silver nitrate, etc. | |
| Sodium hydrosulfite | |
| 7-nitrodazole | |
| Ethionine | |
| Azacytididine | |
| Ethoxy-carbonyl-pyrimidine | |
| Miconazole | |
| 2,3:4,6-Di-o-isopropylidene-2-keto-L-Gulonic acid | |

TABLE 1.e.-continued

INHIBITORS

N-(4-Hydroxyphenyl)glycine
3-(4-Hydroxyphenyl)propionic acid
3-(2-Hydroxyphenyl)propionic acid
4-Cyclohexanedione
N-(6-aminohexyl)-5-chloro-1-
Naphthal enesulfonamide
hydrochloride
Endothal
Phosphan
Cyanamide
α-(1-Methylethyl)-α-(4-
trifluoromethoxy)p henyl-5-
pyrimidinemethanol
2-Aminoisobutyric acid
D-Arginine
n-Butylamine
p-Chloromercurybenzene sulphonic
acid
Methylglyoxal bis (guanyl
hydrazone)
α-Methyl ornithine

TABLE 1.f.

STIMULANTS

| | |
|---|---|
| Potassium pyrophosphate | p-aminohippuric acid |
| Sodium pyrophosphate | Benzylcinnamate |
| Uracil | Jasmonic acid |
| Melatonin | Methyl jasmonate |
| Hydroxylamine hydrochloride | Dihydroisojasmone |
| Thionicotinamide | Isojasmone |
| S-adenosyl-L-methionine | cis-jasmone |
| Inosine triphosphate | Tetrahydrojasmone |
| Indole-3-lactic acid | Lactone of cis-jasmone |
| Indole-3-pyruvic acid | Dihydrojasmone |
| Indole-2-carboxylic acid | Jasminolactone |
| Indole-3-aldehyde | Jasmolactone |
| N-indolyl acetyl valine | 12-oxophytodienoic acid |
| Pyridoxal phosphate | Jasmonol |
| Methyl dihydrojasmonate | g-methyldecalactone |
| Bipyridyl | Citronellyl tiglate |
| 4-acetamidophenol | Jasmonyl acetate |
| Imidazole | Mastoparan |
| Octyl-β-D-glucopyranoside | Lysophosphatidic acid |
| 3-aminopyridine | Cypermethrin |
| Guanylic acid | Cantharidin |
| Citydylic acid | Acetylsalicylic acid |
| Isopropyl-β-d-thiogalactopyranoside | Salicylic acid and derivatives |
| 3-(4-hydroxyphenyl) propionic acid | 2,6-dichloroisonicotinic acid |
| 3-(2-hyroxyphenyl) propionic acid | Nitric oxide |
| Indole-3-pyruvic acid | Traumatic acid |
| Thiobenzoic acid | Citric acid |
| Dimethylaminophenylalanine | Cytidylic acid |
| p-hydroxyphenylpyruvic acid | malic acid or malic acid salt |
| 2,3-dihydroxybenzoic acid | Potassium malate |
| Ethyl benzoate | Citric acid salts and derivatives |
| 3,4-dihydroxycinnamic acid | Flavin adenine mononucleotide |
| 4-hydroxycinnamic acid | Flavin monocleotide |
| N-acetyl-L-phenylalanine | dibutyrl Cyclic AMP |
| 3-Benzoylpropionic acid | Spermine |
| p-hydroxycinnamic acid | Spermidine |
| 5',5'-Dithiobis (2-nitrobenzoic acid) | Putrescine |
| β-hydroxypyruvic acid | Cadavarine |

TABLE 1.f.-continued

STIMULANTS

| | |
|---|---|
| 4-hydroxyphenylpyruvic acid | S-Adenosylmethionine |
| Methyl cinnamate | Pyridoxal phosphate |
| Methyl salicylate | 6-Aminonicotinamide |
| 2-napthylbenzoate | 4-Dimethylaminopyridine |
| Phenylsalicylate | N-(2-Hydroxyethyl)succinimide |
| Thiosalicylic acid | 2-oxoglutaric acid |
| Propachlor | |
| Thiamine | |
| Vinyl propionate | |
| Triethylamine hydrochloride | |
| 3,5-Diisopropylsalicylic acid | |
| Adenine sulfate | |
| p-Amino-L-Phenylalanine | |
| Benzyl salicylate | |
| 1,2-Benzisoxazole | |
| 2,4-Carbonyldibenzoic acid | |
| L-Citrulline | |
| D-Erythrose 4-Phosphate | |
| Fructose 1,6-Diphosphate | |
| Inosine triphosphate | |
| N-Methylputrescine dihydrochloride | |
| β-Phenylethylamine hydrochloride | |
| Lysine | |
| Imidazole | |
| Guanylic acid | |
| Melatonin | |
| Aminocyclopropane-carboxylic acid | |
| Isopentylpyrophosphate | |
| N-Acetyl-L-glutamine | |
| Isoglutamine | |
| Threonine | |
| Potassium Pyrophosphate | |
| Sodium pyrophosphate | |
| L-2-Aminoadipic acid | |
| N-methyl-N-Propagylbenzylamine | |
| hydrochloride | |
| Aminoguanidine hemisulfate | |
| L-(+)-2-Amino-7- | |
| Phosphonoheptanoic acid | |
| Ammonium sulfamate | |
| Spermine Bis Nitric oxide adduct | |
| Diethylamine Bis Nitric oxide adduct | |
| Galactose | |
| Valine | |
| Vitamin B-12 | |
| Ascorbic acid and derivatives | |
| Coronatine | |
| Phenobarbital | |
| Pregnenolone | |
| 24-epi-Brassinolide | |
| n-Propyl Dihydrojasmonate | |
| Propyl jasmonate | |
| Epimethyl jasmonate | |

TABLE 2

Composition of media used for cultivation of Taxus species cultures

| Medium<br>Chemical Ingredient | A<br>mg/L | B<br>mg/L | C<br>mg/L | D<br>mg/L | E<br>mg/L | F<br>mg/L | G<br>mg/L | H<br>mg/L |
|---|---|---|---|---|---|---|---|---|
| Ammonium Nitrate | | | | | | 400.0 | 500.0 | 400.0 |
| Ammonium Sulfate | 134.0 | | 33.5 | 134.0 | 67.0 | | 134.0 | |
| Boric Acid | 3.0 | 1.5 | 0.75 | 3.0 | 1.5 | 0.75 | 6.2 | 1.5 |
| Calcium Chloride (anhydrous) | 113.24 | | 28.31 | 113.24 | 56.62 | 72.5 | 113.24 | 72.5 |
| Calcium Chloride 2-H2O | | 20.0 | 50.0 | | | | | |
| Calcium Nitrate 4-H2O | | 208.4 | | | | 386.0 | | 386.0 |
| Cobalt Chloride 6-H2O | 0.025 | | 0.006 | 0.025 | 0.0125 | | 0.025 | |
| Cupric Chloride H2O | | | | | | | | |
| Cupric Sulfate 5-H2O | 0.025 | 0.01 | 0.006 | 0.025 | 0.0125 | 0.25 | 0.025 | 0.25 |
| Na2 EDTA 2-H2O | 37.3 | | 9.32 | 37.3 | 18.65 | 37.3 | 37.3 | 37.3 |
| Ferric Sulfate | | 2.5 | | | | | | |
| Ferrous Sulfate 7-H2O | 27.85 | | 6.95 | 27.85 | 13.9 | 27.85 | 27.85 | 27.85 |
| Magnesium Sulfate (anhydrous) | 122.09 | 366.2 | 30.6 | 122.09 | 61.04 | 180.7 | 122.09 | 180.7 |
| Manganese Sulfate H2O | 10.0 | 23.788 | 22.5 | 10.0 | 5.0 | 22.3 | 10.0 | 22.3 |
| Molybdenum Trioxide | | 0.001 | | | | | | |
| Molybdic Acid (sodium salt) 2-H2O | 0.25 | | 0.062 | 0.25 | 0.125 | 0.25 | 0.25 | 0.25 |
| Potassium Chloride | | 65.0 | | | | | | |
| Potassium Iodide | 0.75 | 0.75 | 0.175 | 0.75 | 0.375 | | 0.75 | |
| Potassium Nitrate | 2500.0 | 80.0 | 625.0 | 2500.0 | 1250.0 | | 2500.0 | |
| Potassium Phosphate (monobasic) | | | 10.0 | | | 170.0 | | 170.0 |
| Potassium Sulfate | | | | | | 990.0 | | 990.0 |
| Sodium Phosphate (monobasic anhydrous) | 130.8 | 16.5 | 32.62 | 130.5 | 65.25 | | 130.5 | |
| Sodium Sulfate | | 200.0 | | | | | | |
| Zinc Sulfate 7-H2O | 2.0 | 3.0 | 0.5 | 2.0 | 1.0 | 8.6 | 2.0 | 8.6 |
| Myo-inositol | 100.0 | 100.0 | 125.0 | 100.0 | 50.0 | 100.0 | 100.0 | 100.0 |
| Nicotinic Acid | 1.0 | | 0.75 | 1.0 | 0.5 | 1.0 | 1.0 | 1.0 |
| Pyridoxine HCL | 1.0 | | 0.25 | 1.0 | 0.5 | 1.0 | 1.0 | 1.0 |
| Thiamine HCL | 10.0 | *5.0 | 3.5 | 10.0 | 5.0 | 10.0 | 10.0 | 10.0 |
| *Glutamine | 292.8 | 146.4 | | 292.8 | 292.8 | 1756.8 | | 292.8 |
| *Tryptophan | | | | | | | | |
| *Phenylalanine | | 30.0 | | | | | | |
| *Lysine | | 20.0 | | | | | | |
| *Methionine | | | | | | | | |
| *Sodium Acetate | | 10.0 | 10.0 | | | | | |
| Sucrose | 10000.0 | 50000.0 | 40000.0 | 10000.0 | 10000.0 | 10000.0 | 20000.0 | 10000.0 |
| N6 Benzyladenine | 0.02 | 2.0 | 2.0 | 0.002 | 0.002 | | | |
| n-Naphthaleneacetic Acid | 0.931 | 10.0 | | | | | 1.862 | |
| *Ascorbic Acid | 50.0 | 100.0 | 50.0 | 100.0 | 100.0 | 100.0 | 100.0 | 100.0 |
| Picloram | | | | 1.2 | 2.4 | 1.2 | | 1.2 |
| Casein Hydrolysate | | | 500.0 | | | | 1000.0 | |
| 6(g,g-Dimethylallylamino) Purine | | | | | | 0.02 | | |
| Kinetin | | | | | | | | 0.02 |
| Thidiazuron | | | | | | | | |
| Maltose | | | | | | | | |
| *Glutamic Acid | | | | | | | | |
| *Aspartic Acid | | | | | | | | |
| *Glycine | | | | | | | | |
| *Serine | | | | | | | | |
| *Folic Acid | | | | | | | | |
| medium pH | 5.6 | 5.8 | 5.8 | 5.6 | 5.6 | 5.6 | 5.6 | |

| Medium<br>Chemical Ingredient | I<br>mg/L | J<br>mg/L | K<br>mg/L | L<br>mg/L | M<br>mg/L | N<br>mg/L | O<br>mg/L | P<br>mg/L |
|---|---|---|---|---|---|---|---|---|
| Ammonium Nitrate | | | | | | | | |
| Ammonium Sulfate | 134.0 | 134.0 | 134.0 | 134.0 | 134.0 | 33.50 | 134.0 | 134.0 |
| Boric Acid | 3.0 | 3.0 | 3.0 | 3.0 | 3.0 | 0.75 | 3.0 | 3.0 |
| Calcium Chloride (anhydrous) | 113.24 | 113.24 | 113.24 | 113.24 | 113.24 | 28.31 | 113.24 | 113.24 |
| Calcium Chloride 2-H2O | | | | | | 50.0 | | |
| Calcium Nitrate 4-H2O | | | | | | | | |
| Cobalt Chloride 6-H2O | 0.025 | 0.025 | 0.025 | 0.025 | 0.025 | 0.01 | 0.025 | 0.025 |
| Cupric Chloride H2O | | | | | | 0.01 | | |
| Cupric Sulfate 5-H2O | 0.025 | 0.025 | 0.025 | 0.025 | 0.025 | 0.01 | 0.025 | 0.025 |
| Na2 EDTA 2-H2O | 37.3 | 37.3 | 37.3 | 37.3 | 37.3 | 9.33 | 37.3 | 37.3 |
| Ferric Sulfate | | | | | | | | |
| Ferrous Sulfate 7-H2O | 27.85 | 27.85 | 27.85 | 27.85 | 27.85 | 6.96 | 27.85 | 27.85 |
| Magnesium Sulfate (anhydrous) | 122.09 | 122.09 | 122.09 | 122.09 | 122.09 | 30.52 | 122.09 | 122.09 |
| Manganese Sulfate H2O | 10.0 | 10.0 | 10.0 | 10.0 | 10.0 | 27.50 | 10.0 | 10.0 |
| Molybdenum Trioxide | | | | | | | | |
| Molybdic Acid (sodium salt) 2-H2O | 0.25 | 0.25 | 0.25 | 0.25 | 0.25 | 0.06 | 0.25 | 0.25 |
| Potassium Chloride | | | | | | | | |
| Potassium Iodide | 0.75 | 0.75 | 0.75 | 0.75 | 0.75 | 0.19 | 0.75 | 0.75 |

TABLE 2-continued

Composition of media used for cultivation of Taxus species cultures

| | | | | | | | | |
|---|---|---|---|---|---|---|---|---|
| Potassium Nitrate | 2500.0 | 2500.0 | 2500.0 | 2500.0 | 2500.0 | 625.00 | 2500.0 | 2500.0 |
| Potassium Phosphate (monobasic) | | | | | | | | |
| Potassium Sulfate | | | | | | | | |
| Sodium Phosphate (monobasic anhydrous) | 130.5 | 130.5 | 130.5 | 130.5 | 130.5 | 32.63 | 130.5 | 130.5 |
| Sodium Sulfate | | | | | | | | |
| Zinc Sulfate 7-H2O | 2.0 | 2.0 | 2.0 | 2.0 | 2.0 | 0.50 | 2.0 | 2.0 |
| Myo-inositol | 100.0 | 100.0 | 100.0 | 100.0 | 100.0 | 25.00 | 100.0 | 100.0 |
| Nicotinic Acid | 1.0 | 1.0 | 1.0 | 1.0 | 1.0 | 0.25 | 1.0 | 1.0 |
| Pyridoxine HCL | 1.0 | 1.0 | 1.0 | 1.0 | 1.0 | 1.25 | 1.0 | 1.0 |
| Thiamine HCL | 10.0 | 10.0 | 10.0 | 10.0 | 10.0 | 2.50 | 10.0 | 10.0 |
| *Glutamine | | 292.8 | | 292.8 | | 292.8 | | 292.8 | 292.8 |
| *Tryptophan | | | | | | | | |
| *Phenylalanine | | | | | | | | |
| *Lysine | | | | | | | | |
| *Methionine | | | | | | | | |
| *Sodium Acetate | | | | | | | | |
| Sucrose | | 10000.0 | 10000.0 | 10000.0 | 10000.0 | | 30000.0 | 10000.0 | 10000.0 |
| N6 Benzyladenine | | 0.002 | 0.002 | 0.02 | 0.02 | | | 0.002 | 0.02 |
| n-Naphthaleneacetic Acid | | 0.931 | 0.931 | 1.862 | 1.862 | | | 0.931 | 1.862 |
| *Ascorbic Acid | | 100.0 | 100.0 | 100.0 | 100.0 | 100.0 | | 100.0 | 100.0 |
| Picloram | | | | | | 2.4 | | | |
| Casein Hydrolysate | | | | | | | | |
| 6(g,g-Dimethylallylamino) Purine | | | | | | | | |
| Kinetin | | | | | | | | |
| Thidiazuron | | | | | | 0.022 | | |
| Maltose | | | | | | 10000.0 | | |
| *Glutamic Acid | 1850.0 | 1850.0 | 1850.0 | 1850.0 | | | | |
| *Aspartic Acid | | | | | | 1710.0 | | |
| *Glycine | | | | | | | 5.0 | |
| *Serine | | | | | | | 5.0 | |
| *Folic Acid | | | | | | | 1.0 | |
| medium pH | 5.6 | 5.6 | 5.6 | 5.6 | 5.6 | 5.6 | 5.6 | 5.6 |

*Indicates that the component should be filter-sterilized into the medium

TABLE 3

Preferred conditions for callus proliferation for various Taxus species. The ingredients in the basal media are listed in Table 2.

| | | Growth Regulators* | | | |
|---|---|---|---|---|---|
| | | Auxin | | Cytokinin | |
| Species | Basal Medium (Table 2) | Type | Conc (M) | Type | Conc (M) |
| T. brevifolia | F | P | $5 \times 10^{-6}$ | 2iP | $10^{-7}$ |
| | D | P | $5 \times 10^{-6}$ | BA | $10^{-8}$ |
| T. canadensis | H | P | $5 \times 10^{-6}$ | K | $10^{-7}$ |
| | D | P | $5 \times 10^{-6}$ | BA | $10^{-8}$ |
| T. chinensis | D | P | $5 \times 10^{-6}$ | BA | $10^{-8}$ |
| | A | N | $5 \times 10^{-6}$ | BA | $10^{-8}$ |
| T. globosa | D | P | $5 \times 10^{-6}$ | BA | $10^{-8}$ |
| T. floridana | D | P | $5 \times 10^{-6}$ | BA | $10^{-8}$ |
| T. baccata | D | P | $5 \times 10^{-6}$ | BA | $10^{-8}$ |
| T. cuspidata | D | P | $5 \times 10^{-6}$ | BA | $10^{-8}$ |
| T. media | D | P | $5 \times 10^{-6}$ | BA | $10^{-8}$ |
| T. wallichiana | D | P | $5 \times 10^{-6}$ | BA | $10^{-8}$ |

*Abbreviations: Picloram (P), Naphthalene acetic acid (N), Benzyladenine (BA), Dimethyl allylamino purine (2iP), Kinetin (K)

TABLE 4

Typical growth characteristics of Taxus sp. suspension cultures

| Species | Dry Weight Doubling Time | Fresh Weight Doubling Time | Dry Wt. Density | Fresh Wt. Density |
|---|---|---|---|---|
| T. brevifolia | 2.0 days | 3.5 days | 20 g/L | 400 g/L |
| T. baccata | 2.0 | 6.0 | 15 | 220 |
| T. chinensis | 2.5 | 4.5 | 20 | 285 |
| T. canadensis | nd* | 8.5 | 13 | 260 |

*not yet determined

TABLE 5

Taxol production in various Taxus species.

| Species | Taxol content (% dry weight) | Medium (See Tables 2 & 3) | Analysis |
|---|---|---|---|
| T. brevifolia | 0.006 | F | ELISA |
| T. canadensis | 0.004 | H | ELISA |
| T. baccata | 0.0014 | D | HPLC |
| T. globosa | 0.0003 | G | ELISA |
| T. cuspidata | 0.0025 | G | HPLC |
| T. floridana | 0.001 | G | ELISA |
| T. media | 0.02 | F | ELISA |
| T. chinensis | 0.18 | B | HPLC |

TABLE 6

Improvements in productivity due to medium exchange treatment. Numbers are expressed as X-fold improvement over levels achieved in a 15-day batch interval. *Taxus chinensis* cell line K-1 was cultivated in Medium A in the dark.

|  | Total levels* | Extracellular levels |
|---|---|---|
| Taxol | 4.6 | 4.89 |
| Total taxanes | 4.55 | 5.94 |

*Total levels in cells and medium combined

TABLE 7

Effect of Standard GroLux light treatment on taxol and taxane content in 10-day old cultures of *Taxus chinensis* line K-1 cultivated in Medium A. Amounts shown are expression as μg extracted from 20 ml of suspension. Cell growth was identical in both treatments (164 mg dry weight per flask).

|  | Light | Dark |
|---|---|---|
| Total taxol: cells and medium: | 8.8 μg | 3.13 μg |
| Extracellular taxol: | 76.40% | 56.20% |
| Total taxanes cells and medium: | 61.55 μg | 62.17 μg |
| Extracellular taxanes: | 89% | 84% |

TABLE 8

Comparison of chitosan-glutamate treated to non-elicited suspensions of *Taxus chinensis* line K-1 after 15 days cultivation in medium C. Taxane levels reported are from cells and medium combined. % extra refers to the percentage of extracellular

|  | CONTROL | | | ELICITOR | | |
|---|---|---|---|---|---|---|
|  | Cell density 10.1 g/L | | | Cell density 14.2 gm/l | | |
|  | Cell viability 70-80% viable | | | Cell viability 75-80% viable | | |
| Taxanes | % dry wt | mg/L | % Extra | % dry wt | mg/L | % Extra |
| Taxol | 0.054 | 5.4 | 7.2 | 0.098 | 13.9 | 85.0 |
| Baccatin III | 0.057 | 5.8 | 69.9 | 0.055 | 7.8 | 76.6 |
| 7-Xylosyl-10-deacetyltaxol | 0.040 | 4.0 | 63.0 | 0.048 | 6.9 | 77.0 |
| 10-deacetyltaxol | 0.0004 | 0.4 | 71.1 | 0.0 | 1.0 | 75.3 |
| Cephalomannine |  |  |  |  |  |  |
| 10-deacetylbaccatin III |  |  |  |  |  |  |
| 10-deacetyl-7-epitaxol | 0.054 | 5.4 | 74.2 | 0.076 | 10.8 | 85.7 |
| 7-Epitaxol | 0.009 | 0.9 | 74.6 | 0.009 | 1.3 | 86.2 |
| Unknown Taxanes | 0.203 | 20.5 | 79.7 | 0.240 | 34.1 | 90.2 |
| Total Taxanes: | 0.421 | 42.4 |  | 0.533 | 75.8 |  |

TABLE 9

Nutrient medium manipulation for enhanced taxane and taxol biosynthesis in *Taxus chinensis* suspension line K-1. 500 mg fresh weight cells were inoculated per 5 mL of medium and incubated in the dark for 18 days. The total taxanes produced (in the cells and medium combined) is reported. The ingredients in media B & C are listed in Table 2.

| Taxane Level | Medium B (mg/L) | Medium C (mg/L) |
|---|---|---|
| Baccatin III | 4.3 | 3.9 |
| 7-xylosyl 10-deacetyl taxol | 8.3 | 12.9 |
| Cephalomannine | 1.1 | trace |
| 10-deacetyl 7-epi taxol | 4.6 | 5.4 |
| taxol | 24.1 | 21.3 |
| 7-epi taxol | 1.3 | 2.8 |
| other unidentified taxanes* | 56.1 | 63.7 |
| Total taxanes | 99.8 mg/l | 110 mg/l |

TABLE 10

Enhancement of Taxane Biosynthesis in *Taxus chinensis* cell line KS1A by Silver

|  |  | mg/L extracellular product** | | |
|---|---|---|---|---|
| Silver Compound | Dose (μM) | Baccatin III | Taxol | Total Taxanes |
| Culture Medium only* |  | 16 | 5 | 21 |
| Silver thiosulfate | 50 | 71 | 15 | 86 |
| Silver phosphate | 100 | 48 | 7 | 55 |
| Silver benzoate | 20 | 40 | 7 | 47 |
| Silver sulfate | 20 | 61 | 7 | 68 |
| Toluenesulfonic acid silver salt | 20 | 39 | 6 | 45 |
| Silver chloride | 10 | 22 | 18 | 40 |
| Silver oxide | 50 | 43 | 18 | 61 |
| Silver acetate | 10 | 52 | 10 | 62 |
| Silver nitrate | 20 | 63 | 6 | 69 |

*The culture medium was Medium N from Table 2, with the addition of the following growth regulators: 10 μM α-naphthaleneacetic acid, and 1 μM thidiazuron
**All samples were taken after 14 days of incubation.

TABLE 11

Enhancement of Taxol and Taxane Biosynthesis by Silver in several *Taxus chinensis* cell lines. The titers represent levels measured in the whole broth, i.e., in the cells and in the extracellular medium.

| Cell Culture | Silver[a] Concentration | Culture Medium | Duration (days) | Baccatin III mg/L | Taxol mg/L | Other Taxanes mg/L | Total Taxanes (mg/L) |
|---|---|---|---|---|---|---|---|
| SS6A-1224 | 0 | I[b] | 30 | 10 | 48 | 23 | 81 |
| SS6A-1224 | 50 μM | I | 30 | 172 | 86 | 126 | 384 |
| SS122-13 | 0 | II[c] | 14 | 2 | 21 | 10 | 33 |
| SS122-13 | 50 μM | II | 14 | 12 | 103 | 60 | 173 |
| SS122-42 | 0 | II | 14 | 3 | 80 | 26 | 109 |
| SS122-42 | 50 μM | II | 14 | 4 | 146 | 38 | 188 |

[a]Added as silver thiosulfate
[b]The culture medium is Medium N from Table 2, with the addition of the growth regulator, α-naphthaleneacetic acid at a concentration of 10 μM.
[c]The culture medium is Medium N from Table 2, with the addition of the growth regulator, α-naphthaleneacetic acid at a concentration of 10 μM and thidiazuron at a concentration of 1 μM.

TABLE 12

Enhancement of Taxol and Taxane Biosynthesis by Jasmonic acid and its methyl ester. Taxane titers were measured in the whole broth after 14 days of cultivation. The culture medium was Medium N from Table 2, with the additional presence of the growth regulator, α-naphthaleneacetic acid at a concentration of 10 μM.

| Cell Culture | Jasmonate Concentration | Baccatin III mg/L | Taxol mg/L | Other Taxanes mg/L | Total Taxanes (mg/L) |
|---|---|---|---|---|---|
| SS122-42 | 0 | 3 | 80 | 26 | 109 |
| SS122-42 | 200 μM JMA | 4 | 120 | 87 | 211 |
| SS122-42 | 89 μM MJS | 3 | 121 | 109 | 233 |
| SS122-13 | 0 | 2 | 21 | 10 | 33 |
| SS122-13 | 89 μM MJS | 9 | 73 | 63 | 124 |

[a]JMA denotes the free acid, and MJS denotes methyl jasmonate

TABLE 13

Enhancement of Taxol and Taxane Biosynthesis by 3,4-methylenedioxynitrocinnamic acid (MDNA). Taxane levels were measured in the whole broth after 14 days of cultivation. The cell line used was *Taxus chinensis* SS122-42.

| MDNA Concentration | Culture Medium[a] | Baccatin III mg/L | Taxol mg/L | Other Taxanes mg/L | Total Taxanes (mg/L) |
|---|---|---|---|---|---|
| 0 | I | 3 | 80 | 26 | 109 |
| 50 μM | I | 5 | 163 | 45 | 213 |
| 50 μM | II | 34 | 311 | 89 | 434 |

[a]The culture medium I refers to Medium N from Table 2, with the additional presence of the growth regulator, α-naphthaleneacetic acid at a concentration of 10 μM. The culture medium II is identical to Culture medium I, with the additional presence of 50 μM silver thiosulfate.

TABLE 14

Enhancement of Taxol and taxanes in cell cultures of *Taxus chinensis* using various combinations of enhancement agents. All taxane concentrations are expressed as whole broth titers (i.e., concentration in cells and medium combined), and values were obtained after 11 days of incubation.

| Cell Culture | Culture Medium[a] | Baccatin mg/L | Taxol mg/L | Other Taxanes mg/L | Total Taxanes (mg/L) |
|---|---|---|---|---|---|
| SS64-412 | I | 41 | 464 | 101 | 606 |
| SS64-561 | II | 590 | 182 | 388 | 1160 |
| SS64-571 | III | 596 | 158 | 261 | 1015 |
| SS124-77 | IV | 72 | 39 | 576 | 687 |
| SS122-29 | V | 18 | 306 | 152 | 476 |
| SS85-26 | VI | 586 | 100 | 416 | 1102 |

[a]The culture medium for all combinations was Medium N in Table 2. Culture Medium I contained, in addition to Medium N, 10 μM α-naphthaleneacetic acid (NAA), 3 μM thidiazuron (TDZ), 50 μM 3,4-methylenedioxynitrocinnamic acid (MDNA), 89 μM methyl jasmonate (MJS), and 50 μM silver thiosulfate (SLTS). Culture Medium II contained, in addition Medium N, 10 μM NAA, 1 μM TDZ, 50 μM MDNA, 89 μM MJS, 10 μM SLTS, and an additional 98.5 mg/L sodium phosphate (monobasic). Culture medium III contained, in addition to Medium N, 10 μM indolebutyric acid, 3 μM TDZ, 30 μM 3,4-methylenedioxycinnamic acid, 89 μM MJS, and 50 μM SLTS. Culture medium IV contained, in addition to Medium N, 10 μM NAA, 89 μM MJS, 100 μM SLTS, and 5 mM glutamine. Culture medium V contained, in addition to Medium N, 10 μM NAA, 89 μM MJS, and 50 μM SLTS. Culture medium VI contained, in addition to Medium N, 10 μM NAA, 1 μM TDZ, 50 μM MDNA, 18 μM MJS, 50 μM SLTS, and 5 mM glutamine.

TABLE 15

Enhancement of Taxane Production by Medium Exchange.

| Cell Line | Culture Medium[a] | Type of Operation[b] | Duration (days) | Product[c] | Production Level[d] (mg/L) | Ave. Volumetric Productivity[e] (mg/L/day) |
|---|---|---|---|---|---|---|
| Paella | I | Batch | 11 | Taxol | 185 | 13 |
| Paella | I | Medium exchange | 20 | Taxol | 265 | 17 |

TABLE 15-continued

Enhancement of Taxane Production by Medium Exchange.

| Cell Line | Culture Medium[a] | Type of Operation[b] | Duration (days) | Product[c] | Production Level[d] (mg/L) | Ave. Volumetric Productivity[e] (mg/L/day) |
|---|---|---|---|---|---|---|
| SS29-3A5 | II | Batch | 14 | Baccatin III | 260 | 18 |
| SS29-3A5 | II | Medium exchange | 28 | Baccatin III | 580 | 21 |
| SS29-3A5 | II | Batch | 22 | 10-deacetyl-baccatin III | 300 | 14 |
| SS29-3A5 | II | Medium exchange | 28 | 10-deacetyl-baccatin III | 400 | 14 |
| SS45-146 | III | Batch | 11 | Total Taxanes | 700 | 64 |
| SS45-146 | III | Medium exchange | 28 | Total Taxanes | 2500 | 89 |

[a]The culture medium for these culture conditions was Medium N in Table 2. Culture medium I included, in addition to Medium N, 10 μM α-naphthaleneacetic acid (NAA), 1 μM thidiazuron (TDZ), 50 μM 3,4-methylenedioxynitro-cinnamic acid (MDNA), 18 μM methyl jasmonate (MJS), and 10 μM silver thiosulfate (SLTS). Culture medium II included, in addition to Medium N, 10 μM NAA, 1 μM TDZ, 50 μM MDNA, 89 μM MJS, 10 μM SLTS, and 5 mM glutamic acid (monopotassium salt). Culture medium III included, in addition to Medium N, 10 μM NAA, 2.5 μM zeatin, 30 μM MDNA, 89 μM MJS, and 50 μM SLTS.
[b]Repeated enhancement was achieved by medium exchange, as described in Example 14.
[c]The predominant product produced by a given cell line under the specified culture medium is listed; taxanes other than the predominant product were also produced in each case, except for cell line SS45-146, for which total taxane production is listed.
[d]The production levels for batch cultivation refer to extracellular concentrations, i.e., the amount of taxane measured in the extracellular medium divided by the volume of the extracellular medium. For repeated enhancement by medium exchange, the production level refers to the total amount of taxane measured in the extracellular medium after each medium exchange, divided by the suspension volume.
[e]The average volumetric productivity is one indicator of biosynthetic capability; it is defined as the total product divided by the suspension volume, and further divided by the duration of the incubation.

TABLE 16.a

Enhancement of Taxol and Taxane Production by Fed Batch Operation

| Cell line | Culture medium[a] | Type of operation | Fed batch components[b] | Total culture duration (days) | Baccatin III (mg/L)* | Taxol (mg/L) | Other taxanes (mg/L) | Total taxanes (mg/L) |
|---|---|---|---|---|---|---|---|---|
| CR-128 | A | Batch | — | 24 | 152 | 134 | 203 | 489 |
|  | A | Fed batch | F1 | 24 | 257 | 200 | 295 | 752 |
|  | A | Fed batch | F2 | 24 | 254 | 316 | 427 | 997 |
| SS36-245 | B | Batch | — | 31 | 170 | 80 | 190 | 440 |
|  | B | Fed batch | F3 | 31 | 50 | 212 | 198 | 460 |
|  | B | Fed batch | F4 | 31 | 56 | 412 | 348 | 816 |
| SS36-359 | C | Batch | — | 21 | 220 | 155 | 163 | 538 |
|  | C | Fed batch | F5 | 21 | 439 | 182 | 304 | 925 |

[a]The culture medium for all cell lines was Medium N (Table 2).
In addition, Culture medium I contained 10 μM α-naphthaleneacetic acid (NAA), 30 μM 3,4-methylenedioxy-6-nitrocinnamic acid (MDNA), 18 μM methyl jasmonate (MJS), and 50 μM silver thiosulfate (SLTS).
Culture medium II contained, in addition to Medium N, 10 μM NAA, 50 μM MDNA, 50 μM SLTS, and 1 μM thidiazuron (TDZ).
Culture medium III contained, in addition to Medium N, 10 μM NAA, 1 μM TDZ, 50 μM MDNA, 50 μM SLTS, 89 μM MJS.
*All taxane values refer to whole broth titers: (mg taxanes in cells + mg taxanes in extracellular medium)/Total culture volume (liters).

TABLE 16.b

Details of fed-batch operation described in Table 16.a.

| Feed solution | Composition | Feed rate (mL/L/day) | Start of feed (day) | Duration of feed (days) |
|---|---|---|---|---|
| F1 | 25% (weight/volume) (w/v) fructose, 25 mM glutamine, 50 μM NAA, 250 μM SLTS, 89 μM MJS, 1.48 mM calcium chloride, 0.63 mM magnesium sulfate; 0.68 mM sodium phosphate (monobasic). | 10 | 7 | 17 |
| F2 | F1, 75 mM α-phenylalanine, 25 mM β-phenylalanine | 10 | 7 | 17 |

TABLE 16.b-continued

Details of fed-batch operation described in Table 16.a.

| Feed solution | Composition | Feed rate (mL/L/day) | Start of feed (day) | Duration of feed (days) |
|---|---|---|---|---|
| F3 | 25% (w/v) fructose, 150 mM α-phenylalanine, 25 mM β-phenylalanine | 10 | 6 | 25 |
| F4 | 50% (w/v) glucose, 5.92 mM calcium chloride, 2.52 mM magnesium sulfate, 2.72 mM sodium phosphate (monobasic), 500 μM SLTS, 10 μM TDZ, 100 μM NAA, 150 mM α-phenylalanine, 50 mM β-phenylalanine | 5 | 9 | 22 |
| F5 | contained 50% (w/v) glucose, 100 μM NAA, 10 μM TDZ, 500 μM SLTS, 89 μM MJS, 0.68 mM sodium phosphate (monobasic), 50 mM α-phenylalanine | 5 | 12 | 9 |

TABLE 17

Enhancement of Taxol and taxanes in cell cultures of *Taxus chinesis* using various combinations of enhancement agents. All taxane concentrations are expressed as whole broth titers (i.e., concentration in cells and medium combined).

| Cell Culture | Culture Medium[a] | Duration (days) | Baccatin mg/L | Taxol mg/L | Other Taxanes mg/L | Total Taxanes (mg/L) |
|---|---|---|---|---|---|---|
| SS122-41 | I | 20 | 106 | 374 | 158 | 638 |
| SS122-41 | I[b] | 20 | 7 | 507 | 148 | 662 |
| SS122-30 | II | 14 | 27 | 279 | 226 | 532 |
| cr427 | III | 14 | 13 | 302 | 125 | 440 |
| cr452 | IV | 14 | 11 | 190 | 95 | 296 |
| cr452 | V | 14 | 4 | 172 | 67 | 243 |
| cr857 | I | 24 | 116 | 531 | 258 | 905 |
| cr914 | VI | 14 | 260 | 436 | 312 | 1008 |

[a] The culture medium for all combinations was Medium N (Table 2) in which the primary carbon source was replaced by other sources as described in this legend. Culture Medium I contained 100 g/L maltose instead of sucrose, and in addition, contained, 20 μM α-naphthaleneacetic acid (NAA), 40 μM 3,4-methylenedioxynitrocinnamic acid (MDNA), 45 μM methyl jasmonate (MJS), 100 μM silver thiosulfate (SLTS), and 5 mM glutamine. Culture Medium II contained 50 g/L maltose instead of sucrose, and in addition, contained, 10 μM NAA, 40 μM MDNA, 100 μM MJS and 75 μM SLTS. Culture Medium III contained 50 g/L maltose instead of sucrose, and in addition, contained, 20 μM NAA, 40 μM MDNA, 45 μM MJS, 100 μM SLTS, and 5 mM glutamine. Culture Medium IV contained 50 g/L lactose instead of sucrose, and in addition, contained 20 μM NAA, 40 μM MDNA, 45 μM MJS, 100 μM SLTS, and 5mM glutamine. Culture Medium V contained 40 g/L galactose instead of sucrose, and in addition, contained 20 μM NAA, 40 μM MDNA, 45 μM MJS, 100 μM SLTS, and 5 mM glutamine. Culture Medium VI contained 70 g/L maltose instead of sucrose and in addition, contained, 20 μM NAA, 40 μM MDNA, 45 μM MJS, 100 μM SLTS, and 5 mM glutamine.
[b] The fresh weight density was 26% (w/v)

The culture medium for all combinations was Medium N (Table 2) in which the primary carbon was replaced by other sources as described in this legend. Culture Medium I contained 100 g/L maltose instead of sucrose, and in addition, contained, 20 μM α-naphthaleneacetic acid (NAA), 40 μM 3,4-methylenedioxynitocinnamic acid (MDNA), 45 μM methyljasmonate (MJS), 100 μM silver thiosulfate (SLTS), and 5 mM glutamine. Culture Medium II contained 50 g/L maltose instead of sucrose, and in addition, contained, 10 μM NAA, 40 μM MDNA, 100 μM MJS and 75 μM SLTS. Culture Medium III contained 50 g/L maltose instead of sucrose, and in addition, contained, 20 μM NAA, 40 μM MDNA, 45 μM MJS, 100 μM SLTS, and 5 mM glutamine. Culture Medium IV contained 50 g/L lactose instead of sucrose, and in addition, contained 20 μM NAA, 40 μM MDNA, 45 μM MJS, 100 μM SLTS, and 5 mM glutamine. Culture Medium V contained 40 g/L galactose instead of sucrose, and in addition, contained 20 μM NAA, 40 μM MDNA, 45 μM MJS, 100 μM SLTS, and 5 mM glutamine. Culture Medium VI contained 70 g/L maltose instead of sucrose and in addition, contained, 20 μM NAA, 40 μM MDNA, 45 μM MJS, 100 μM SLTS, and 5 mM glutamine.

TABLE 18.a.

Enhancement of Taxol and Taxane Production by Fed Batch Operation

| Cell culture | Culture medium[c] | Type of operation | Fed batch components[d] | Baccatin III (mg/L)[e] | Taxol (mg/L) | Other taxanes (mg/L) | Total taxanes (mg/L) |
|---|---|---|---|---|---|---|---|
| SS122-41[a] | A | Batch | — | 120 | 225 | 123 | 468 |
|  | A | Fed batch | F1 | 32 | 476 | 171 | 679 |
|  | A | Fed batch | F2 | 27 | 501 | 180 | 708 |

TABLE 18.a.-continued

Enhancement of Taxol and Taxane Production by Fed Batch Operation

| Cell culture | Culture medium[c] | Type of operation | Fed batch components[d] | Baccatin III (mg/L)[e] | Taxol (mg/L) | Other taxanes (mg/L) | Total taxanes (mg/L) |
|---|---|---|---|---|---|---|---|
| SS122-41[b] | B | Batch | — | 7 | 507 | 148 | 662 |
|  | B | Fed batch | F3 | 66 | 902 | 251 | 1219 |

[a]Inoculation density was 20% (w/v)
[b]Inoculation density was 26% (w/v)
[c]The culture medium for all cell lines was Medium N (Table 2). The primary carbon source was sucrose unless substituted as described here. In addition, culture medium A contained 20 μM α-naphthaleneacetic acid (NAA), 40 μM 3,4-methylenedioxynitrocinnamic acid (MDNA), 45 μM methyl jasmonate (MJS), and 100 μM silver thiosulfate (SLTS), and 5 mM glutamine. Culture medium B contained 100 mg/l maltose instead of sucrose, and in additioncontained, 20 μM NAA, 40 μM MDNA, 45 μM MJS, 100 μM SLTS, and 5 mM glutamine.
[d]Refer to Table 18b
[e]All taxane values refer to whole broth titers: (mg taxanes in cells + mg taxanes in extracellular medium)/Total culture volume (liters)

TABLE 18.b.

Details of fed-batch operation described in Table 18.a.

| Feed solution | Composition | Feed rate (mL/L/day) | Start of feed (day) | Duration of fed batch (days) |
|---|---|---|---|---|
| F1 | 50% (weight/volume) (w/v) fructose, 50 mM glutamine | 8 | 10 | 11-21 |
| F2 | 50% (w/v) maltose, 50 mM glutamine | 8 | 10 | 11-21 |
| F3 | 50% (w/v) maltose, 200 μM NAA, 450 μM MJS, 50 mM glutamine | 8 | 10 | 10-20 |

The invention claimed is:

1. A method for producing one or more taxanes in high yields in cell culture of a *Taxus* species comprising: cultivating in suspension culture, in one or more nutrient media under growth and product formation conditions, cells of a *Taxus* species derived from callus or suspension cultures, and recovering one or more taxanes from said cells, said medium of said cell culture, or both, wherein at least one of the one or more nutrient media comprises one or more enhancement agents selected from the group consisting of (a) jasmonate-related compounds or alkyl esters thereof, (b) antiethylene agents, and (c) inhibitors of phenylpropanoid metabolism.

2. The method of claim 1, wherein the one or more nutrient media contain an antiethylene agent which is a silver-containing compound, or a silver complex, or a silver ion.

3. The method of claim 2, wherein the concentration of silver ions, silver complexes, or silver-containing compounds is 0.01 μM-10 μM.

4. The method of claim 1, wherein the jasmonate-related compound or an alkyl ester thereof is added to the one or more nutrient media.

5. The method of claim 4, wherein the jasmonate-related compound is in a concentration from $10^{-5}$ to $2 \times 10^4$ M.

6. The method of claim 4, wherein the jasmonate-related compound is at least one compound selected from the group consisting of jasmonic acid and dihydrojasmonic acid.

7. The method of claim 4, wherein the jasmonate-related compound is at least one compound selected from the group consisting of jasmonic acid and alkyl esters of jasmonic acid.

8. The method of claim 7, wherein said alkyl ester of jasmonic acid comprises an alkyl group esterified to jasmonic acid wherein said alkyl group has from one to four carbon atoms.

9. The method of claim 8, wherein the alkyl group esterified to jasmonic acid has one carbon atom.

10. The method of claim 4, wherein at least one of the one or more nutrient media further comprise heavy metal ions, heavy metal complexes, or heavy metal-containing compounds.

11. The method of claim 10, wherein the heavy metal ions are cobalt ions, the heavy metal complexes are cobalt complexes, and the heavy metal-containing compounds are cobalt-containing compounds.

12. The method of claim 4, wherein at least one of the one or more nutrient media comprise an antiethylene agent.

13. The method of claim 12, wherein the antiethylene agent is an ethylene-biosynthesis antagonist.

14. The method of claim 13, wherein the ethylene-biosynthesis antagonist is a compound which inhibits aminocyclopropane carboxylic acid (ACC) synthase, ACC oxidase, or ethylene oxidase.

15. The method of claim 13, wherein the ethylene-biosynthesis antagonist is acetylsalicylic acid or aminooxyacetic acid.

16. The method of claim 12, wherein the antiethylene agent is an ethylene-action antagonist.

17. The method of claim 16, wherein the ethylene-action antagonist is a silver-containing compound, a silver complex or silver ion.

18. The method of claim 17, wherein the silver-containing compound is at least one compound selected from the group consisting of silver thiosulfate, silver chloride, and silver oxide.

19. The method of claim 17, wherein the silver-containing compound is at least one compound selected from the group consisting of silver phosphate, silver benzoate, toluenesulfonic acid silver salt, silver acetate, silver nitrate, and silver sulfate.

20. The method of claim 17, wherein the silver-containing compound is at least one compound selected from the group consisting of silver pentafluoropropionate, silver cyanate, lactic acid silver salt, silver hexafluorophosphate, citric acid trisilver salt, and silver nitrite.

21. The method of claim 17, wherein the concentration of silver ion, silver complex, or silver-containing compound is 10 μM-100 μM.

22. The method of claim 17, wherein the concentration of silver ion, silver complex, or silver-containing compound is 50 μM.

23. The method of claim 17, wherein the concentration of silver ion, silver complex, or silver-containing compound is 10 μM.

24. The method of claim 17, wherein the one or more nutrient media in molar comprise a molar ratio of silver:jasmonate of less than 9.5:1.

25. The method of claim 1, wherein the one or more nutrient media comprise the inhibitor of phenylpropanoid metabolism.

26. The method of claim 25, wherein the inhibitor of phenylpropanoid metabolism is selected from the group consisting of 3,4,-methylenedioxynitrocinnamic acid. 3,4-methylenedioxycinnamic acid, 3,4-methylenedioxy-phenyl-propionic acid, 3,4-methylenedioxyphenylacetic acid, 3,4-methylenedioxybenzoic acid, 3,4,-trans-dimethoxycinnamic acid, 4-hydroxycinnamic acid, phenylpropionic acid, fluorophenylalanine, 1-aminobenzotriazole, 2-hydroxy-4,6-dimethoxybenzoic acid, 2-(diethylamino)ethyl ester of α-phenyl-α-propylbenzeneacetic acid, ammonium oxalate, vinylimidazole, diethyldithiocarbamic acid, and sinapic acid.

27. The method of claim 1, wherein the one or more nutrient media comprise at least one enhancement agent selected from each of at least two of the following classes of enhancement agents: (a) jasmonic acid or an alkyl ester thereof, (b) antiethylene agents, and (c) inhibitors of phenylpropanoid metabolism.

28. The method of claim 27, wherein the jasmonic acid alkyl ester is methyl jasmonate.

29. The method of claim 1 or claim 27, wherein the one or more nutrient media further comprise an auxin-related growth regulator selected from the group consisting of 1-Naphthaleneacetic acid, 2-Naphthaleneacetic acid, 1-Naphthaleneacetamide/Naphthylacetamide, N-(1-Naphthyl)phthalamic acid, 1-Naphthoxyacetic acid, 2-Naphthoxyacetic acid, beta-Naphthoxyacetic acid, 1-Naphthoxyacetamide, 3-Chlorophenoxyacetic acid, 4-Chlorophenoxyacetic acid, 4-Iodophenoxyacetic acid, Indoleacetamide, Indoleacetic acid, Indoylacetate, Indoleacetyl leucine, Gamma-(3-Indole)butyric acid, 4-Amino-3,5,6-trichloropicolinic acid, 4-Amino-3,5,6-trichloropicolinic acid methyl ester, 3,6-Dichloro-o-anisic acid, 3,7-Dichloro-8-quinolinecarboxylic acid, Phenylacetic acid, 2-Iodophenylacetic acid, 3-Iodophenylacetic acid, 2-Methoxyphenylacetic acid, Chlorpropham, 4-chloroindole-3-acetic acid, 5-Chloroindole-3-acetic acid, 5-Bromo-4-chloro-3-indoyl butyrate, Indoleacetyl phenylalanine, Indoleacetyl glycine, Indoleacetyl alanine, 4-chloroindole, p-chlorophenoxyisobutyric acid, 1-pyrenoxylbenzoic acid, Lysophosphatidic acid, 1-naphthyl-N-methylcarbamate, Ethyl-5-chloro-1H-Indazole-3-ylacetate-3-Indolebutanoic acid, Naphthalene-2,6-dicarboxylic acid, Naphthalene-1,4,5,8-tetracarboxylic acid dianhydride, Naphathalene-2-sulfonamide, 4-Amino-3,6-disulfo-1,8-naphthalic anhydride, 3,5-dimethylphenoxyacetic acid, 1,8-Naphthalimide, 2,4-Dichlorophenoxyacetic acid, 2,3-Dichlorophenoxyacetic acid, 2,3,5-Trichlorophenoxyacetic acid, 2-Methyl-4-chlorophenoxyacetic acid, Nitrophenoxyacetic acids, DL-alpha-(2,4-Dichlorophenoxy)propionic acid, D-alpha-(2,4-Dichlorophenoxy)propionic acid, 4-Bromophenoxyacetic acid, 4-Fluorophenoxyacetic acid, 2-Hydroxyphenoxyacetic acid, 5-Chloroindole, 6-Chloro-3-indoylacetate, 5-Fluoroindole, 5-Chloroindole-2-carboxylic acid, 3-Chloroindole-2-carboxylic acid, Indole-3-pyruvic acid, 5-Bromo-4-chloro-3-indoylbutyrate, 6-Chloro-3-indoylbutyrate, Quinoline-2-thioglycolic acid, Aminophenylacetic acids, 3-Nitrophenylacetic acid, 3-Chloro-4-hydroxybenzoic acid, Chlorflurenol, 6-Chloro-3-indoyl acetate, N-(6-aminohexyl)-5-chloro-1-Naphthalenesulfonamide hydrochloride, 2-chloro-3(2,3-dichloro-phenyl) propionitrile, o-chlorophenoxyacetic acid, 6,7-dimethoxy-1,2-benzisoxazole-3-acetic acid, 3-oxo-1,2,-benzisothiazoline-2-ylacetic acid, Mastoparan, 2,3,5-Triiodobenzoic acid, 2-(3-chlorophenoxy)propanoic acid, Mecoprop, Naphthoic acid hydrazide, 2,4-Dibromophenoxyacetic acid, 3-Trifluoromethylphenoxyacetic acid, Oxindole, Indole-2-carboxylic acid, Indole-3-lactic acid, Beta-(3-Indole)propionic acid, 2-Bromophenylacetic acid, 3-Bromophenylacetic acid, 2-Chlorophenylacetic acid, 3-Chlorophenylacetic acid, 2-Methylphenylacetic acid, 3-Methylphenylacetic acid, 3-Trifluoromethylphenylacetic acid, 3-Methylthiophenylacetic acid, Phenylpropionic acid, 4-chloro-2-methylphenylthioacetic acid, 2-Chlorobenzoic acid, 3-Chlorobenzoic acid, 2,3-Dichlorobenzoic acid, 3,4-Dichlorobenzoic acid, 2,3,5-Trichlorobenzoic acid, 2,4,6-Trichlorobenzoic acid, 2-Benzothiazoleoxyacetic acid, 2-Chloro-3-(2,3-dichlorophenyl)propionitrile, 2,4-Diamino-s-triazine, Naphthalic anhydride, Dikegulac, chlorflurecolmethyl ester, 2-(p-chlorophenoxy)-2-methylpropionic acid, 2-chloro-9-hydroxyfluorene-9-carboxylic acid, 2,4,6-trichlorophenoxyacetic acid, 2-(p-chlorophenoxy)-2-methyl propionic acid, Ethyl 4-(chloro-o-tolyloxy)butyrate, [N-(1,3-dimethyl-1H-Pyrazol-5-yl)-2-(3,5,6-Trichloro-2-pyridinyl)oxy]acetamide, 4-Chloro-2-oxobenzothiazolin-3-yl-acetic acid, 2-(2,4-Dichlorophenoxy)propanoic acid, 2-(2,4,5-Trichlorophenoxy) propanoic acid, 4-Fluorophenylacetic acid, 3-Hydroxyphenylacetic acid, Orthonil, 3,4,5-Trimethoxycinnamic acid, 2(3,4-dichlorophenoxy)triethylamine, Indole-3-propionic acid, Sodium Ioxynil, 2-Benzothiazoleacetic acid, and (3-phenyl-1,2,4-thiadiazol-5-yl)thioacetic acid.

30. The method of claim 27, wherein the antiethylene agent is a silver-containing compound, a silver complex or silver ion.

31. The method of claim 27, wherein the inhibitor of phenylpropanoid metabolism is selected from the group consisting of 3,4,-methylenedioxynitrocinnamic acid, 3,4,-methylenedioxycinnamic acid, 3,4,-methylenedioxy-phenylpropionic acid, 3,4,-methylenedioxyphenylacetic acid, 3,4-methylenedioxybenzoic acid, 3,4,-trans-dimethoxycinnamic acid, 4-hydroxycinnamic acid, phenylpropionic acid, fluorophenylalanine, 1-aminobenzotriazole, 2-hydroxy-4,6-dimethoxybenzoic acid, 2-(diethylamino)ethyl ester of α-phenyl-α-propylbenzeneacetic acid, ammonium oxalate, vinylimidazole, diethyldithiocarbamic acid, and sinapic acid.

32. The method of claim 1, claim 4, or claim 27, wherein the one or more nutrient media further comprises a polyamine.

33. The method of claim 32, wherein the polyamine is selected from the group consisting of spermine, spermidine, putrescine, cadaverine, and diaminopropane.

34. The method of claim 1 or claim 27, wherein the one or more nutrient media further comprise a taxane precursor.

35. The method of claim 29, wherein the auxin-related growth regulator is picloram, indoleacetic acid, 1-naphthaleneacetic acid, indolebutyric acid, 2,4-dichlorophenoxyacetic acid, 3,7-dichloro-8-quinolinecarboxylic acid, or 3,6-dichloro-o-anisic acid.

36. The method of claim 1, wherein the amount of said one or more taxanes recovered is at least 3-fold greater than the amount obtained from cells of *Taxus* species cultured without addition of any enhancement agents selected from the group consisting of (a) jasmonate-related compounds or alkyl esters thereof, (b) anti-ethylene agents, and (c) inhibitors of phenylpropanoid metabolism.

37. The method of claim 1, wherein the amount of said one or more taxanes recovered is at least 5-fold greater than the amount obtained from cells of *Taxus* species cultured without addition of any enhancement agents selected from the group consisting of (a) jasmonate-related compounds or alkyl esters thereof, (b) anti-ethylene agents, and (c) inhibitors of phylpropanoid metabolism.

38. The method of claim 1, wherein said one or more taxanes recovered is at least one compound selected from the group consisting of taxol, 7-epitaxol, 10-deacetyl-7-epitaxol, cephalomannine, 10-deacetyltaxol, 7-xylosyl-10-deacetyltaxol, baccatin III, and 10-deacetylbaccatin III.

39. The method of claim 1, wherein said step of cultivating is carried out in a first medium having a first composition, then the medium composition is changed to a second medium having a second composition which induces taxane production.

40. The method of claim 39, wherein the concentration of nitrate is lower in the second medium than in the first medium, and the concentration of a saccharide is higher in the second medium than in the first medium.

41. The method of claim 40, wherein the first medium contains nitrate at a concentration which is 2 to 10 times the nitrate concentration in the second medium.

42. The method of claim 40, wherein the second medium contains a saccharide at a concentration which is 2 to 5 times the saccharide concentration in the first medium.

43. The method of claim 39, wherein the second medium which induces taxane production is replenished during cultivation by periodically replenishing nutrient medium components and removing spent medium.

44. The method of claim 39, wherein the second medium comprises a jasmonate-related compound or an alkyl ester thereof.

45. The method of claim 1, wherein the one or more nutrient media comprise a saccharide in a concentration of 1-150 g/L, nitrate ion in a concentration of 0.3-70 mM or a combination thereof.

46. The method of claim 40, wherein the first medium contains a saccharide in the concentration of 1-30 g/L, and nitrate ion in the concentration of 2.5-70 mM; and the second medium contains a saccharide in the concentration of 4-150 g/L, and nitrate ion n the concentration of 0.3-18 mM.

47. The method of claim 40, wherein the first medium contains a saccharide in the concentration of 5-15 g/L, and nitrate ion in the concentration of 20-30 mM; and the second medium contains a saccharide in the concentration of 35-55 g/L, and nitrate ion in the concentration of 2-7 mM.

48. The method of claim 1 or claim 27, wherein the medium is replenished during cultivation under product formation conditions by periodically replenishing nutrient medium components and removing spent medium.

49. The method of claim 1 or claim 27, wherein said step of cultivating is carried out in one nutrient medium which is the same for cell culture growth and for taxane production.

50. The method of claim 1 or claim 27, wherein cells of said *Taxus* species are cultivated by a continuous or semi-continuous process.

51. The method of claim 1, claim 4, or claim 27, wherein cells of said *Taxus* species are cultivated by a fed-batch process.

52. The method of claim 51, wherein the nutrient medium is replenished during cultivation by periodically replenishing nutrient medium components and removing spent medium.

53. The method of claim 1 or claim 27, further comprising the periodic removal of said at least one or more taxanes from the nutrient media.

54. The method of claim 1 or claim 27, wherein the *Taxus* species is selected from the group consisting of *T. canadensis, T. chinensis, T. cuspidata, T. baccata, T. globosa, T. floridana, T. wallichiana*, and *T. media*.

55. The method of claim 4 or claim 27, wherein the *Taxus* species is *Taxus brevifolia*.

56. The method of claim 1, wherein said step of cultivating is carried out in the presence of 0.03% to 15% v/v of carbon dioxide in the gas phase in equilibrium with the one or more nutrient media.

57. The method of claim 1 or claim 4, wherein said step of cultivating is carried out in the presence of 0.3% to 8% v/v of carbon dioxide in the gas phase in equilibrium with the one or more nutrient media.

58. The method of claim 1, wherein said step of cultivating is carried out in the presence of dissolved oxygen concentration between 1% to 200% of air saturation.

59. The method of claim 1, wherein said step of cultivating is carried out in the presence of dissolved oxygen concentration between 10% to 100% of air saturation.

60. The method of claim 1 or claim 4, wherein said step of cultivating is carried out in the presence of dissolved oxygen concentration between 25% to 95% of air saturation.

61. The method of claim 1 or claim 27, wherein a jasmonate-related compound or an alkyl ester thereof is added continuously to the cell culture.

62. The method of claim 1 or claim 27, wherein the one or more nutrient media further comprise glutamine.

63. The method of claim 4, wherein the one or more nutrient media further comprise a saccharide in a concentration of 1-150 µL, nitrate ion in a concentration of 0.3-70 mM or a combination thereof.

64. The method of claim 1, wherein the one or more nutrient media comprise the antiethylene agent.

65. A method for producing one or more taxanes in high yields in cell culture of a *Taxus* species comprising: cultivating in suspension culture, in one or more nutrient media under growth and product formation conditions, cells of a *Taxus* species derived from callus or suspension cultures, and recovering said one or more taxanes from said cells, said medium of said cell culture, or both, wherein at least one of the one or more nutrient media comprises a polyamine.

66. The method of claim 65, wherein said polyamine is added to at least one of the one or more nutrient media in an amount sufficient to enhance taxane production.

67. A method for producing one or more taxanes in high yields in cell culture of a *Taxus* species comprising: cultivating in suspension culture, in one or more nutrient media under growth and product formation conditions, cells of a *Taxus* species derived from callus or suspension cultures, and recovering said one or more taxanes from said cells, said medium of said cell culture, or both, wherein said step of cultivating is carried out in the presence of dissolved oxygen concentration between 10% to 100% of air saturation.

68. A method for producing one or more taxanes in high yields in cell culture of a *Taxus* species comprising: cultivating in suspension culture, in one or more nutrient media under growth and product formation conditions, cells of a *Taxus* species derived from callus or suspension cultures, and recovering said one or more taxanes from said cells, said medium of said cell culture, or both, wherein β-phenylalanine is added to the one or more nutrient media in an amount sufficient to enhance taxane production.

* * * * *